(12) United States Patent
Del Favero et al.

(10) Patent No.: US 11,578,357 B2
(45) Date of Patent: Feb. 14, 2023

(54) MODIFIED MULTIPLEX AND MULTISTEP AMPLIFICATION REACTIONS AND REAGENTS THEREFOR

(71) Applicant: AGILENT TECHNOLOGIES, INC., Santa Clara, CA (US)

(72) Inventors: Jurgen Peter Lode Del Favero, Niel (BE); Lien Heyrman, Niel (BE); Bart Tegenbos, Niel (BE); Dirk Goossens, Niel (BE); Joachim De Schrijver, Niel (BE)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 596 days.

(21) Appl. No.: 16/469,982

(22) PCT Filed: Nov. 15, 2017

(86) PCT No.: PCT/EP2017/079273
§ 371 (c)(1),
(2) Date: Jun. 14, 2019

(87) PCT Pub. No.: WO2018/108421
PCT Pub. Date: Jun. 21, 2018

(65) Prior Publication Data
US 2020/0024651 A1    Jan. 23, 2020

(30) Foreign Application Priority Data
Dec. 16, 2016 (GB) ...................... 1621477

(51) Int. Cl.
*C12Q 1/6848* (2018.01)
*C12Q 1/6853* (2018.01)

(52) U.S. Cl.
CPC ......... *C12Q 1/6848* (2013.01); *C12Q 1/6853* (2013.01)

(58) Field of Classification Search
None
See application file for complete search history.

(56) References Cited

U.S. PATENT DOCUMENTS

| | | | |
|---|---|---|---|
| 6,207,372 B1 | 3/2001 | Shuber | |
| 6,251,639 B1 * | 6/2001 | Kurn | C12Q 1/6865 435/91.2 |
| 2010/0029511 A1 * | 2/2010 | Raymond | C12N 15/1093 506/26 |
| 2013/0203057 A1 | 8/2013 | Lemieux et al. | |
| 2014/0057264 A1 | 2/2014 | Chun et al. | |
| 2016/0257994 A1 | 9/2016 | Wang et al. | |
| 2016/0348159 A1 | 12/2016 | Kim | |

FOREIGN PATENT DOCUMENTS

| | | |
|---|---|---|
| CN | 105960467 A | 9/2016 |
| EP | 3081653 A1 | 10/2016 |
| JP | 2009539379 A | 11/2009 |
| JP | 2014515604 A | 7/2014 |
| JP | 2017501737 A | 1/2017 |
| KR | 20150098928 A | 8/2015 |
| WO | 03060159 A2 | 7/2003 |
| WO | 2007146154 A1 | 12/2007 |
| WO | 2009072705 A1 | 6/2009 |
| WO | 2012134195 A2 | 10/2012 |
| WO | 2014110528 A1 | 7/2014 |
| WO | 2015126078 A1 | 8/2015 |

OTHER PUBLICATIONS

International Search Report issued in PCT/EP2017/079273, dated Mar. 27, 2018.
Shoji et al., "Modified DNA Aptamer That Binds the (R)-Isomer of a Thalidomide Derivative with High Enantioselectivity," J. Am. Chem. Soc., vol. 129, No. 5, 2007, pp. 1456-1464.
First Office Action dated Nov. 1, 2022 in Chinese Patent Application No. 201780077635.3.

* cited by examiner

*Primary Examiner* — Angela M. Bertagna
*Assistant Examiner* — Carolyn L Greene
(74) *Attorney, Agent, or Firm* — ArentFox Schiff LLP

(57) ABSTRACT

The invention relates to reagents and methods for improving the efficiency of multiplex nucleic acid amplification, in particular where overlapping amplicons are to be generated. The invention also relates to reagents and methods for improving the efficiency of multistep nucleic acid amplification, in particular the performance of two separate amplification reactions designed to occur in sequence in the same reaction mixture or vessel. The invention further relates to reagents and methods for improving multistep nucleic acid amplification reactions by controlling the output of the first amplification reaction. In particular, primers are provided that minimise the formation of aberrant amplification products. Such primers are particularly useful where first and second amplification reactions take place in a single reaction mixture or vessel.

12 Claims, 25 Drawing Sheets
Specification includes a Sequence Listing.

MODIFIED MULTIPLEX AND MULTISTEP AMPLIFICATION REACTIONS AND REAGENTS THEREFOR

CROSS REFERENCE TO RELATED APPLICATIONS

This application is a 35 U.S.C. 371 National Phase of PCT Application No. PCT/EP2017/079273 filed Nov. 15, 2017, which claims priority to GB Patent Application No. 1621477.7 filed Dec. 16, 2016, the disclosure of these prior applications are hereby incorporated by reference in their entireties.

INCORPORATION BY REFERENCE OF SEQUENCE LISTING

The Sequence Listing submitted in an ASCII text file, in accordance with 37 C.F.R. 1.821, is incorporated by reference herein. The text file name is "039062_00012_Substitute_Sequence_Listing_revised_ST25.txt", the date of creation of the text file is Mar. 24, 2022, and the size of the ASCII text file 12 KB.

FIELD OF THE INVENTION

The invention relates to reagents and methods for improving the efficiency of multiplex nucleic acid amplification, in particular where overlapping amplicons are to be generated. The invention also relates to reagents and methods for improving the efficiency of multistep nucleic acid amplification, in particular the performance of two separate amplification reactions designed to occur in sequence in the same reaction mixture or vessel. The invention further relates to reagents and methods for improving multistep nucleic acid amplification reactions by controlling the output of the first amplification reaction. In particular, primers are provided that minimise the formation of aberrant amplification products. Such primers are particularly useful where first and second amplification reactions take place in a single reaction mixture or vessel.

BACKGROUND

Multiplex polymerase chain reaction (mPCR) is a variant of PCR in which two or more target sequences can be amplified by including more than one pair of nucleic acid amplification, or PCR, primers in a single nucleic acid amplification reaction. Multiplex PCR has the potential to produce considerable savings of time and effort in the laboratory. Since it was first described in 1988, this technique has been successfully applied in many areas of DNA testing in humans, including gene deletion analysis, mutation and polymorphism analysis, quantitative analysis, and reverse-transcription (RT)-PCR. In the field of infectious diseases, multiplex PCR has been shown to be a valuable tool for identification of viruses, bacteria, and parasites.

The optimization of mPCR, however, poses several difficulties, including poor sensitivity, poor specificity, preferential amplification of certain specific targets and/or amplification of unintended sequences.

Preferential amplification of one target sequence over another is a known phenomenon in mPCR. Two major classes of processes that induce this bias have been identified: PCR drift and PCR selection. PCR drift is a bias assumed to be due to fluctuation in the interactions of PCR reagents, particularly in the early cycles, especially in the presence of very low template concentration. PCR selection, on the other hand, is defined as a mechanism that favors the amplification of certain templates due to the properties of the target, the target's flanking sequences, or the entire target genome. These properties include the preferential amplification of shorter sequences.

In particular, the presence of more than one primer pair in the multiplex PCR increases the chance of obtaining aberrant amplification products, for example, due to the preferential amplification of shorter, undesired, fragments. FIG. 1 illustrates the issue of amplification of aberrant (unintended) amplicons faced when performing mPCR.

The inventors aimed to address the problem in developing multiplex PCR based tests of undesired, aberrant products (shorter aberrant products being preferred) which requires the use of multiple reaction vessels for a single test. As an example, a current PCR test to amplify overlapping regions of a BRCA gene requires that amplifications are performed in four separate tubes to ensure reliable coverage of the target sequences. This increases the complexity of the test.

Typically, a multiplex PCR will occur in two separate reactions. In the first reaction a set of target specific primers with universal tags are used to add universal forward and reverse tags onto each amplicon. The products are then purified prior to a second amplification reaction. In the second reaction, universal primers designed against these tags are then used to amplify all of the amplicons and to add any further sequences needed for further processing and identification purposes (such as adaptors).

This system is suboptimal and labour intensive. Moreover, the requirement to stop and separate the reaction mixture after the first step introduces possible errors and contamination into the system. Therefore it would be desirable to identify a method to allow for the performance of both of these steps in a single reaction vessel.

SUMMARY OF THE INVENTION

The inventors have devised various solutions to problems they have encountered with multiplex and multistep nucleic acid amplification reactions. Ideally, the various solutions can be combined to permit amplification of overlapping target sequences in a first amplification followed by "universal" amplification (i.e. based on a common primer pair irrespective of the target sequence) to incorporate adapter sequences into the final amplification products that can be used in further detection methodologies, preferably next generation sequencing. For the sake of clarity, each area of improvement is described under a separate heading and various combinations are discussed thereafter. However, it should be borne in mind that the various solutions have been devised so as to be advantageously combined and all such combinations are envisaged within the scope of the invention. It should also be appreciated that options described in relation to one area of improvement will apply mutatis mutandis to other areas; e.g. sample types, nucleic acid types etc. as appropriate. Nevertheless, for the ease of understanding elements common to all aspects of the invention, the following introductory definitions are provided. Such definitions apply throughout the disclosure of the invention, with additional clarification being provided when each aspect is described in further detail.

The invention is concerned with nucleic acid amplification reactions. According to all aspects of the invention, the nucleic acid amplification is typically and preferably by PCR. However, the invention can be adapted to other amplification systems as required as would be appreciated by one skilled in the art.

The invention is particularly concerned with multiplex nucleic acid amplification in which two or more target sequences are amplified in parallel. This is typically achieved by including more than one pair of nucleic acid amplification primers in a single nucleic acid amplification reaction. According to some aspects of the invention, the multiplex amplification involves primer pairs that amplify overlapping regions of the target nucleic acid molecule.

The invention is also concerned with multistep nucleic acid amplification in which two or more distinct amplification reactions take place. Typically, a first amplification reaction utilises target specific primers that amplify the target nucleic acid molecules. The target specific primers also comprise universal tags. The universal tags are incorporated into the amplification products as the reaction proceeds. In the second amplification reaction, universal primers designed to hybridise with these tag sequences are then used to amplify the amplification products from the first amplification. This second amplification involves primers that incorporate any further sequences needed for further processing and identification purposes (such as adaptors). Thus, the concept of "universal" amplification is governed by the fact that the amplification is performed independently of the specific target sequence of the initial target molecule that is amplified. It relies upon the incorporation into the amplification products from the first amplification reaction of additional sequence (so-called "universal tags") that can act as primer binding sites in a second amplification. Thus, the primer region of the primers in the second amplification corresponds to the universal tag sequence. Primers including such primer regions are referred to herein as "universal primers".

The target nucleic acid molecule is not limiting according to the invention. Any suitable target nucleic acid molecule may be amplified using the reagents and methods of the invention. Multiple different target nucleic acid molecules may be targeted. This may involve use of multiple target nucleic acid specific primer pairs. According to all aspects of the invention, when the target nucleic acid molecule is double-stranded, the primer regions of the forward and reverse primers of each specific primer pair are complementary or substantially complementary to, and can hybridise with, the antiparallel, complementary strands of the double-stranded target nucleic acid molecule respectively. Of course, as the target nucleic acid molecule is amplified (replicated) during an amplification process, the forward and reverse primers of each specific primer pair can bind via their respective primer regions to the complementary region of the amplified (replicated) target nucleic acid molecule formed during amplification. This will, in fact, occur preferentially as the amplified (replicated) target nucleic acid molecule is (exponentially) formed during amplification, as will be apparent to the skilled person in view of amplification processes known in the art. Thus, the term "target nucleic acid molecule" refers to the desired region of a nucleic acid molecule to be amplified, whether as part of the initial target nucleic acid molecule present before amplification begins or a target nucleic acid molecule generated during amplification. The term "initial target nucleic acid molecule" is thus used to refer to the target nucleic acid molecule present before amplification begins (i.e. as extracted from the originating sample).

In preferred embodiments, according to all aspects of the invention, the target nucleic acid molecule is a DNA molecule. The DNA may be genomic DNA, mitochondrial DNA etc. Genomic DNA is preferred. The DNA may be purified from any suitable sample. Sample types include blood samples (in particular from plasma, and also serum), other bodily fluids such as saliva, urine or lymph fluid. Other sample types include solid tissues, including frozen tissue or formalin fixed, paraffin embedded (FFPE) material. In particularly preferred embodiments, the DNA molecule is a double-stranded DNA (dsDNA) molecule. The strands may be referred to as the 'sense' or 'coding' strand and 'anti-sense' or 'non-coding' strand respectively, as is customary in the art. In these embodiments, the primer region of the forward primer of a specific primer pair is complementary to a region of the anti-sense strand and the primer region of the reverse primer of the same specific primer pair is complementary to a region of the sense strand downstream of the region to which the forward primer binds. In alternative embodiments, the DNA molecule is a single-stranded DNA (ssDNA) molecule. In some embodiments, ssDNA has already been denatured in situ in the original sample. For example, the ssDNA may be purified from FFPE material. Where ssDNA is used, the primer region of either the forward or reverse primer of a specific primer pair is complementary to the ssDNA molecule. The other primer of the specific primer pair comprises a primer region which is complementary to, and therefore hybridises with, the complementary ssDNA molecule formed during an amplification cycle. In further embodiments, the initial target nucleic acid molecule may be present as both a ssDNA and a dsDNA molecule. For instance, in the case of DNA purified from FFPE material, the DNA may include both ssDNA and dsDNA. The DNA may be found in, or derived from cells in a sample. Alternatively the DNA may be circulating, or "cell-free", DNA (cfDNA). Such DNA can be obtained from a range of bodily fluids including blood samples (in particular from plasma, and also serum), other bodily fluids such as saliva, urine or lymph fluid.

In some embodiments, according to all aspects of the invention, the target nucleic acid molecule is derived from a RNA molecule. RNA may be obtained from the same sample types as DNA, as discussed above. The RNA may be messenger RNA (mRNA), microRNA (miRNA) etc. mRNA is preferred. In such embodiments, the RNA is typically reverse transcribed using a reverse transcriptase enzyme to form a complementary DNA (cDNA) molecule that can then be amplified using the primers of the invention. Methods for reverse transcribing RNA to cDNA using a reverse transcriptase are well-known in the art. Any suitable reverse transcriptase can be used, examples of suitable reverse transcriptases being widely available in the art. In such embodiments, the initial target nucleic acid molecule is thus a cDNA molecule. The initial cDNA molecule may be single stranded until DNA polymerase has been used to generate the complementary strand. This synthesis of the complementary strand can be performed using a primer of the invention. Once a double stranded DNA molecule is generated, the primer pairs of the invention can direct further amplification. Therefore, in particular embodiments, according to all aspects of the invention, RNA from a sample is firstly reverse transcribed to cDNA followed by amplification of the cDNA molecule using sets of primers as defined herein. The reverse transcription reaction and subsequent amplification reaction may (preferably) both occur in the same reaction vessel.

Thus, as will be apparent, the "primer region" of each primer, according to all aspects of the invention, defines the region of the primer which can hybridise with a strand of the target nucleic acid molecule to direct synthesis of a new, complementary nucleic acid molecule strand by a (DNA) polymerase enzyme.

The target nucleic acid molecules may be obtained from any suitable sample. As would be readily appreciated, the methods of the invention are in vitro methods and may be performed using a pre-isolated sample. The sample may be taken from a human subject in preferred embodiments. However, potentially any nucleic acid containing sample from any source is amenable to amplification according to the various aspects of the present invention.

The primer pairs designed to amplify the target nucleic acid molecule generally incorporate tags. Those tags are, in most embodiments of the invention, critical to enable the universal amplification to occur and are referred to herein as "universal tags". Such tags do not need to hybridize with the initial target nucleic acid molecule. This function is provided by the primer region. However, once the tags have been included in an amplification product they can then act as a subsequent target to which the universal primers hybridise in the second amplification step. Suitable tags are well known in the art. Typically tags are of sufficient length to allow universal primers to be specifically designed against that sequence. Thus, they are typically 20 nucleotides or more in length. Tags useful according to the present invention may comprise, consist essentially of or consist of the nucleotide sequence of SEQ ID No 1 (Tag 1) or 2 (Tag 2).

According to all aspects of the invention, the second amplification may be used to include adaptor sequences into the further amplification products. The adaptor sequence may be any suitable sequence for downstream processing. Downstream processing permits the target nucleic acid to be detected and/or quantified in the sample. For example, an adaptor sequence complementary to an oligonucleotide immobilised on a suitable solid surface allows a sequence incorporating such an adapter to be immobilised. Other applications rely on the adaptor hybridizing to an oligonucleotide in a liquid. Adaptors may be useful for array based or sequencing based analyses. In preferred embodiments according to all aspects of the invention, the adapter sequence may be any suitable adapter sequence for high-throughput nucleic acid sequencing. Such sequencing is typically and preferably performed using a next generation sequencing (NGS) platform. Examples of NGS platforms include Illumina sequencing (such as Hi-Seq and Mi-Seq), SMRT sequencing (Pacific Biosciences), Nanopore sequencing, SoLID sequencing, pyrosequencing (e.g. Roche 454), single molecule sequencing (SeqLL/Helicos) and Ion-Torrent (Thermo Fisher) which are well-known to the skilled person. As the skilled person is aware, the adapter sequence is complementary to an oligonucleotide immobilised on a suitable solid surface (the nature of which depends on the sequencing platform, such as a flow cell (Illumina), zero mode waveguide (SMRT) or bead (pyrosequencing)) for sequencing. The invention is not intended to be limited in relation to the specifics of the adapter sequence. The advantages of the invention lie in modifications to the amplification reagents and processes rather than how the downstream processing is performed. Specific examples of adapters include p5 and p7 adapters useful for sequencing on the Illumina MiSeq or HiSeq platform as well as A and P1 adapters useful for sequencing using the Thermo Fisher Ion-Torrent platform.

The various primers of the invention may also be used to include barcodes into the amplification products. Barcode sequences are known in the art. For aspects of the invention concerning the target-specific primers used in the first amplification, molecular barcodes are advantageously included in the primers. A molecular barcode is a specific nucleic acid sequence that enables the subsequent amplicon in which it is incorporated to be identified in in post-sequencing, in silico analysis.

The main form of barcode that is particularly relevant to aspects of the present invention involving the second round of amplification (typically so called "universal" amplification, preferably universal PCR) are sample barcodes. Thus, sample barcodes may advantageously be included in second round amplification (i.e. universal) primers. A sample barcode sequence is used to allow sample identification. This is advantageous where multiple samples are being investigated in a single sequencing run. However, this is optional. For some applications, e.g. ultra-deep sequencing of a sample, a sample barcode sequence may be redundant. Where included, the sample barcode sequence may be any suitable sample barcode sequence for high-throughput nucleic acid sequencing. The barcode sequence may be selected based on the chosen NGS platform in some embodiments. The sample barcode sequence may also be referred to as a molecular identifier (MID) sequence or a unique index sequence herein. It is a pre-determined, unique (compared to other barcode sequences) sequence that can be used in post-sequencing, in silico analysis to identify the origin of a specific amplicon and to group amplicons of a specific origin together. Use of such sequences is well-known in the art. In specific embodiments each sample barcode is at least 4, 6 or 8 nucleotides, optionally up to 20 nucleotides, in length.

In some aspects of the invention, the primers or primer-encoding sequences may incorporate a blocking group. The blocking group prevents unwanted extension of the relevant sequence. Any suitable blocking group for this purpose may be employed and the skilled person is well aware of blocking groups that can be used. In certain embodiments the blocking group is selected from the following: 3'ddC, 3' Inverted dT, 3' C3 spacer (such as a C3 propanediol spacer), 3' Amino, and 3' phosphorylation.

One key advantage of the present invention is the ability to perform multiplex and multistep reactions in a single reaction mixture. By "single reaction mixture" is meant that all of the method steps up to and including generating the relevant amplification products (both first and second round) are carried out without the need to separate or remove components. In particular, there is no requirement to purify the first amplification products prior to the universal amplification. In some embodiments all of the reagents required for the method (i.e. to generate the further amplification products) are combined before the first amplification is carried out. Thus, the method may be performed in a single reaction vessel. The reaction vessel may not need to be further manipulated once the reaction mixture has formed (apart from performing the amplification itself e.g. thermal cycling) until the further amplification products have been generated. The methods may, therefore, be considered to be a "one tube" or "homogenous" method. The invention relates to reaction vessels containing the necessary reagents to perform the amplification reactions described herein.

For the avoidance of doubt, methods of the invention encompass the performance of additional steps after the generation of the further amplification products (i.e. after the universal, or second round, amplification). Such methods are not constrained to the same reaction mixture of reaction vessel. Such methods typically involve detecting, and often quantifying, the target nucleic acid molecule. In preferred embodiments, the methods of the invention are used to identify and optionally quantify specific target nucleic acid molecules. In preferred embodiments the method further comprises sequencing the further amplification products. Sequencing is typically performed in massively parallel fashion. Preferably, sequencing is performed using a next generation sequencing (NGS) technique. The sequencing may take place in a different reaction mixture to that of the amplification reactions of the invention.

The term "amplicon" is used interchangeably with "amplification product" herein.

Improving Multiplex Amplifications Involving Overlapping Target Sequences

The inventors have developed improved reagents for performing multiplex amplification (especially mPCR) involving overlapping target sequences. In particular, the inventors provide means to limit or nullify amplification of aberrant amplicons (i.e. unintended amplicons) in a multiplex nucleic acid amplification assay such as mPCR. This is particularly advantageous for performing a multiplex nucleic acid amplification assay in a single reaction vessel or mixture. It removes the requirement to perform overlapping amplification reactions in separate reaction vessels or mixtures.

Thus, in a first aspect, the invention provides a set of primers for use in multiplex amplification of overlapping regions of a target nucleic acid molecule, comprising:

a. a first primer pair designed to amplify a first region of the target nucleic acid molecule, comprising:
   i. a first forward primer incorporating a primer region that hybridizes with a strand of the target nucleic acid molecule
   ii. a first reverse primer incorporating a primer region that hybridizes with a strand of the target nucleic acid molecule and a nucleic acid tag 5' of the primer region
b. a second primer pair designed to amplify a second region of the target nucleic acid molecule that at least partially overlaps with the first region, comprising:
   i. a second forward primer incorporating a primer region that hybridizes with a strand of the target nucleic acid molecule and a nucleic acid tag 5' of the primer region which is identical in the 5' to 3' direction with the nucleic acid tag incorporated at the 5' end of the first reverse primer
   ii. a second reverse primer incorporating a primer region that hybridizes with a strand of the target nucleic acid molecule, wherein, in the event that an aberrant (short) amplification product is formed between the first reverse primer and second forward primer, an intramolecular hybridization event occurs between the nucleic acid tag at the 5' end of the aberrant (short) amplification product and the complementary sequence at the 3' end of the aberrant (short) amplification product formed during amplification to form a secondary structure that precludes further amplification of the aberrant amplification product. This is illustrated in FIG. 2 to demonstrate the concept. The first region of the target nucleic acid molecule is upstream (in the 5' to 3' direction (on the sense strand when double stranded)) of the second region of the target nucleic acid molecule.

In some embodiments, the first forward primer and second reverse primer also incorporate a nucleic acid tag 5' of the primer region. In addition, the nucleic acid tag of the first forward primer and the nucleic acid tag of the second reverse primer are identical in the 5' to 3' direction such that, in the event that an aberrant (long) amplification product is formed between the first forward primer and second reverse primer, an intramolecular hybridization event occurs between the nucleic acid tag at the 5' end of the aberrant (long) amplification product and the complementary sequence at the 3' end of the aberrant (long) amplification product formed during amplification to form a secondary structure that precludes further amplification of the aberrant amplification product. This is illustrated in FIG. 4 to demonstrate the concept.

Thus, according to all aspects herein, aberrant amplification products can be distinguished (from each other and, if needed, from desired amplification products) according to length. The "short" aberrant amplification products result from the reverse primer of a first primer pair forming an amplification product with the forward primer of an immediately downstream second primer pair. In contrast, "long" aberrant amplification products result from the forward primer of a first primer pair forming an amplification product with the reverse primer of an immediately downstream second primer pair. Short aberrant products are particularly problematic and thus are one focus of the invention.

Where both primers in a specific primer pair designed to amplify a specific region of the target nucleic acid molecule contain a nucleic acid tag 5' of the primer region, the nucleic acid tags incorporated into each primer in the pair (e.g. the nucleic acid tag of the first forward primer and the nucleic acid tag of the first reverse primer) are different. Thus, the tags are not substantially identical and, preferably, share no identity in the 5' to 3' direction. Accordingly, the mechanism by which further amplification of aberrant amplification products is precluded is avoided. No reverse complementary sequence to the 5' nucleic acid tag is formed at the 3' end of the desired amplification product to enable an intramolecular hybridization event to occur. This is illustrated in FIG. 4 to demonstrate the concept.

In further embodiments, the set of primers further comprises:

a. a third primer pair designed to amplify a third region of the target nucleic acid molecule that at least partially overlaps with the second region, comprising:
   i. a third forward primer incorporating a primer region that hybridizes with a strand of the target nucleic acid molecule and a nucleic acid tag 5' of the primer region
   ii. a third reverse primer incorporating a primer region that hybridizes with a strand of the target nucleic acid molecule, wherein the nucleic acid tag of the third forward primer and the nucleic acid tag of the second reverse primer are also identical in the 5' to 3' direction such that, in the event that an aberrant (short) amplification product is formed between the third forward primer and second reverse primer, an intramolecular hybridization event occurs between the nucleic acid tag at the 5' end of the aberrant (short) amplification product and the complementary sequence at the 3' end of the aberrant (short) amplification product formed during amplification to form a secondary structure that precludes further amplification of the aberrant (short) amplification product. This is illustrated in FIG. 5A-C to demonstrate the concept. The third region of the target nucleic acid molecule is downstream (i.e. in the 5' to 3' direction on the sense strand) of the second region of the target nucleic acid molecule.

In further embodiments, the third reverse primer also incorporates a nucleic acid tag 5' of the primer region, further characterised in that the nucleic acid tag of the second forward primer and the nucleic acid tag of the third reverse primer are also identical in the 5' to 3' direction such that, in the event that an aberrant (long) amplification product is formed between the second forward primer and third reverse primer, an intramolecular hybridization event occurs between the nucleic acid tag at the 5' end of the aberrant (long) amplification product and the complementary sequence at the 3' end of the aberrant (long) amplification product formed during amplification to form a secondary structure that precludes further amplification of the aberrant amplification product. This is illustrated in FIG. 5A-C to demonstrate the concept.

In analogous fashion, the set of primers may further comprise a fourth primer pair, fifth primer pair etc. designed to amplify a fourth region of the target nucleic acid molecule that is downstream of (in the 5' to 3' direction on the sense strand) and at least partially overlaps with the third region, a fifth region of the target nucleic acid molecule that is downstream of (in the 5' to 3' direction on the sense strand) and at least partially overlaps with the fourth region etc respectively; the fourth, fifth etc primer pairs having one or more nucleic acid tags as described for the first, second or third primer pairs mutatis mutandis. The total number of primer pairs in the set of primers that can be used simultaneously in a single multiplex amplification reaction (such as mPCR) according to the invention is not particularly limited but, instead, dependent on the number of desired amplicons, efficiency of the (DNA) polymerase used as would be understood by the skilled person. In specific embodiments, the number of primer pairs in the set of primers may be at least 5, 10, 15, 20, 25, 30, 40, 50, 60, 70, 80, 90, 100, 150, 200, 300, 400, 500, 600, 700, 800, 900, 1000, 2000, 3000, 4000, 5000 etc. In specific embodiments, the number of primer pairs in the set of primers may be up to 5, 10, 15, 20, 25, 30, 40, 50, 60, 70, 80, 90, 100, 150, 200, 300, 400, 500, 600, 700, 800, 900, 1000, 2000, 3000, 4000, 5000 etc.

Any number of primer pairs following this arrangement may be provided according to the invention to allow potentially large DNA targets to be amplified efficiently in a multiplex format, while minimising or eliminating production of aberrant amplification products. The reciprocal arrangement of identical tags between neighbouring primer pairs can be used according to any desired overall number of primer pairs. Similarly, multiple distinct targets may be multiplexed in a single reaction. At least one of the targets and preferably all targets involve amplification of overlapping regions and thus may be amplified using primer sets of the invention.

Accordingly, in a central and highly advantageous aspect, the invention provides a set of primers for use in multiplex amplification of overlapping regions of a target nucleic acid molecule, comprising:
  a. at least two primer pairs designed to amplify overlapping regions of the target nucleic acid molecule, each primer pair comprising:
    i. a forward primer incorporating a primer region that hybridizes with a strand of the target nucleic acid molecule and a nucleic acid tag 5' of the primer region
    ii. a reverse primer incorporating a primer region that hybridizes with a strand of the target nucleic acid molecule and a nucleic acid tag 5' of the primer region,
wherein the nucleic acid tag of the forward and reverse primer in each primer pair are different, the tag of the forward and reverse primer in immediately neighbouring primer pairs are identical in the 5' to 3' direction such that, in the event that an aberrant amplification product is formed between the forward and reverse primers of immediately neighbouring primer pairs, an intramolecular hybridization event occurs between the nucleic acid tag at the 5' end of the aberrant amplification product and the complementary sequence at the 3' end of the aberrant amplification product formed during amplification to form a secondary structure that precludes further amplification of the aberrant amplification product.

Note that a "primer pair" as described herein refers to a pair of primers designed to produce a particular desired amplification product. Thus, primer pair is not a term used to describe the primers that may inadvertently result in generation of aberrant amplification products. The nucleic acid tag of the forward and reverse primer in each primer pair are different. This precludes generation of intended amplification products that are prevented from being further amplified. In contrast thereto, the tag of the forward and reverse primer in immediately neighbouring primer pairs are identical in the 5' to 3' direction. As explained in detail herein, such an arrangement ensures that, in the event that an aberrant amplification product is formed between the forward and reverse primers of immediately neighbouring primer pairs, an intramolecular hybridization event occurs between the nucleic acid tag at the 5' end of the aberrant amplification product and the complementary sequence at the 3' end of the aberrant amplification product formed during amplification. This results in the formation of a secondary structure that precludes further amplification of the aberrant amplification product. Accordingly, this overall arrangement of tags within and between primer pairs precludes the further generation of both short and long aberrant amplification products.

According to all aspects of the invention, the nucleic acid tag is a region of the primer which is not complementary to, and therefore cannot hybridise with, the initial target nucleic acid molecule. When an aberrant amplification product is formed comprising the nucleic acid tag at its 5' end and the complementary sequence at its 3' end (which is generated during amplification, as illustrated in FIGS. 3A-C and described in detail herein), an intramolecular hybridization event occurs between the nucleic acid tag and its complement sequence at the 3' end of the aberrant amplification product to form a secondary structure that precludes further amplification of the aberrant amplification product.

More specifically, when an aberrant amplification product is formed during a round, or cycle (which terms are used interchangeably herein), of amplification and is heated to a sufficient degree to dissociate (melt) into single nucleic acid strands in the next round, or cycle, of amplification (per amplification methods such as PCR which are well-known in the art), hybridisation of the nucleic acid tag and its complement sequence at the 3' end of the single-stranded aberrant amplification product is favoured over intermolecular hybridisation of the single-stranded aberrant amplification product with a further primer when the temperature is subsequently lowered during the annealing step. This intramolecular hybridisation event forms a secondary structure that precludes further amplification of the aberrant amplification product. The interaction between tag and complement may generate a hairpin, or horseshoe, shaped molecule. The precise conformation of the secondary structure is not important. What is important is that the interaction between the ends of the molecules precludes further amplification of the aberrant amplification product.

The tags are formed of a sequence of nucleotides and may be DNA- or RNA-based or a combination of the two provided they can be used as a template for a (DNA) polymerase to synthesize the complementary sequence. Preferably they are composed of DNA. The nucleic acid tag may comprise canonical and/or non-canonical nucleotides. Canonical nucleotides include guanine, cytosine, thymine, adenine and uracil. Non-canonical nucleotides include inosine, thiouridine, isoguanine, isocytosine and diaminopyrimidine. The skilled person is well aware of suitable, complementary nucleotide base pairings i.e. a base pairing being a pair of nucleotides able to hybridise with one another.

Melting temperature (Tm) is defined in the art (and herein) as the temperature at which the two strands of a nucleic acid duplex will dissociate to become single stranded. Thus, Tm provides an indication of the duplex stability. In specific embodiments, the Tm of the secondary structure resulting from intramolecular hybridization between complementary tag-derived sequences (in a short aberrant amplification product) is higher than the highest Tm of the primers in the context of intermolecular hybridization to the target sequence. Thus, at temperatures which cause the primers to dissociate from their complementary binding region of the target nucleic acid molecule, the secondary structure formed between the nucleic acid tag and its complement sequence at the 3' end of the single-stranded aberrant amplification product may remain intact and, therefore, further amplification of the aberrant amplification product is precluded. In particular, the Tm of the secondary structure resulting from intramolecular hybridization between complementary tag-derived sequences (in a short aberrant amplification product) may be at least 1 or 2° C. higher, optionally up to 3, 4, 5, 6, 7, 8, 9 or 10° C., or more, higher than the highest Tm of the primers in the context of intermolecular hybridization to the target sequence.

The tag incorporated into the primers of the invention may comprise, consist essentially of or consist of a universal tag. This universal tag sequence is included into the amplification products and thus allows a second amplification to take place that requires the use of universal primers. For a pair of primers as defined herein (i.e. a forward primer and reverse primer designed to amplify a desired amplification product), the universal tag sequence incorporated into the forward primer is different from the universal tag sequence incorporated into the reverse primer. This prevents generation of intended (desired) amplification products that are prevented from being further amplified. However, in contrast to the prior implementation of such tag sequences, in the present invention, the universal tag of the forward and reverse primer in immediately neighbouring primer pairs are identical in the 5' to 3' direction. As explained in detail herein, such an arrangement ensures that, in the event that an aberrant amplification product is formed between the forward and reverse primers of immediately neighbouring primer pairs, an intramolecular hybridization event occurs between the universal tag at the 5' end of the aberrant amplification product and the complementary sequence at the 3' end of the aberrant amplification product formed during amplification. This results in the formation of a secondary structure that precludes further amplification of the aberrant amplification product. Accordingly, this overall arrangement of universal tags within and between primer pairs precludes the further generation of both short and long aberrant amplification products.

It should be understood that a universal tag sequence is so-called "universal" because the same pair of sequences may be employed for all primers. A second round of amplification can then be directed, irrespective of the target sequence, by a single universal primer pair. However, in the present invention, the reciprocating arrangement of tags between neighbouring primer pairs simply means that the universal primers will act in corresponding fashion to amplify the products from the first amplification reaction. Typically, such amplification products incorporate a tag and an adapter sequence at each end of the molecule. This is discussed further herein and the general concept is illustrated in FIGS. 6A-C.

It is worth further noting that this arrangement provides an opportunity, in the second amplification, to further suppress or eliminate aberrant amplification products. If any undesired amplification products are available to be amplified by the universal primers, they will further incorporate the complementary adaptor and optionally barcode sequences at either end. This extends the region of complementarity at either end of the strand and thus further favours an intramolecular interaction thereby suppressing further amplification.

As for the tags more generally, and for the avoidance of doubt, the universal tags are formed of a sequence of nucleotides and may be DNA- or RNA-based or a combination of the two provided they can be used as a template for a (DNA) polymerase to synthesize the complementary sequence. In some (RNase H) embodiments discussed herein they are not RNA-based. They are preferably composed of DNA. The universal tag may comprise canonical and/or non-canonical nucleotides. Canonical nucleotides include guanine, cytosine, thymine, adenine and uracil. Non-canonical nucleotides include inosine, thiouridine, isoguanine, isocytosine and diaminopyrimidine. The skilled person is well aware of suitable, complementary nucleotide base pairings i.e. a base pairing being a pair of nucleotides able to hybridise with one another.

Each tag must be located 5' (or upstream) of the primer region. The primers may, however, include additional sequences again upstream of the primer region. They are preferably located between the tag and the primer region, but may be upstream of the tag. Other additional sequences that may be included are probes such as so-called "scorpion" probes that permit amplification to be monitored in real-time. Such probe sequences are typically located upstream of the tag.

Yet other additional sequences that may be included are barcodes, in particular molecular barcodes which are known in the art. Briefly, each molecular barcode is a specific nucleic acid sequence that enables the subsequent amplicon in which it is incorporated to be identified in in post-sequencing, in silico analysis.

Primers may also be labelled, for example using a fluorophore, as would be readily understood by one skilled in the art.

The length of the tag can be readily determined by one skilled in the art to ensure that, in a given amplification reaction, the production of aberrant amplification products is minimised. It has been shown by the inventors that while a tag of 24 nucleotides may be optimal, a range of tag lengths is sufficient. In many embodiments, the tag is used to provide a sequence to which further "universal" primers will hybridise. Accordingly, such tags are consistent with the requirements of primer design as would be familiar to one skilled in the art. Thus in some embodiments, each tag is at least 15, 16, 17, 18, 19, 20, 21, 22, 23, 24, 25, 26, 27, 28, 29, 30, 31, 32 or 33 nucleotides in length. In some embodiments, each tag is 15, 16, 17, 18, 19, 20, 21, 22, 23, 24, 25, 26, 27, 28, 29, 30, 31, 32 or 33 nucleotides in length. In some embodiments, each tag is between 15 and 35 nucleotides in length, or between 20 and 30 nucleotides in length, preferably between 20 and 25 nucleotides in length.

The composition of a tag is also important in terms of melting temperature and hybridization properties. In further embodiments, each tag comprises a GC rich sequence. GC rich sequences are preferred as each base pair includes three hydrogen bonds (compared to AT pairs which involve only two hydrogen bonds). By "GC rich" is meant a nucleic acid sequence comprising predominantly guanine and/or cytosine nucleotides. This may be anywhere between over 50% and 100% guanine and cytosine residues. The tag may, for instance comprise 50, 55, 60, 65, 70, 75, 80, 85, 90, 95 or 100% guanine and/or cytosine nucleotides. In specific embodiments, the tag comprises entirely guanine nucleotides or entirely cytosine nucleotides. In other embodiments, the tag comprises a combination of guanine and cytosine nucleotides. Where the tag is less than 100% guanine and/or cytosine nucleotides, the remaining nucleotides may be selected from any other suitable canonical or non-canonical nucleotides.

The size of the desired amplification products may depend on the particular amplification reaction to be used. It may also depend on the nature of the target sequence. For mPCR, each primer pair may be intended to produce an amplification product in the range of 30-500 nucleotides, preferably 30-300 nucleotides and more preferably 50-150 nucleotides. Where the amplification products are to be used in subsequent next generation sequencing, each primer pair may be intended to produce an amplification product in the range of 30-500 nucleotides, preferably 30-300 nucleotides and more preferably 70-250 nucleotides. Where mPCR is used and amplification products are detected in real-time, e.g. using a probe based system, short amplification products may be preferred. Thus, each primer pair may be intended to produce an amplification product in the range of 30-300 nucleotides, preferably 30-250 nucleotides and more preferably 30-150 nucleotides. In related embodiments, the level of overlap between the intended amplification products generated from immediately neighbouring primer pairs is in the range of 10-100 nucleotides, preferably 10-50 nucleotides and more preferably 10-30 nucleotides. The region of overlap corresponds to (minus the tag sequences) the length of the short aberrant amplification products. It should be understood, however, that the length of the desired amplification products is not an essential feature of the invention. Thus, each primer pair may be intended to produce an amplification product greater than 500 nucleotides e.g. up to 1000, 2000 nucleotides etc. Each desired amplification product may be of a length at or close to the extension limit of the (DNA) polymerase enzyme employed. Thus, the invention allows the user flexibility in relation to the length of the desired amplification products since it is only the primer regions which are complementary to their target regions of interest in the target nucleic acid molecule. The design of suitable primer regions for a target region of interest (and therefore amplicon size) is customary for the skilled person in the art depending on the purpose of the amplification.

In specific embodiments, each tag shows no identity with the target nucleic acid molecule. This minimises the possibility of aberrant tag binding. However, this is not an essential feature because it would be extremely unlikely that the primer region would also bind to the target nucleic acid molecule in the same region and thus no productive (in the sense of directing amplification) hybridisation would occur.

The primer pairs of the invention can also be provided in the form of a kit. Thus, in a related aspect, the invention provides a kit for multiplex nucleic acid amplification comprising a set of primers as defined herein.

In particular embodiments, the kit further comprises universal primers for subsequent sequencing, each universal primer comprising, in 5' to 3' order:

a. an adaptor sequence
b. optionally a sample barcode sequence
c. a universal primer region identical (in the 5' to 3' direction) to the universal tag of a corresponding primer used in the multiplex amplification.

The adaptor sequence may be any suitable adaptor sequence for high-throughput nucleic acid sequencing using a next generation sequencing (NGS) platform. Examples of NGS platforms include Illumina sequencing (such as Hi-Seq and Mi-Seq), SMRT sequencing (Pacific Biosciences), Nanopore sequencing, SoLID sequencing, pyrosequencing (e.g. Roche 454) and Ion-Torrent (Thermo Fisher) which are well-known to the skilled person. The adaptor sequence may be complementary to an oligonucleotide immobilised on a suitable solid surface (the nature of which depends on the sequencing platform, such as a flow cell (Illumina), zero mode waveguide (SMRT) or bead (pyrosequencing)) for sequencing. Examples include p5 and p7 adaptors required for sequencing using the Illumina MiSeq or HiSeq platform as well as A and P1 adaptors required for sequencing using the Thermo Fisher Ion Proton platform.

A sample barcode sequence is used to allow sample identification. This is advantageous where multiple samples are being investigated in a single sequencing run. However, this is optional. For some applications, e.g. ultra-deep sequencing of a sample, a sample barcode sequence may be redundant. Where included, the sample barcode sequence may be any suitable sample barcode sequence for high-throughput nucleic acid sequencing using the chosen NGS platform.

The universal primer region identical (in the 5' to 3' direction) to a universal tag incorporated into the amplification products when the primer pairs are used in the multiplex may be DNA- or RNA-based or a combination of both provided that it can act as a primer for a (DNA) polymerase. Preferably, the universal primer region is composed of DNA. The universal primer region may comprise canonical and/or non-canonical nucleotides. Canonical nucleotides include guanine, cytosine, thymine, adenine and uracil. Non-canonical nucleotides include inosine, thiouridine, isoguanine, isocytosine and diaminopyrimidine. Again, universal primers are well known in the art for use in various NGS platforms.

In further embodiments, the kit may further comprise suitable reagents for mPCR including one or more, up to all, of a polymerase, dinucleotide triphosphates (dNTPs), $MgCl_2$ and buffer. Any suitable polymerase may be utilised. Generally, DNA polymerases are used to amplify nucleic acid targets according to the invention. Examples include thermostable polymerases such as Taq or Pfu polymerase and the various derivatives of those enzymes. Suitable buffers are also well known and commercially available and may be included in a PCR mastermix that includes the majority of the components required for PCR amplification.

In further embodiments, the kit may further comprise suitable reagents for reverse transcription of RNA to cDNA including a reverse transcriptase enzyme. Any suitable reverse transcriptase may be utilised. Suitable buffers are also well known and commercially available and may be included in a reverse transcription mastermix that includes the majority of the components required for reverse transcription.

In preferred embodiments, the kit comprises a pair of universal primers. These may be termed first and second universal primers respectively. More specifically, the first universal primer comprises, in 5' to 3' order:

a. a first adaptor sequence (as defined herein)
b. (optionally) a sample barcode sequence (as defined herein)
c. a universal primer region identical (in the 5' to 3' direction) to a first universal tag incorporated into the amplification products when the primer pairs are used in the multiplex amplification;

The second universal primer comprises, in 5' to 3' order:
a. a second adaptor sequence (as defined herein). The second adaptor is generally different from the first adaptor sequence. Typically, the second adaptor sequence shares substantially no or little sequence identity with the first adaptor sequence.
b. (optionally) a sample barcode sequence as defined herein
c. a universal primer region identical (in the 5' to 3' direction) to a second universal tag incorporated into the amplification products when the primer pairs are used in the multiplex amplification.

Amplification using the pair of universal primers as illustrated in FIGS. 6A-C generates desired amplification products which incorporate a first adaptor sequence (and optionally a sample barcode sequence) at one end and a second adaptor sequence (and optionally a sample barcode sequence) at the other end. This enables (immediate) use in high-throughput, massively parallel DNA sequencing. In some preferred embodiments, the first and second adaptor sequences are the p5 and p7 adaptors respectively required for sequencing using the Illumina MiSeq or HiSeq platform. In other equally preferred embodiments, the first and second adaptor sequences are the A and P1 adaptors respectively required for sequencing using the Thermo Fisher Ion Proton platform.

In further embodiments, the universal primers may include a sample barcode as defined herein and as known in the art upstream of the universal primer region but downstream of the adaptor sequence. Thus, in specific embodiments, the/each universal primer comprises, in 5' to 3' order, an adaptor sequence, a sample barcode and a universal primer region.

In a further aspect, the invention also provides a multiplex nucleic acid amplification reaction (e.g. mPCR) comprising amplification of overlapping regions of a target nucleic acid molecule as defined herein using a set of primers as defined herein to create tagged amplification products as defined herein.

In some embodiments, the multiplex nucleic acid amplification reaction further comprises a step of detecting the amplification products. Detection of the amplification products may be by routine methods, such as, for example, gel electrophoresis or may be carried out using real-time or end-point detection methods such as the use of intercalating fluorescent dyes such as SYBR Green I (Sambrook and Russell, Molecular Cloning—A Laboratory Manual, Third edition), the TaqMan® system (Applied Biosystems), see Holland et al; Detection of specific polymerase chain reaction product by utilising the 5'-3' exonuclease activity of *Thermus aquaticus* DNA polymerase; Proc. Natl. Acad. Sci. USA 88, 7276-7280 (1991), Gelmini et al. Quantitative polymerase chain reaction-based homogeneous assay with flurogenic probes to measure C-Erb-2 oncogene amplification. Clin. Chem. 43, 752-758 (1997) and Livak et al. Towards fully automated genome wide polymorphism screening. Nat. Genet. 9, 341-342 (19995) or the Molecular Beacon system, see Tyagi & Kramer. Molecular beacons—probes that fluoresce upon hybridization. Nat. Biotechnol. 14, 303-308 (1996) and Tyagi et al. Multicolor molecular beacons for allele discrimination. Nat. Biotechnol. 16, 49-53 (1998). Other systems such as Scorpion systems and FRET based systems may be adopted as required.

In alternative embodiments, the multiplex nucleic acid amplification reaction further comprises an additional amplification to prepare the tagged amplification products for sequencing, the additional amplification reaction utilising universal primers, each universal primer comprising, in 5' to 3' order:
a. an adaptor sequence as defined herein
b. optionally a sample barcode sequence as defined herein
c. a universal primer region identical (in the 5' to 3' direction) to a universal tag incorporated into the amplification products when the primer pairs are used in the multiplex amplification as defined herein.

Such additional amplification preferably employs the pair of universal primers of the invention.

Adaptor sequences, universal primers and sample barcodes are discussed above, which discussion applies mutatis mutandis and is not repeated for reasons of conciseness.

The invention also encompasses sequencing reactions to detect and/or quantify the target nucleic acid molecules. Such methods comprise an amplification reaction according to the invention followed by sequencing of the amplification products, preferably using a next generation sequencing technique.

Enabling Multistep Amplification Reactions in a Single Reaction Mixture by Controlling the Extent of the First Amplification Reaction The inventors have developed primers used in the first amplification reaction that facilitate performance of multistep, typically two-step, amplifications in a single reaction mixture or vessel. The role of the first primers in the first amplification is to amplify the target sequences of interest and to incorporate universal tags into the amplicons. The tagged amplicons then act as the template for the second amplification, in which universal primers hybridise to the tags and incorporate additional sequences, in particular adapters, needed for further processing and identification purposes. If the multistep amplification is performed in a single reaction mixture or vessel, there is an issue that the first primers will continue to generate product and thus effectively compete with the second amplification reaction. This can lead to generation of aberrant products. There is thus a need to control the extent of the first amplification reaction.

The primers of the invention exploit the ability of RNase H to cleave double stranded DNA sequences which contain a RNA base on one strand. If the RNA base is flanked by, typically at least 4 (although this may depend on the precise RNase H enzyme employed in the amplification; experiments have shown that RNase H2 from *Pyrococcus abyssi* requires a duplex region of at least 4 base pairs 3' to an RNA base), base pairs of double stranded (or "duplex") DNA on either side, the RNase H will cleave the 5' end of the RNA base. Thus, the primers of the invention include a RNA base located at a position such that RNase H is not able to act until the full primer sequence has been incorporated into a double stranded amplification product. Synthesis of the complementary strand corrects the RNA base. Thus, when a further primer of the invention binds to the complementary strand a double stranded sequence is generated containing a RNA base flanked by, typically at least 4 (although this may depend on the precise RNase H enzyme employed in the amplification), base pairs of double stranded (or "duplex") DNA on either side. The RNase H thus cleaves the RNA base. This reaction serves to reduce the efficiency of the first amplification reaction and reduces the proportion of aberrant sequences in the final mixture.

While a double stranded region of 4 base pairs either side is considered a minimum to generate a cleavage event, in particular when using RNase H2 from *Pyrococcus abyssi*, it is possible that other RNase H enzymes may be effective with a shorter region of double stranded DNA either side of the RNA nucleotide. This can be readily tested, for example using the experimental approach set forth in Dobosy J R, Rose S D, Beltz K R, Rupp S M, Powers K M, Behlke M A, and Walder J A (2011) RNase H-dependent PCR (rhPCR): improved specificity and single nucleotide polymorphism detection using blocked cleavable primers. BMC Biotechnol, 11:80; see the experiment described on page 7. It should also be noted that the primer region 3' of the RNA nucleotide needs to hybridise with the target nucleic acid molecule and thus will in practice always be significantly longer than 4 nucleotides. Typically, the primer region will be a minimum of 15 nucleotides generally at least 20 nucleotides.

According to one aspect, the invention provides a primer for use in a multistep amplification of a target nucleic acid molecule, comprising, in 5' to 3' order:
  a. a universal tag
  b. an RNA nucleotide
  c. a primer region that hybridizes with a strand of the target nucleic acid molecule Due to the requirements of RNase H, the target nucleic acid molecule according to this aspect of the invention is DNA. DNA can be generated by reverse transcription of RNA. Thus, the target nucleic acid molecule may comprise genomic DNA or cDNA. The target nucleic acid molecule may be double or single stranded.

The multistep amplification is typically a two-step reaction and preferably occurs in a single reaction mixture or vessel. The first amplification is used to amplify the target nucleic acid molecule and incorporate universal tags into the amplicons. The second amplification is a universal amplification in which the universal tags acts as hybridisation sites for the universal primers that are used to incorporate adapter sequences for further processing and identification purposed. Thus, the primer of the invention is for use in the first step of the multistep amplification.

The primer comprises, in 5' to 3' order:
  a. a universal tag.

The tag is a so-called "universal" tag and is used to incorporate a sequence into the first round amplification products to which second round "universal" primers can hybridise. Thus, the tag sequence is designed so as to be the same as the primer region of the universal primers.

The tag thus does not match the sequence of the initial target nucleic acid molecule. Hybridisation to the initial target nucleic acid molecule is achieved by the separate primer region. Of course, once the tag has been incorporated into the amplification products, the tag sequence then acts as a further hybridisation region for the primer.

It is important that the tag does not comprise RNA nucleotides, so as to prevent unwanted cleavage by RNase H that would impede the second amplification reaction. Typically, therefore, the tag consists of DNA nucleotides. However, any nucleotide that is not susceptible to RNase H activity may be employed, provided that the nucleotide is capable of base pairing with a suitably designed universal primer in the second amplification.
  b. an RNA nucleotide The specific RNA nucleotide is not important. It simply needs to be a nucleotide that can be cleaved by RNase H when present in a double-stranded DNA context. As discussed above, typically, the double stranded DNA context requires a minimum of 4 base pairs of double stranded (or "duplex") DNA bases on either side of the RNA nucleotide. Preferably a single RNA nucleotide is included in the primer. It should also be noted that the RNA nucleotide may, or may not, match the corresponding DNA nucleotide in the target DNA molecule. In either case, the RNA nucleotide is incorporated into the amplification product. Synthesis of the complementary strand corrects the RNA base and includes the corresponding DNA nucleotide. Thus, when a further primer of the invention binds to the complementary strand a double stranded sequence is generated containing a RNA base flanked by, typically at least 4 (although this may depend on the precise RNase H enzyme employed in the amplification), base pairs of double stranded (or "duplex") DNA on either side. The RNase H thus cleaves the RNA base. This reaction serves to reduce the efficiency of the first amplification reaction and reduces the proportion of aberrant sequences in the final mixture.
  c. a primer region that hybridizes with a strand of the target nucleic acid molecule The primer region directs amplification of the target nucleic acid molecule. Again, it is important that the primer region does not comprise RNA nucleotides so as to prevent unwanted cleavage by RNase H that would impede amplification of the target nucleic acid. Typically, therefore, the primer region consists of DNA nucleotides that hybridise to the target DNA sequence. However, any nucleotide that is not susceptible to RNase H activity may be employed, provided that the nucleotide is capable of base pairing with the target nucleic acid sequence. Due to the mechanism of action, in which the RNase H substrate is not generated upon initial primer binding but instead relies upon synthesis of the complementary strand followed by primer binding to the complementary strand, there is freedom in designing the primer region in relation to the target. Thus, within the constraints of primer design to ensure hybridisation with the desired target DNA molecule, mismatches are tolerated and should not adversely impact on the performance of the invention. Primer design against a given target nucleic acid sequence is well within the capabilities of one skilled in the art.

It should be noted that the primer region can, in some embodiments, incorporate the RNA nucleotide. This is with the proviso that primer binding to the initial target DNA molecule does not generate an RNase H substrate. Typically, therefore, the RNA nucleotide cannot be more than 3 nucleotides downstream (in the 5' to 3' direction) of the start of the primer region. This ensures that the RNA nucleotide is not flanked by at least 4 base pairs of double stranded (or "duplex") DNA bases on either side prior to amplification of the initial target nucleic acid molecule. This is shown schematically in FIG. 10.

Typically, apart from the RNA nucleotide, the remaining nucleotides in the primer are DNA nucleotides. However, as already discussed, other non-RNA nucleotides may be employed in the primer provided that they replicate the function of the corresponding DNA nucleotide and are not susceptible to RNase H activity.

Dobosy and colleagues (Dobosy J R, Rose S D, Beltz K R, Rupp S M, Powers K M, Behlke M A, and Walder J A (2011) RNase H-dependent PCR (rhPCR): improved specificity and single nucleotide polymorphism detection using blocked cleavable primers. BMC Biotechnol, 11:80) developed rhPCR. This system relies upon RNase H activity to eliminate primer dimers. It relies on blocked primers that are activated by RNAse H activity. In contrast to this system, the present invention does not require blocked primers. Thus, the primers of the invention do not require a blocking group; in particular do not require a blocking group downstream of the RNA base. Nevertheless, in some embodiments, the primers of the invention may be modified so as to include the functionality first described by Dobosy (see FIG. 1 of Dobosy). This requires a further RNA nucleotide downstream (in the 5' to 3' direction) of the first RNA nucleotide. Thus, in some embodiments, a primer for use in a multistep amplification of a target nucleic acid molecule, comprises, in 5' to 3' order:

a. a universal tag
b. an RNA nucleotide
c. a primer region that hybridizes with a strand of the target nucleic acid molecule
d. a further RNA nucleotide
e. a further region that hybridizes with a strand of the target nucleic acid molecule
f. a blocking group Thus, the primers of the invention may be adapted for use in RNase H-dependent PCR (rhPCR) reactions. This system is particularly advantageous to avoid formation of primer-dimers and other template independent reactions. It depends upon a RNase H substrate being formed upon initial primer binding to the target DNA molecule. The blocked primers are inactive. Upon cleavage by RNase H, the primer region (c) is effectively unblocked and can then prime synthesis of a DNA strand.

The additional features required of such primers are:

d. a further RNA nucleotide

A further cleavage site needs to be introduced into the primer and this needs to be downstream of the primer region. The specific RNA nucleotide is not important. It simply needs to be a nucleotide that can be cleaved by RNase H when present in a double-stranded DNA context. As discussed above, typically, the double stranded DNA context requires a minimum of 4 base pairs of double stranded (or "duplex") DNA bases on either side of the RNA nucleotide. Preferably a single further RNA nucleotide is included in the primer. It should also be noted that the RNA nucleotide preferably matches the corresponding DNA nucleotide in the target DNA molecule. This maximises efficiency of cleavage by RNase H. Thus, when a primer of the invention binds to the target DNA a double stranded sequence is generated containing a RNA base flanked by, typically at least 4 (although this may depend on the precise RNase H enzyme employed in the amplification), base pairs of double stranded (or "duplex") DNA on either side. The RNase H thus cleaves the RNA base and releases the primer region to direct synthesis.

e. a further region that hybridizes with a strand of the target nucleic acid molecule The further region hybridizes with a strand of the target nucleic acid molecule and thus improves specificity for the target DNA molecule compared to use of the primer region only. The further RNA nucleotide and further region hybridize to consecutive DNA bases that follow on from the binding site of the primer region. Because the further region is present to provide the context for RNase H cleavage upon binding to the DNA target, it need only be of sufficient length to provide sufficient base pairs of double stranded (or "duplex") DNA bases on either side of the further RNA nucleotide, in combination with the primer region. Typically, the further region is a minimum of 4 nucleotides in length to generate the relevant context for RNase H mediate cleavage upon target binding. At least the first of these nucleotides preferably matches the target DNA molecule. This is the most important nucleotide to ensure efficient cleavage by RNase H. However, ideally, at least the first 1, 2, 3 or 4 and preferably all nucleotides match the target DNA molecule. This maximises the efficiency of cleavage but is not essential.

While a single further RNA nucleotide is all that is necessary and is thus preferred, additional further RNA nucleotides may be included in the further region which are also cleaved by RNase H. All that is needed is the release of the block of the primer region enabling it to then direct amplification. The further region simply needs to provide the appropriate substrate context for RNase H activity and does not, in itself, perform any further function. Accordingly, multiple cleavage events are possible provided that the cleavage results in removal of the blocking group and permits the primer region to extend the target nucleic acid molecule. Typically, however, the further region consists of DNA nucleotides that hybridise to the target DNA sequence. Nevertheless, any nucleotide that is not susceptible to RNase H activity may be employed, provided that the nucleotide is capable of base pairing with the target nucleic acid sequence.

f. a blocking group

The blocking group prevents unwanted extension prior to cleavage by RNase H (which effectively unblocks the primer region). Any suitable blocking group for this purpose may be employed and the skilled person is well aware of blocking groups that can be used. In certain embodiments the blocking group is selected from the following: 3'ddC, 3' Inverted dT, 3' C3 spacer (such as a C3 propanediol spacer), 3' Amino, and 3' phosphorylation.

The primers of the invention may incorporate additional elements. For example, they may include suitable labels to facilitate monitoring of the amplification and/or detection of amplification products. In preferred embodiments, the primers of the invention further comprise a barcode sequence. Typically, the barcode sequence is positioned downstream of the RNA nucleotide. A preferred barcode sequence is a molecular barcode. In specific embodiments the molecular barcode is at least 4, 6 or 8 nucleotides in length. Generally, the molecular barcode is no more than 20 nucleotides in length.

While a primer of the invention can be used in combination with a "standard" second primer (i.e. a tagged target-specific primer) to form a primer pair, the primers of the invention are advantageously used in pairs in the first amplification. Thus, the invention also provides a primer pair comprising a forward and reverse primer according to the invention for amplifying a target nucleic acid molecule.

A key reagent for practising the invention is RNase H. RNase H's ribonuclease activity cleaves the 3'-O-P bond of RNA in a DNA/RNA duplex substrate to produce 3'-hydroxyl and 5'-phosphate terminated products. The RNase H enzymes useful in the present invention must be active during nucleic acid amplification. The enzyme acts in real-time on the amplification products as the primers hybridise to the template. Thus, since PCR is the most preferred amplification process useful according to the invention, typically the RNase H is a thermostable RNase H. Preferably, such RNase H has significantly lower activity at room temperature than at the elevated temperatures employed during PCR (thermal cycling). However, if an isothermal amplification reaction was performed (e.g. NASBA) a thermostable RNase H may not be essential.

Accordingly, the invention further provides a set of reagents for use in a multistep amplification of a target nucleic acid molecule, comprising a primer or a primer pair of the invention together with RNase H. Preferably the RNase H is thermostable. An RNase H2 may be utilised, such as RNase H2 from *Pyrococcus abyssi*.

The invention provides a multistep (typically two-step) amplification of a target nucleic acid molecule comprising use of a primer, primer pair or a set of reagents of the invention. Such reactions preferably occur in a single reaction mixture or vessel.

The invention also provides a method for amplification of a target nucleic acid molecule comprising amplifying the target nucleic acid molecule in the presence of RNase H using a first primer pair of the invention such that:

a. following the first round of amplification, the target nucleic acid molecule is replicated and a first amplification product incorporates the universal tag and RNA nucleotide of the first forward primer and a second amplification product incorporates the universal tag and RNA nucleotide of the first reverse primer;

b. in the second round of amplification, the first reverse primer hybridizes with the first amplification product to generate a third amplification product incorporating the complement of the universal tag and DNA complement of the RNA nucleotide of the first forward primer and the first forward primer hybridizes with the second amplification product to generate a fourth amplification product incorporating the complement of the universal tag and DNA complement of the RNA nucleotide of the first reverse primer, wherein the third and fourth amplification products each represent a substrate for RNase H activity resulting in cleavage of the RNA nucleotide thereby limiting further amplification of the target nucleic acid molecule.

As referred to above, the first and second rounds of amplification each involve the first forward and first reverse primers of the invention. Thus, this method describes the first amplification reaction. It may, and indeed preferably does, take place in the context of the multistep amplification reactions. Such reactions preferably occur in a single reaction mixture or vessel.

Thus, the methods for amplification may further comprise an additional amplification to prepare the tagged amplification products for sequencing, the additional amplification reaction utilising universal primers, each universal primer comprising, in 5' to 3' order:

a. an adaptor sequence as defined herein b. optionally a sample barcode sequence as defined herein c. a universal primer region identical (in the 5' to 3' direction) to a universal tag incorporated into the amplification products when the primer pairs are used in the multiplex amplification as defined herein.

Such additional amplification preferably employs the pair of universal primers of the invention. More specifically, the first universal primer comprises, in 5' to 3' order:

a. a first adaptor sequence (as defined herein)

b. (optionally) a sample barcode sequence (as defined herein)

c. a universal primer region identical (in the 5' to 3' direction) to a first universal tag incorporated into the amplification products when the primer pairs are used in the multiplex amplification;

The second universal primer comprises, in 5' to 3' order:

a. a second adaptor sequence (as defined herein). The second adaptor is generally different from the first adaptor sequence. Typically, the second adaptor sequence shares substantially no or little sequence identity with the first adaptor sequence.

b. (optionally) a sample barcode sequence as defined herein c. a universal primer region identical (in the 5' to 3' direction) to a second universal tag incorporated into the amplification products when the primer pairs are used in the multiplex amplification.

The invention also encompasses sequencing reactions to detect and/or quantify the target nucleic acid molecules. Such methods comprise an amplification reaction according to the invention followed by sequencing of the amplification products, preferably using a next generation sequencing technique.

The primers, primer pairs and sets of reagents of the invention can also be provided in the form of a kit. Thus, in a related aspect, the invention provides a kit for multistep amplification of a target nucleic acid molecule comprising the primers, primer pairs or sets of reagents as described above.

In particular embodiments, the kit further comprises universal primers for subsequent sequencing, each universal primer comprising, in 5' to 3' order:

a. an adaptor sequence b. optionally a sample barcode sequence c. a universal primer region identical (in the 5' to 3' direction) to the universal tag of a corresponding primer used in the first amplification.

The adaptor sequence may be any suitable adaptor sequence for high-throughput nucleic acid sequencing using a next generation sequencing (NGS) platform. Examples of NGS platforms include Illumina sequencing (such as Hi-Seq and Mi-Seq), SMRT sequencing (Pacific Biosciences), Nanopore sequencing, SoLID sequencing, pyrosequencing (e.g. Roche 454) and Ion-Torrent (Thermo Fisher) which are well-known to the skilled person. The adaptor sequence may be complementary to an oligonucleotide immobilised on a suitable solid surface (the nature of which depends on the sequencing platform, such as a flow cell (Illumina), zero mode waveguide (SMRT) or bead (pyrosequencing)) for sequencing. Examples include p5 and p7 adaptors required for sequencing using the Illumina MiSeq or HiSeq platform as well as A and P1 adaptors required for sequencing using the Thermo Fisher Ion Proton platform.

A sample barcode sequence is used to allow sample identification. This is advantageous where multiple samples are being investigated in a single sequencing run. However, this is optional. For some applications, e.g. ultra-deep sequencing of a sample, a sample barcode sequence may be redundant. Where included, the sample barcode sequence may be any suitable sample barcode sequence for high-throughput nucleic acid sequencing using the chosen NGS platform.

The universal primer region identical (in the 5' to 3' direction) to a universal tag incorporated into the amplification products when the primer pairs are used in the first amplification may be DNA- or RNA-based or a combination of both provided that it can act as a primer for a (DNA) polymerase. Preferably, the universal primer region is composed of DNA. The universal primer region may comprise canonical and/or non-canonical nucleotides. Canonical nucleotides include guanine, cytosine, thymine, adenine and uracil. Non-canonical nucleotides include inosine, thiouridine, isoguanine, isocytosine and diaminopyrimidine. Again, universal primers are well known in the art for use in various NGS platforms.

In preferred embodiments, the kit comprises a pair of universal primers. These may be termed first and second universal primers respectively. More specifically, the first universal primer comprises, in 5' to 3' order:
  a. a first adaptor sequence (as defined herein)
  b. (optionally) a sample barcode sequence (as defined herein)
  c. a universal primer region identical (in the 5' to 3' direction) to a first universal tag incorporated into the amplification products when the primer pairs are used in the multiplex amplification;

The second universal primer comprises, in 5' to 3' order:
  a. a second adaptor sequence (as defined herein). The second adaptor is generally different from the first adaptor sequence. Typically, the second adaptor sequence shares substantially no or little sequence identity with the first adaptor sequence.
  b. (optionally) a sample barcode sequence as defined herein
  c. a universal primer region identical (in the 5' to 3' direction) to a second universal tag incorporated into the amplification products when the primer pairs are used in the multiplex amplification.

In further embodiments, the universal primers may include a sample barcode as defined herein and as known in the art upstream of the universal primer region but downstream of the adaptor sequence. Thus, in specific embodiments, the/each universal primer comprises, in 5' to 3' order, an adaptor sequence, a sample barcode and a universal primer region.

In further embodiments, the kit may further comprise suitable reagents for PCR including one or more, up to all, of a polymerase, dinucleotide triphosphates (dNTPs), MgCl$_2$ and buffer. Any suitable polymerase may be utilised. Generally, DNA polymerases are used to amplify nucleic acid targets according to the invention. Examples include thermostable polymerases such as Taq or Pfu polymerase and the various derivatives of those enzymes. Suitable buffers are also well known and commercially available and may be included in a PCR mastermix that includes the majority of the components required for PCR amplification.

In further embodiments, the kit may further comprise suitable reagents for reverse transcription of RNA to cDNA including a reverse transcriptase enzyme. Any suitable reverse transcriptase may be utilised. Suitable buffers are also well known and commercially available and may be included in a reverse transcription mastermix that includes the majority of the components required for reverse transcription.

The kits may further comprise reagents for subsequent sequencing.

The kits may comprise instructions for use. Such instructions may be included as package insert inside the kit.

Enabling Multistep Amplification Reactions in a Single Reaction Mixture by Delaying Production of the Universal Primers The inventors have developed improved reagents for performing multistep, in particular at least two-step, amplification (especially PCR) of a target nucleic acid molecule. In particular, the inventors provide a set of reagents for performing a multistep nucleic acid amplification assay in a single reaction vessel. This removes the requirement to perform each step of a multi-step amplification reaction in separate reaction vessels. The reagents are used to generate the universal primers simultaneously with the first amplification of the target nucleic acid. Thus, according to the invention an amplification reaction is needed in order to generate the universal primers. This creates a delay in generating the universal primers, relative to the first amplification of the target nucleic acid. This delay enables generation of a sufficient quantity of the products of the first amplification reaction (namely tagged amplicons) to act as a substrate for the universal primers. This in turn helps to reduce non-specific interactions, which would be prevalent if the universal primers were simply added at the start of the reaction.

Thus, in a first aspect, the invention provides a set of reagents for use in a multistep amplification of a target nucleic acid molecule, comprising:
  a. a first primer pair designed to amplify the target nucleic acid molecule, comprising:
    i. a first forward primer incorporating a primer region that hybridizes with a strand of the target nucleic acid molecule and a first universal tag 5' of the primer region
    ii. a first reverse primer incorporating a primer region that hybridizes with a strand of the target nucleic acid molecule and a second universal tag 5' of the primer region
  b. a first nucleic acid molecule comprising in 5' to 3' order:
    i. a sequence of nucleotides that is the reverse complement of the first universal tag
    ii. a sequence of nucleotides that is the reverse complement of a first adapter sequence needed for subsequent processing
    iii. a blocking group preventing extension beyond the adapter sequence.
  c. a second nucleic acid molecule comprising in 5' to 3' order:
    i. a sequence of nucleotides that is the reverse complement of the second universal tag
    ii. a sequence of nucleotides that is the reverse complement of a second adapter sequence needed for subsequent processing
    iii. a blocking group preventing extension beyond the second adapter sequence
  d. a first adapter primer that hybridizes with the reverse complement of the first adapter sequence to generate an amplification product comprising in 5' to 3' order:
    i. the first adapter sequence
    ii. the first universal tag
  e. a second adapter primer that hybridizes with the reverse complement of the second adapter sequence to generate an amplification product comprising in 5' to 3' order:
    i. the second adapter sequence
    ii. the second universal tag wherein the amplification products generated using the first and second adapter primers of d and e form a universal primer pair in which the first and second universal tags act as primers to amplify amplification products generated by the first primer pair to produce further amplification products incorporating the first and second universal tags and adapters.

The first and second nucleic acid molecules thus represent the reverse compliment of universal primer sequences that form a universal primer pair. The use of the first and second nucleic acid molecules with the first and second adapter primers adds in a temporal delay to the production of the universal primer pair that amplifies the amplification products generated by the first primer pair. This allows for sufficient amplification of the target nucleic acid molecule using the first (target-specific) primer pair to generate an excess of the substrate for the universal primer pair. This reduces the non-specific effects that would otherwise result from attempting to carry out a multistep amplification in a single reaction vessel.

The first primer pair that amplifies the target molecule does not need to be modified compared to the tagged target-specific primer pairs currently in use (see FIG. 1 for an illustration of the prior art system for carrying out a multistep amplification). Thus, there is also provided a set of reagents for use in a multistep amplification of a target nucleic acid molecule, comprising:

a. a first nucleic acid molecule comprising in 5' to 3' order:
 i. a sequence of nucleotides that is the reverse complement of a first universal tag incorporated in a forward primer of a first primer pair that hybridizes with a strand of the target nucleic acid molecule
 ii. a sequence of nucleotides that is the reverse complement of a first adapter sequence needed for subsequent processing
 iii. a blocking group preventing extension beyond the first adapter sequence.
b. a second nucleic acid molecule comprising in 5' to 3' order:
 i. a sequence of nucleotides that is the reverse complement of a second universal tag incorporated in a reverse primer of the first primer pair that hybridizes with a strand of the target nucleic acid molecule
 ii. a sequence of nucleotides that is the reverse complement of a second adapter sequence needed for subsequent processing
 iii. a blocking group preventing extension beyond the second adapter sequence
c. a first adapter primer that hybridizes with the reverse complement of the first adapter sequence to generate an amplification product comprising in 5' to 3' order:
 i. the first adapter sequence
 ii. the first universal tag
d. a second adapter primer that hybridizes with the reverse complement of the second adapter sequence to generate an amplification product comprising in 5' to 3' order:
 i. the second adapter sequence
 ii. the second universal tag
wherein the amplification products generated using the first and second adapter primers of c and d form a universal primer pair in which the first and second universal tags act as primers to amplify amplification products generated by the first primer pair to produce further amplification products incorporating the first and second universal tags and adapters.

However, in preferred embodiments, primers of the invention are used together with these (reverse complement) nucleic acid molecules. The (sets of) reagents described herein are thus suitable for use in a multistep amplification of a target nucleic acid molecule that is performed in a single reaction mixture.

According to a related aspect of the invention there is provided a method for multistep amplification of a target nucleic acid molecule, comprising:

a. amplifying the target nucleic acid molecule using a first primer pair, comprising:
 i. a first forward primer incorporating a primer region that hybridizes with a strand of the target nucleic acid molecule and a first universal tag 5' of the primer region
 ii. a first reverse primer incorporating a primer region that hybridizes with a strand of the target nucleic acid molecule and a second universal tag 5' of the primer region to produce first amplification products incorporating the first universal tag and the second universal tag
b. amplifying a first nucleic acid molecule comprising in 5' to 3' order:
 i. a sequence of nucleotides that is the reverse complement of the first universal tag
 ii. a sequence of nucleotides that is the reverse complement of a first adapter sequence needed for subsequent processing
 iii. a blocking group preventing extension beyond the first adapter sequence
using a first adapter primer that hybridizes with the reverse complement of the first adapter sequence to generate an amplification product comprising in 5' to 3' order:
 i. the first adapter sequence
 ii. the first universal tag
c. amplifying a second nucleic acid molecule comprising in 5' to 3' order:
 i. a sequence of nucleotides that is the reverse complement of the second universal tag
 ii. a sequence of nucleotides that is the reverse complement of a second adapter sequence needed for subsequent processing
 iii. a blocking group preventing extension beyond the second adapter sequence
using a second adapter primer that hybridizes with the reverse complement of the second adapter sequence to generate an amplification product comprising in 5' to 3' order:
 i. the second adapter sequence
 ii. the second universal tag
d. amplifying the amplification products generated by the first primer pair using the amplification products of steps b and c as a universal primer pair in which the first and second universal tags act as primers to produce further amplification products incorporating the first and second universal tags and functional sequences, wherein the method is performed in a single reaction mixture.

For the avoidance of doubt, methods of the invention encompass the performance of additional steps after the generation of the further amplification products (i.e. after the universal amplification). Such methods are not constrained to the same reaction mixture of reaction vessel. Such methods typically involve detecting the target nucleic acid molecule. In preferred embodiments, the methods of the invention are used to identify and optionally quantify specific target nucleic acid molecules. In preferred embodiments the method further comprises sequencing the further amplification products. Sequencing is typically performed in massively parallel fashion. Preferably, sequencing is performed using a next generation sequencing (NGS) technique. The sequencing may take place in a different reaction mixture to that of steps a to d.

Thus, the invention provides a method for detecting and optionally quantifying a target nucleic acid molecule, comprising:

a multistep amplification of the target nucleic acid molecule which comprises:
a. amplifying the target nucleic acid molecule using a first primer pair, comprising:
 i. a first forward primer incorporating a primer region that hybridizes with a strand of the target nucleic acid molecule and a first universal tag 5' of the primer region ii. a first reverse primer incorporating a primer region that hybridizes with a strand of the target nucleic acid molecule and a second universal tag 5' of the primer region
to produce first amplification products incorporating the first universal tag and the second universal tag
b. amplifying a first nucleic acid molecule comprising in 5' to 3' order:
iii. a sequence of nucleotides that is the reverse complement of the first universal tag
iv. a sequence of nucleotides that is the reverse complement of a first adapter sequence needed for subsequent processing
v. a blocking group preventing extension beyond the first adapter sequence
using a first adapter primer that hybridizes with the reverse complement of the first adapter sequence to generate an amplification product comprising in 5' to 3' order:
iii. the first adapter sequence
iv. the first universal tag
c. amplifying a second nucleic acid molecule comprising in 5' to 3' order:
vi. a sequence of nucleotides that is the reverse complement of the second universal tag
vii. a sequence of nucleotides that is the reverse complement of a second adapter sequence needed for subsequent processing
viii. a blocking group preventing extension beyond the second adapter sequence
using a second adapter primer that hybridizes with the reverse complement of the second adapter sequence to generate an amplification product comprising in 5' to 3' order:
iii. the second adapter sequence
iv. the second universal tag
d. amplifying the amplification products generated by the first primer pair using the amplification products of steps b and c as a universal primer pair in which the first and second universal tags act as primers to produce further amplification products incorporating the first and second universal tags and functional sequences, wherein the method is performed in a single reaction mixture; and
sequencing the further amplification products, preferably using a next generation sequencing technique.

Prior to sequencing, the further amplification products may be purified. The sequencing may, depending upon the technique chosen, comprise further amplification of the further amplification products for signal generation purposes (as would be readily understood by the skilled person). Such further amplification may be may any suitable technique such as bridge amplification or bead-based amplification (emulsion PCR). Examples of NGS platforms useful according to the present invention include Illumina sequencing (such as Hi-Seq and Mi-Seq), SMRT sequencing (Pacific Biosciences), Nanopore sequencing, SoLID sequencing, pyrosequencing (e.g. Roche 454), single molecule sequencing (SeqLL/Helicos) and Ion-Torrent (Thermo Fisher) which are well-known to the skilled person.

Many sequencing technologies utilise barcode sequences for the purposes of sample identification. Accordingly, in all aspects of the invention, the first nucleic acid molecule may further comprise a sequence of nucleotides that is the reverse complement of a first barcode sequence, typically a first sample barcode. Thus, in preferred embodiments, the first nucleic acid molecule comprises in 5' to 3' order:

i. a sequence of nucleotides that is the reverse complement of the first universal tag
ii. a sequence of nucleotides that is the reverse complement of a first sample barcode
iii. a sequence of nucleotides that is the reverse complement of a first adapter sequence needed for subsequent processing
iv. a blocking group preventing extension beyond the adapter sequence In embodiments where the first nucleic acid molecule further comprises a sequence of nucleotides that is the reverse complement of a first barcode sequence, typically a first sample barcode, the first adapter primer hybridizes with the reverse complement of the first adapter sequence to generate an amplification product comprising the first adapter sequence, the first barcode sequence and the first universal tag. In preferred embodiments where the first nucleic acid molecule further comprises a sequence of nucleotides that is the reverse complement of a first sample barcode, the first adapter primer hybridizes with the reverse complement of the first adapter sequence to generate an amplification product comprising in 5' to 3' order:

i. the first adapter sequence
ii. the first sample barcode
iii. the first universal tag The amplification product acts as a universal primer and forms a universal primer pair with the amplification product generated using the second adaptor primer to produce further amplification products incorporating the first and second universal tags, first barcode sequence, in particular sample barcode, and first and second adapters.

According to all aspects of the invention, the second nucleic acid molecule may further comprise a sequence of nucleotides that is the reverse complement of a second barcode sequence, typically a second sample barcode. Thus, in preferred embodiments, the second nucleic acid molecule comprises in 5' to 3' order:

i. a sequence of nucleotides that is the reverse complement of the second universal tag
ii. a sequence of nucleotides that is the reverse complement of a second sample barcode
iii. a sequence of nucleotides that is the reverse complement of a second adapter sequence needed for subsequent processing
iv. a blocking group preventing extension beyond the adapter sequence In embodiments where the second nucleic acid molecule further comprises a sequence of nucleotides that is the reverse complement of a second barcode sequence, typically a second sample barcode, the second adapter primer hybridizes with the reverse complement of the second adapter sequence to generate an amplification product comprising the second adapter sequence, the second barcode sequence and the second universal tag. In preferred embodiments where the second nucleic acid molecule further comprises a sequence of nucleotides that is the reverse complement of a second sample barcode, the second adapter primer hybridizes with the reverse complement of the second adapter sequence to generate an amplification product comprising in 5' to 3' order:

i. the second adapter sequence
ii. the second sample barcode
iii. the second universal tag This amplification product acts as a universal primer and forms a universal primer pair with the amplification product generated using the first adaptor primer to produce further amplification products incorporating the first and second universal tags, second barcode sequence, in particular second sample barcode, and first and second adapters.

In specific embodiments both the first and second nucleic acid molecules further comprise sequences of nucleotides that are the reverse complement of a barcode sequence, typically a sample barcode. In these embodiments the further amplification products incorporate first and second universal tags, first and second barcode sequences, preferably sample barcodes and first and second adapters.

Thus, one key contribution of the invention is the provision of reverse compliment sequences corresponding to a universal primer. The reverse compliment sequences are blocked at the 3' end to prevent unwanted amplification. Accordingly, in a related aspect the invention provides a nucleic acid molecule comprising in 5' to 3' order:

a. a sequence of nucleotides that is the reverse complement of a tag
  b. optionally a sequence of nucleotides that is the reverse complement of a barcode sequence, preferably sample barcode
  c. a sequence of nucleotides that is the reverse complement of an adapter sequence needed for subsequent processing
  d. a blocking group preventing extension beyond the adapter sequence.

Typically such molecules are provided in pairs, to form a universal primer pair. Thus, the invention provides a combination of a first nucleic acid molecule comprising in 5' to 3' order:

a. a sequence of nucleotides that is the reverse complement of a first universal tag
  b. optionally a sequence of nucleotides that is the reverse complement of a barcode sequence, preferably a sample barcode
  c. a sequence of nucleotides that is the reverse complement of a first adapter sequence needed for subsequent processing
  d. a blocking group preventing extension beyond the first adapter sequence;

together with a second nucleic acid molecule comprising in 5' to 3' order:

a. a sequence of nucleotides that is the reverse complement of a second universal tag
  b. optionally a sequence of nucleotides that is the reverse complement of a barcode sequence, preferably a sample barcode
  c. a sequence of nucleotides that is the reverse complement of a second adapter sequence needed for subsequent processing
  d. a blocking group preventing extension beyond the second adapter sequence.

Specific reverse compliment sequences corresponding to a universal primer that are used according to the invention comprise, consist essentially of or consist of the nucleotide sequence of any one of SEQ ID Nos 5-24.

Each universal primer is generated using a primer that hybridizes with the reverse compliment of the adapter sequence. Thus, the combination of universal primer and adapter primer forms a further aspect of the invention. In particular there is provided a combination of the universal primer reverse compliment nucleic acid molecule with a primer that hybridizes with the reverse complement of the adapter sequence to generate an amplification product comprising in 5' to 3' order:

a. the adapter sequence needed for subsequent processing
  b. optionally the barcode sequence, preferably a sample barcode
  c. the tag Preferred combinations are of first and second nucleic acid molecules that represent the reverse compliment of a universal primer pair with respective first and second adapter primers. In particular there is provided a combination of the universal primer reverse compliment nucleic acid molecules that form a universal primer pair with:

a first adapter primer that hybridizes with the reverse complement of the first adapter sequence to generate an amplification product comprising in 5' to 3' order:

a. the first adapter sequence needed for subsequent processing
  b. optionally the first barcode sequence, preferably a sample barcode
  c. the first universal tag a second adapter primer that hybridizes with the reverse complement of the second adapter sequence to generate an amplification product comprising in 5' to 3' order:

a. the second adapter sequence needed for subsequent processing
  b. optionally the second barcode sequence, preferably a sample barcode
  c. the second universal tag Specific adaptor primers useful according to the invention comprise, consist essentially of or consist of the nucleotide sequence of SEQ ID No 3 and/or 4.

According to a related aspect of the invention there is provided a multistep nucleic acid amplification reaction comprising amplification of a target nucleic acid molecule using a set of reagents as defined above to create amplification products incorporating tags and adapter sequences.

The set of reagents of the invention can also be provided in the form of a kit. Thus, in a related aspect, the invention provides a kit for multistep amplification of a target nucleic acid molecule comprising the set of reagents, nucleic acid molecule or combination as described above.

In further embodiments, the kit may further comprise suitable reagents for PCR including one or more, up to all, of a polymerase, dinucleotide triphosphates (dNTPs), $MgCl_2$ and buffer. Any suitable polymerase may be utilised. Generally, DNA polymerases are used to amplify nucleic acid targets according to the invention. Examples include thermostable polymerases such as Taq or Pfu polymerase and the various derivatives of those enzymes.

Suitable buffers are also well known and commercially available and may be included in a PCR mastermix that includes the majority of the components required for PCR amplification.

In further embodiments, the kit may further comprise suitable reagents for reverse transcription of RNA to cDNA including a reverse transcriptase enzyme. Any suitable reverse transcriptase may be utilised. Suitable buffers are also well known and commercially available and may be included in a reverse transcription mastermix that includes the majority of the components required for reverse transcription.

The kits may further comprise reagents for subsequent sequencing.

The kits may comprise instructions for use. Such instructions may be included as package insert inside the kit.

Improving Multiplex Amplifications Involving Overlapping Target Sequences and Enabling Multistep Amplification Reactions in a Single Reaction Mixture by Controlling the Extent of the First Amplification Reaction In preferred embodiments, primers of the invention are used in the first amplification reaction in multiplex to amplify overlapping regions of a target nucleic acid molecule. Those primers advantageously produce tagged amplification products that can then be amplified in a second amplification reaction (generally PCR). The invention also provides primers that control the extent of the first amplification reaction, to minimise competition with the second reaction and prevent excessive production of aberrant amplification products. The features of these primers can be included in the primers of the invention designed to amplify overlapping regions of a target nucleic acid molecule.

Thus, for example, in a set of primers for use in multiplex amplification of overlapping regions of a target nucleic acid molecule, comprising:
a. at least two primer pairs designed to amplify overlapping regions of the target nucleic acid molecule, each primer pair comprising:
 i. a forward primer incorporating a primer region that hybridizes with a strand of the target nucleic acid molecule and a universal tag 5' of the primer region
 ii. a reverse primer incorporating a primer region that hybridizes with a strand of the target nucleic acid molecule and a universal tag 5' of the primer region, wherein the universal tag of the forward and reverse primer in each primer pair are different, the universal tags of the forward and reverse primer in immediately neighbouring primer pairs are identical in the 5' to 3' direction such that, in the event that an aberrant amplification product is formed between the forward and reverse primers of immediately neighbouring primer pairs, an intramolecular hybridization event occurs between the nucleic acid tag at the 5' end of the aberrant amplification product and the complementary sequence at the 3' end of the aberrant amplification product formed during amplification to form a secondary structure that precludes further amplification of the aberrant amplification product;
the primers may also comprise, in 5' to 3' order:
a. an RNA nucleotide downstream of the universal tag
b. a primer region that does not comprise RNA nucleotides and that hybridizes with a strand of the target nucleic acid molecule.

In such embodiments, the universal tags do not comprise RNA nucleotides.

All further embodiments of each relevant aspect apply mutatis mutandis and are not repeated for reasons of conciseness. For example, a pair of universal primers as defined herein may be included in a set of reagents for multiplex and multistep amplification.

Such sets of primers can be used in multiplex and multistep amplifications as discussed herein. They can be included in kits as discussed herein. They can be included in reaction vessels as discussed herein; one key advantage is the fact that a single reaction can take place in the same reaction mixture.

Following the second amplification reaction, the amplification products include adapters and optionally barcodes that enable downstream processing and identification. Ideally this is by NGS, as discussed herein, to enable identification and/or quantification of the target nucleic acid.

Improving Multiplex Amplifications Involving Overlapping Target Sequences and Enabling Multistep Amplification Reactions in a Single Reaction Mixture by Delaying Production of the Universal Primers In preferred embodiments, primers of the invention are used in the first amplification reaction in multiplex to amplify overlapping regions of a target nucleic acid molecule. Those primers advantageously produce tagged amplification products that can then be amplified in a second amplification reaction (generally PCR). The invention also provides nucleic acid molecules, forming the reverse compliment of a universal primer that are useful to delay production of the universal primers needed for the second amplification reaction. This is useful to control the start of the second amplification reaction, until sufficient products from the first amplification reaction (tagged amplicons) are generated to which the universal primers hybridise. These reagents can be advantageously combined to amplify overlapping regions of a target nucleic acid molecule and ensure efficient second stage amplification.

Thus, for example, in a set of reagents for use in a multistep amplification of a target nucleic acid molecule, comprising:
a. a first primer pair designed to amplify the target nucleic acid molecule, comprising:
 i. a first forward primer incorporating a primer region that hybridizes with a strand of the target nucleic acid molecule and a first universal tag 5' of the primer region
 ii. a first reverse primer incorporating a primer region that hybridizes with a strand of the target nucleic acid molecule and a second universal tag 5' of the primer region
b. a first nucleic acid molecule comprising in 5' to 3' order:
 i. a sequence of nucleotides that is the reverse complement of the first universal tag
 ii. a sequence of nucleotides that is the reverse complement of a first adapter sequence needed for subsequent processing
 iii. a blocking group preventing extension beyond the adapter sequence.
c. a second nucleic acid molecule comprising in 5' to 3' order:
 i. a sequence of nucleotides that is the reverse complement of the second universal tag
 ii. a sequence of nucleotides that is the reverse complement of a second adapter sequence needed for subsequent processing
 iii. a blocking group preventing extension beyond the second adapter sequence
d. a first adapter primer that hybridizes with the reverse complement of the first adapter sequence to generate an amplification product comprising in 5' to 3' order:
 i. the first adapter sequence
 ii. the first universal tag
e. a second adapter primer that hybridizes with the reverse complement of the second adapter sequence to generate an amplification product comprising in 5' to 3' order:
 i. the second adapter sequence
 ii. the second universal tag
wherein the amplification products generated using the first and second adapter primers of d and e form a universal primer pair in which the first and second universal tags act as primers to amplify amplification products generated by the first primer pair to produce further amplification products incorporating the first and second universal tags and adapters;

multiple overlapping regions of the target nucleic acid molecule may be amplified using at least two primer pairs that amplify the overlapping regions. In such aspects, advantageously, the reagents include a set of primers for use in multiplex amplification of overlapping regions of a target nucleic acid molecule, comprising:

a. a first primer pair designed to amplify a first region of the target nucleic acid molecule, comprising:
   i. a first forward primer incorporating a primer region that hybridizes with a strand of the target nucleic acid molecule
   ii. a first reverse primer incorporating a primer region that hybridizes with a strand of the target nucleic acid molecule and a nucleic acid tag 5' of the primer region
b. a second primer pair designed to amplify a second region of the target nucleic acid molecule that at least partially overlaps with the first region, comprising:
   i. a second forward primer incorporating a primer region that hybridizes with a strand of the target nucleic acid molecule and a nucleic acid tag 5' of the primer region which is identical in the 5' to 3' direction with the nucleic acid tag incorporated at the 5' end of the first reverse primer
   ii. a second reverse primer incorporating a primer region that hybridizes with a strand of the target nucleic acid molecule,
wherein, in the event that an aberrant (short) amplification product is formed between the first reverse primer and second forward primer, an intramolecular hybridization event occurs between the nucleic acid tag at the 5' end of the aberrant (short) amplification product and the complementary sequence at the 3' end of the aberrant (short) amplification product formed during amplification to form a secondary structure that precludes further amplification of the aberrant amplification product.

Even more preferably, the reagents include a set of primers for use in multiplex amplification of overlapping regions of a target nucleic acid molecule, comprising:

a. at least two primer pairs designed to amplify overlapping regions of the target nucleic acid molecule, each primer pair comprising:
   i. a forward primer incorporating a primer region that hybridizes with a strand of the target nucleic acid molecule and a universal tag 5' of the primer region
   ii. a reverse primer incorporating a primer region that hybridizes with a strand of the target nucleic acid molecule and a universal tag 5' of the primer region,
wherein the universal tag of the forward and reverse primer in each primer pair are different, the universal tag of the forward and reverse primer in immediately neighbouring primer pairs are identical in the 5' to 3' direction such that, in the event that an aberrant amplification product is formed between the forward and reverse primers of immediately neighbouring primer pairs, an intramolecular hybridization event occurs between the universal tag at the 5' end of the aberrant amplification product and the complementary sequence at the 3' end of the aberrant amplification product formed during amplification to form a secondary structure that precludes further amplification of the aberrant amplification product.

All further embodiments of each relevant aspect apply mutatis mutandis and are not repeated for reasons of conciseness.

In some embodiments, at least one primer in each primer pair includes a barcode, optionally a molecular barcode. In other embodiments, each primer for amplifying the target nucleic acid molecule includes a barcode, optionally a molecular barcode.

Such sets of reagents, including primers, can be used in multiplex and multistep amplifications as discussed herein. They can be included in kits as discussed herein. They can be included in reaction vessels as discussed herein; one key advantage is the fact that the entire (multiplex and multistep) reaction can take place in the same reaction mixture.

Following the second amplification reaction, the amplification products include adapters and optionally barcodes that enable downstream processing and identification. Ideally this is by NGS, as discussed herein, to enable identification and/or quantification of the target nucleic acid.

Enabling Multistep Amplification Reactions in a Single Reaction Mixture by Delaying Production of the Universal Primers and by Controlling the Extent of the First Amplification Reaction The balance between the first and second amplification reactions is a key obstacle to performing both reactions in a single reaction mixture or vessel. Two complementary solutions to this problem are provided, which can advantageously be combined.

Thus, for example, in a set of reagents for use in a multistep amplification of a target nucleic acid molecule, comprising:

a. a first primer pair designed to amplify the target nucleic acid molecule, comprising:
   i. a first forward primer incorporating a primer region that hybridizes with a strand of the target nucleic acid molecule and a first universal tag 5' of the primer region
   ii. a first reverse primer incorporating a primer region that hybridizes with a strand of the target nucleic acid molecule and a second universal tag 5' of the primer region
b. a first nucleic acid molecule comprising in 5' to 3' order:
   i. a sequence of nucleotides that is the reverse complement of the first universal tag
   ii. a sequence of nucleotides that is the reverse complement of a first adapter sequence needed for subsequent processing
   iii. a blocking group preventing extension beyond the adapter sequence.
c. a second nucleic acid molecule comprising in 5' to 3' order:
   i. a sequence of nucleotides that is the reverse complement of the second universal tag
   ii. a sequence of nucleotides that is the reverse complement of a second adapter sequence needed for subsequent processing
   iii. a blocking group preventing extension beyond the second adapter sequence
d. a first adapter primer that hybridizes with the reverse complement of the first adapter sequence to generate an amplification product comprising in 5' to 3' order:
   i. the first adapter sequence
   ii. the first universal tag
e. a second adapter primer that hybridizes with the reverse complement of the second adapter sequence to generate an amplification product comprising in 5' to 3' order:
   i. the second adapter sequence
   ii. the second universal tag
wherein the amplification products generated using the first and second adapter primers of d and e form a universal primer pair in which the first and second universal tags act as primers to amplify amplification products generated by the first primer pair to produce further amplification products incorporating the first and second universal tags and adapters;

at least one, and preferably both, of the first forward and first reverse primer is a primer for use in a multistep amplification of a target nucleic acid molecule, comprising, in 5' to 3' order:

a. a universal tag that does not comprise RNA nucleotides
b. an RNA nucleotide
c. a primer region that does not comprise RNA nucleotides and that hybridizes with a strand of the target nucleic acid molecule.

All further embodiments of each relevant aspect apply mutatis mutandis and are not repeated for reasons of conciseness.

Thus, RNase H (and preferably a thermostable RNase H) can be added to the reaction mixture. This combination of reagents both controls the extent of the first amplification reaction and delays the start of the second amplification reaction. This facilitates performance of both amplification reactions in a single reaction mixture or vessel, which is highly advantageous.

Such sets of reagents, including primers, can be used in multiplex and multistep amplifications as discussed herein. They can be included in kits as discussed herein. They can be included in reaction vessels as discussed herein; one key advantage is the fact that the entire (multistep) reaction can take place in the same reaction mixture.

Following the second amplification reaction, the amplification products include adapters and optionally barcodes that enable downstream processing and identification. Ideally this is by NGS, as discussed herein, to enable identification and/or quantification of the target nucleic acid.

Improving Multiplex Amplifications Involving Overlapping Target Sequences and Enabling Multistep Amplification Reactions in a Single Reaction Mixture by Controlling the Extent of the First Amplification Reaction, Enabling Multistep Amplification Reactions in a Single Reaction Mixture by Delaying Production of the Universal Primers and by Controlling the Extent of the First Amplification Reaction Most preferably, primers of the invention are used in the first amplification reaction in multiplex to amplify overlapping regions of a target nucleic acid molecule. Those primers advantageously produce tagged amplification products that can then be amplified in a second amplification reaction (generally PCR). The invention also provides primers that incorporate a RNA nucleotide and control the extent of the first amplification reaction, to minimise competition with the second reaction and prevent excessive production of aberrant amplification products. The features of these primers can be included in the primers of the invention designed to amplify overlapping regions of a target nucleic acid molecule.

Such first stage primers can advantageously be combined with nucleic acid molecules, forming the reverse compliment of a universal primer, and preferably a universal primer pair, that are useful to delay production of the universal primers needed for the second amplification reaction. This is useful to control the start of the second amplification reaction, until sufficient products from the first amplification reaction (tagged amplicons) are generated to which the universal primers hybridise. These reagents can be advantageously combined to amplify overlapping regions of a target nucleic acid molecule and ensure efficient second stage amplification.

Such sets of reagents, including primers, can be used in multiplex and multistep amplifications as discussed herein. They can be included in kits as discussed herein. They can be included in reaction vessels as discussed herein; one key advantage is the fact that the entire (multiplex and multistep) reaction can take place in the same reaction mixture.

Following the second amplification reaction, the amplification products include adapters and optionally barcodes that enable downstream processing and identification. Ideally this is by NGS, as discussed herein, to enable identification and/or quantification of the target nucleic acid.

All relevant embodiments of each relevant aspect apply mutatis mutandis and are not repeated for reasons of conciseness.

DESCRIPTION OF THE FIGURES

FIG. 17—Fragment analysis results showing on the X-axis the length of the amplicons and on the Y-axis the yield of each amplicon which is presented as the height of each peak.

FIG. 18—Fragment analysis results showing on the X-axis the length of the amplicons and on the Y-axis the yield of each amplicon which is presented as the height of each peak.

DETAILED DESCRIPTION

Improving Multiplex Amplifications Involving Overlapping Target Sequences

Figure 1:
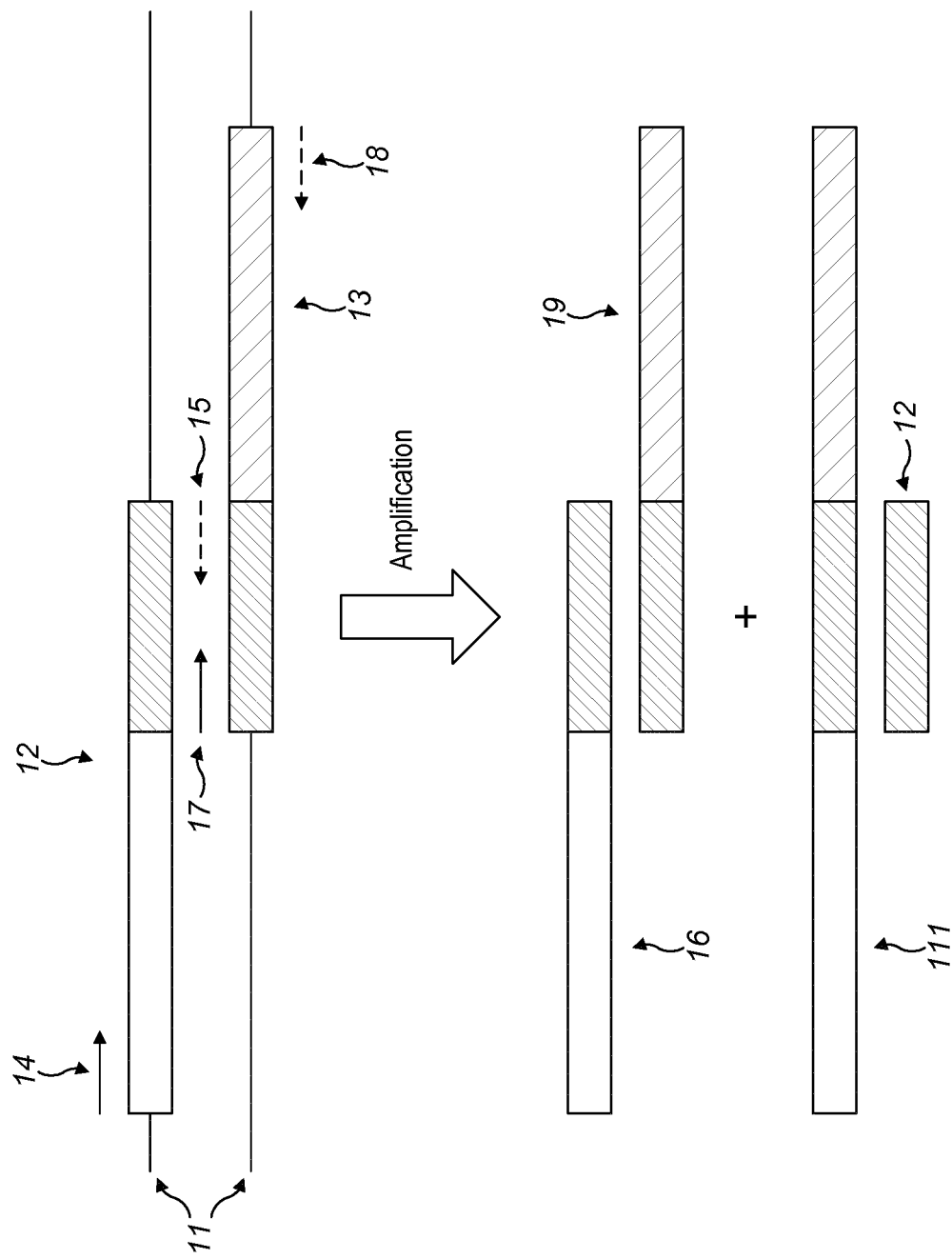
FIG. 1—A schematic representation of the problem associated with the production of aberrant amplification products in a multiplex PCR reaction wherein the amplicons share a region of overlap.

FIG. 1 shows the problem associated with the production of aberrant amplification products in a multiplex PCR reaction wherein the amplicons share a region of overlap. Here is shown, by way of example, a DNA duplex strand (11) containing two target sequences to be amplified: target sequence 1 (TS1; 12) and target sequence 2 (TS2; 13). Each respective target sequence is shown independently for the convenience of the reader but it should be understood that both of these sequences are, in fact, present on, and overlap on, the same DNA duplex strand. The region of overlap is shown as a dotted box. A forward primer (14) and reverse primer (15) are designed to amplify TS1 to produce amplicon 1 (AM1; 16). A second forward primer (17) and second reverse primer (18) are designed to amplify TS2 to produce amplicon 2 (AM2; 19). During amplification, the mechanism of which is well known in the art, both AM1 and AM2 are generated as expected. However, due to the target sequences overlapping on the DNA duplex strand, aberrant amplification products are also produced as shown. A "long" aberrant amplification product 1 (AB1; 111) is formed due to TS1 forward primer (14) acting in concert with TS2 reverse primer (18). A "short" aberrant amplification product 2 (AB2; 112) is formed due to TS2 forward primer (17) acting in concert with TS1 reverse primer (15). AB2, being the shortest amplicon, may be preferentially formed.

Figure 2:
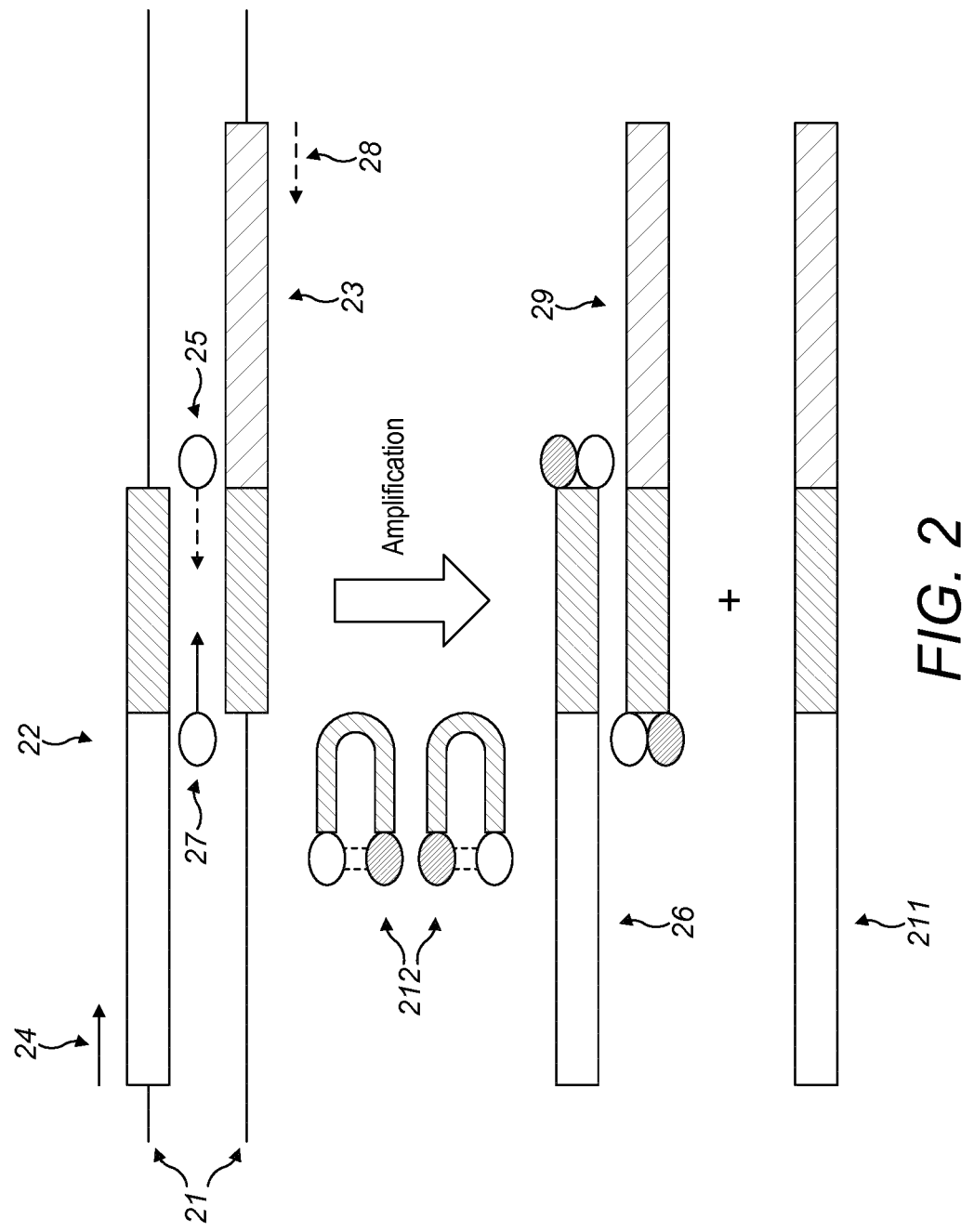
FIG. 2—A schematic representation of the use of sets of primers of the invention to preclude amplification of the short aberrant amplification product.

FIG. 2 illustrates how the use of a set of primers according to the invention helps to overcome the problem illustrated in FIG. 1. Thus, FIG. 2 shows a DNA duplex strand (21) containing two target sequences to be amplified: target sequence 1 (TS1; 22) and target sequence 2 (TS2; 23). Each respective target sequence is shown independently for the convenience of the reader but it should be understood that both of these sequences are, in fact, present on, and overlap on, the same DNA duplex strand (21). The region of overlap is shown as a dotted box. A first forward primer (24) and first reverse primer (25) are designed to amplify TS1 to produce amplicon 1 (AM1; 26) i.e. the first forward primer (24) comprises a primer region (solid arrow) that hybridizes with the anti-sense strand of the DNA duplex strand (21) and the first reverse primer (25) comprises a primer region (dashed arrow) that hybridizes with the sense strand of the DNA duplex strand (21) at the respective boundaries of TS1. A second forward primer (27) and second reverse primer (28) are designed to amplify TS2 to produce amplicon 2 (AM2; 29). Thus, the second forward primer (27) comprises a primer region (solid arrow) that hybridizes with the anti-sense strand of the DNA duplex strand (21) and the second reverse primer (28) comprises a primer region (dashed arrow) that hybridizes with the sense strand of the DNA duplex strand (21) defining the respective boundaries of TS2.

According to the invention, first reverse primer (25) and second forward primer (27) are each tagged at their respective 5' end with identical nucleotide sequences (white circles; hereinafter referred to as the 'tags). For the avoidance of doubt, the sequences are identical in the 5' to 3' direction. The tags do not hybridise with the initial DNA duplex strand (21) prior to amplification.

During mPCR amplification of at least three cycles (one amplification cycle being one sequence of a denaturing step followed by an annealing step followed by an extension step), the mechanism of which is well known in the art, both AM1 and AM2 are generated as expected; AM1 being produced due to the first (TS1) forward primer (24) acting in concert with the first (TS1) reverse primer (25) and AM2 being produced due to the second (TS2) forward primer (27) acting in concert with the second (TS2) reverse primer (28). Importantly, however, the short aberrant amplification product that would otherwise be formed exponentially using conventional, non-tagged primers in place of the second (TS2) forward primer (27) and first (TS1) reverse primer (25) does not accumulate to any significant degree. This is because when the short aberrant amplification product is formed each single strand comprises at its 5' end the nucleic acid tag and at its 3' end the complement of the nucleic acid tag (represented by the black circle). This enables an intramolecular hybridization event to occur between the nucleic acid tag and its complement to form a secondary hairpin-like structure (212) that precludes further amplification of the aberrant amplification product. More specifically, the aberrant amplification product is formed during an amplification cycle and is then heated to a sufficient degree to dissociate (melt) into single nucleic acid strands. During the next amplification cycle, when the temperature is lowered during the annealing step, hybridisation of the 5' nucleic acid tag and its complement sequence at the 3' end of the single-stranded aberrant amplification product is entropically favoured over intermolecular hybridisation of the single-stranded aberrant amplification product with a further primer. Thus, further amplification of the short aberrant amplification product is precluded. As a consequence, the efficiency of amplification of AM1 and AM2 is improved.

In this example, the long aberrant amplification product (211) may still form due to the first (TS1) forward primer (24) acting in concert with the second (TS2) reverse primer (28). However, the production of AM1 and AM2 is nevertheless preferred due to their shorter length.

Figure 3A:
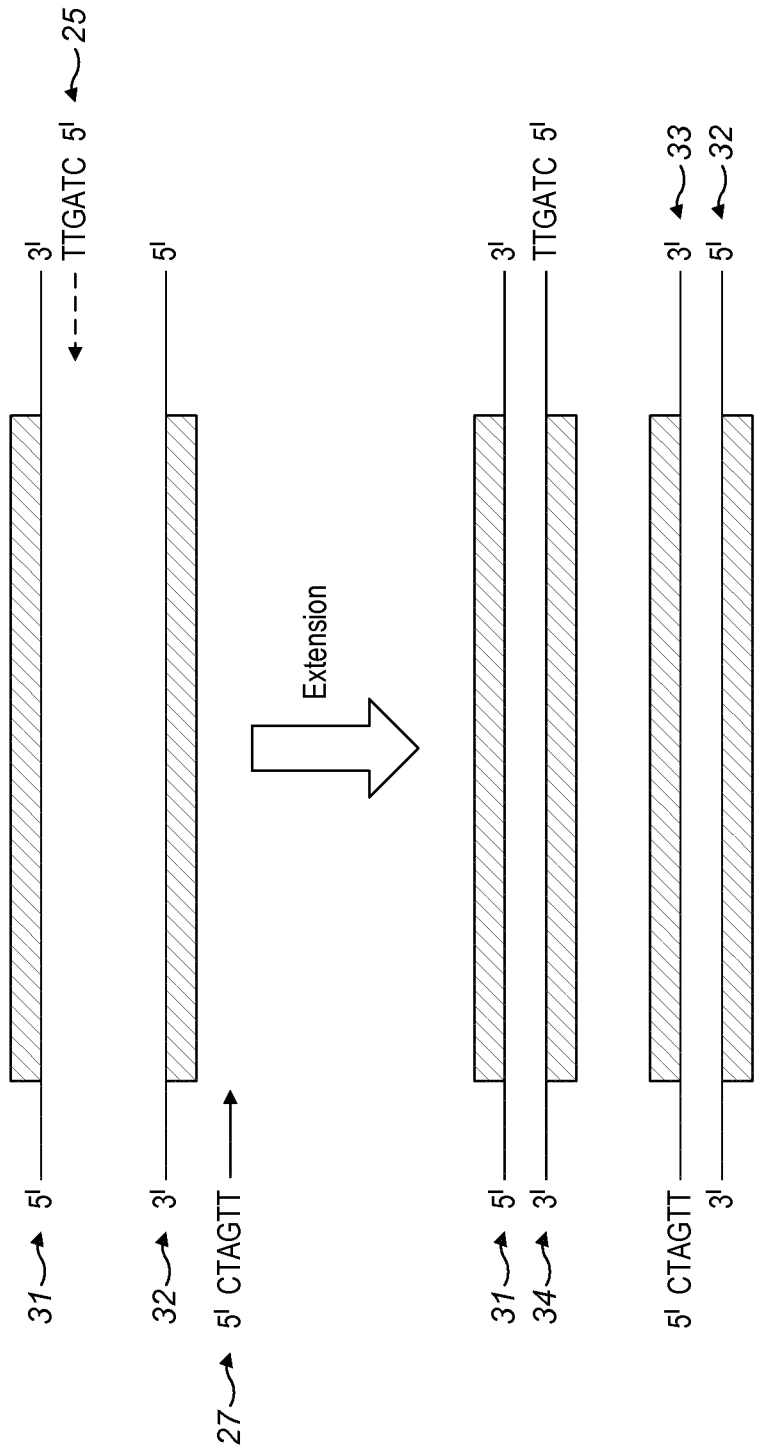
FIG. 3A-C—A schematic representation of three rounds of mPCR using the sets of primers of the invention to demonstrate how a hairpin-like secondary structure is formed to preclude amplification of the short aberrant amplification product.
Figure 3B:
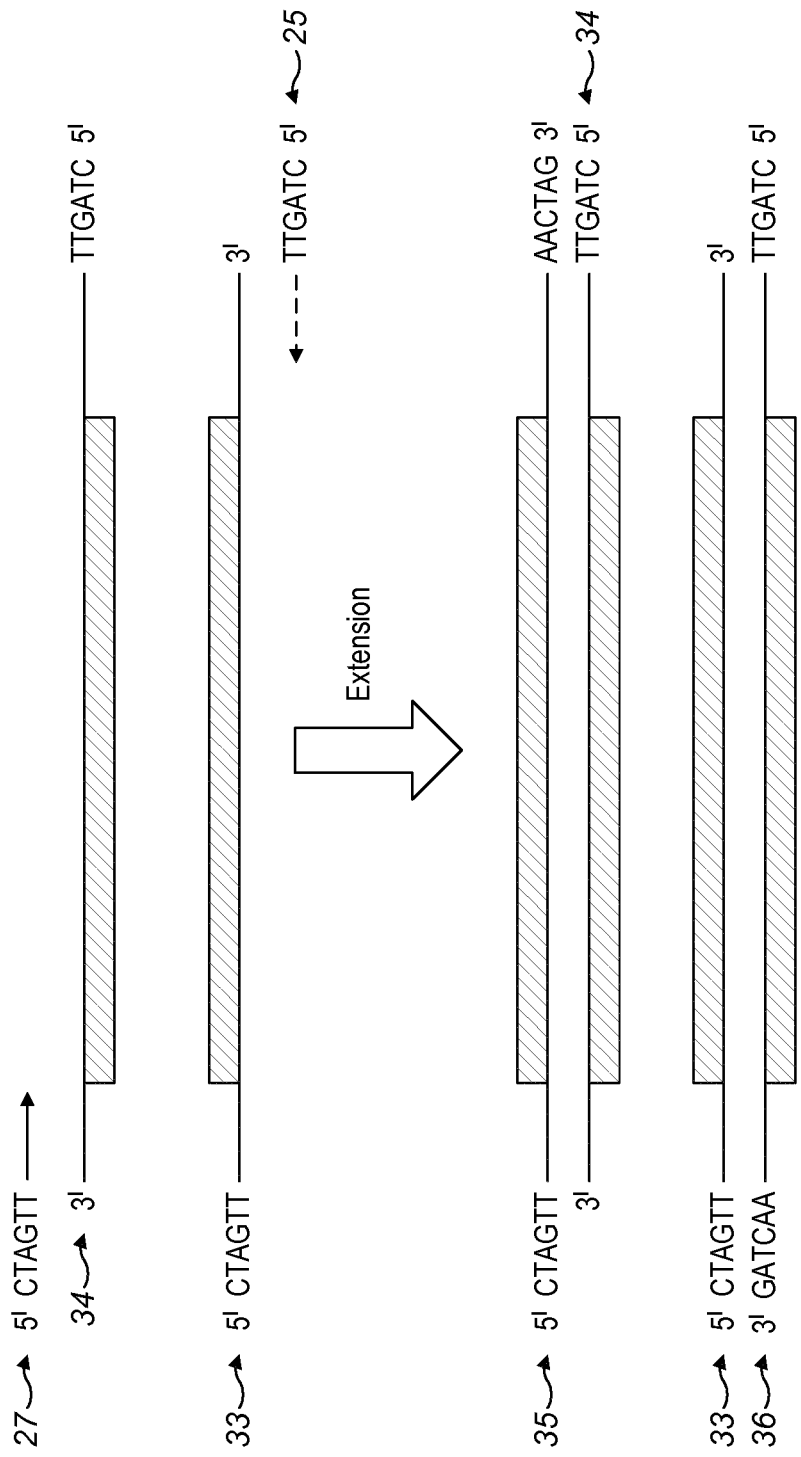
Figure 3C:
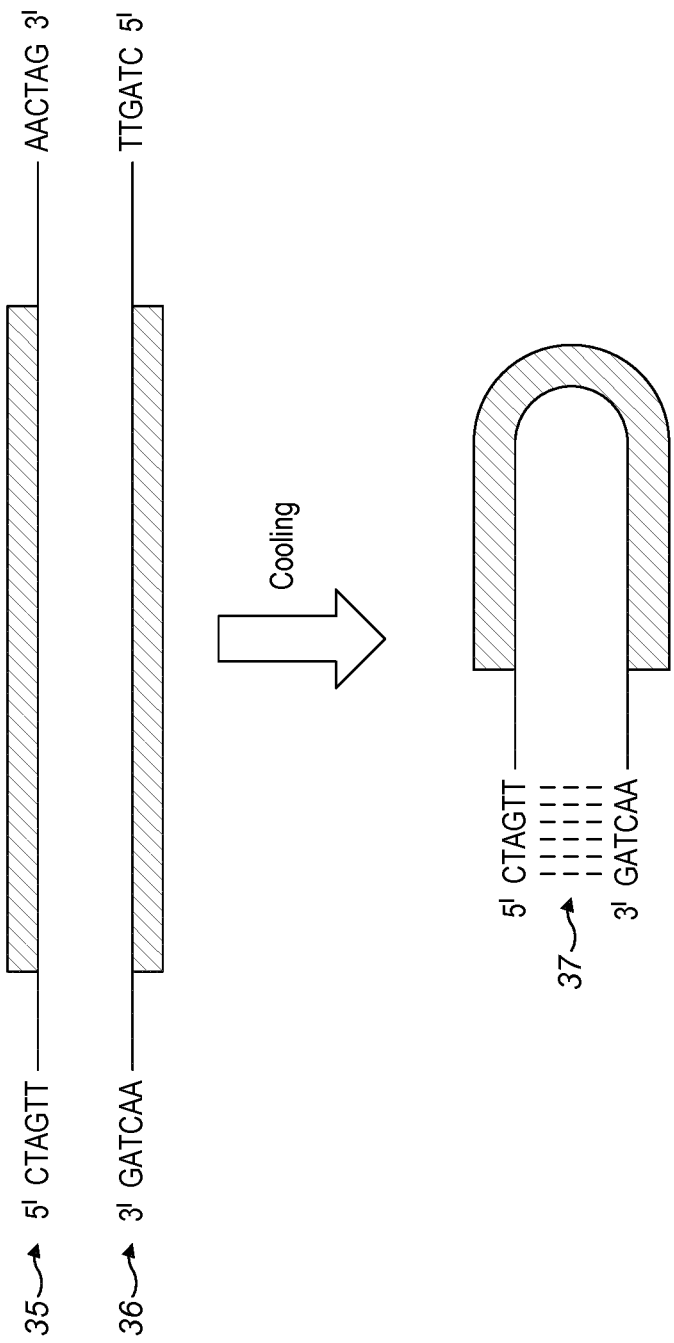

Formation of the secondary hairpin-like structure from the short aberrant amplification product is shown in more detail in FIGS. 3A-C. As shown in FIG. 3A, during a first round of mPCR, the DNA duplex of the initial target nucleic acid molecule has been denatured (or melted) to separate the sense (31) and antisense (32) strands. Cooling during the annealing step means that the second (TS2) forward primer (27) has hybridised to the antisense stand (32) of the target nucleic acid molecule via its complementary primer region (solid arrow). The first (TS1) reverse primer (25) has hybridised to the sense stand (31) of the target nucleic acid molecule via its complementary primer region (dashed arrow). Both the second (TS2) forward primer (27) and the first (TS1) reverse primer (25) comprise a nucleic acid tag at their respective 5' ends; the nucleic acid tag is shown, by way of illustration only, as the nucleotide sequence CTAGTT (5' to 3'). Extension from each hybridised primer by DNA polymerase in the 5' to 3' direction results in synthesis of a new sense (33) and antisense (34) strand which incorporate at their respective 5' ends the CTAGTT tag.

As shown in FIG. 3B, in the second round of mPCR, the double stranded DNA duplexes formed after amplification round 1 are denatured (or melted) to separate the sense and antisense strands. For brevity, only the new sense (33) and antisense (34) strands which incorporate at their respective 5' ends the CTAGTT tag are shown. Following denaturation, cooling during the annealing step means that the second (TS2) forward primer (27) hybridises to the antisense stand (34) via its complementary primer region (solid arrow). The first (TS1) reverse primer (25) hybridises to the sense stand (33) via its complementary primer region (dashed arrow). Extension from each hybridised primer by DNA polymerase results in synthesis of another new sense (35) and antisense (36) strand respectively. At their respective 5' ends the new sense (35) and antisense (36) strand comprise the CTAGTT sequence. At their respective 3' ends the new sense (35) and antisense (36) strand comprise the complementary AACTAG sequence (in the 5' to 3' direction) by virtue of the mechanism of replication via the DNA polymerase.

As shown now in FIG. 3C, in the third round of mPCR, the double stranded DNA duplexes formed after amplification round 2 are denatured (or melted) to separate the sense and antisense strands. Following denaturation and upon cooling during the annealing step, the complementary 5' and 3' tagged ends of the new sense strand (35) and new antisense strand (36) hybridise (37) to form a folded, or hairpin-like, structure. This intramolecular hybridisation event is entropically favoured over intermolecular hybridisation with a further primer and, as a consequence, is preferentially formed. Thus, the primers will now preferentially bind to target nucleic acid molecules, thereby improving the mPCR process.

Figure 4:
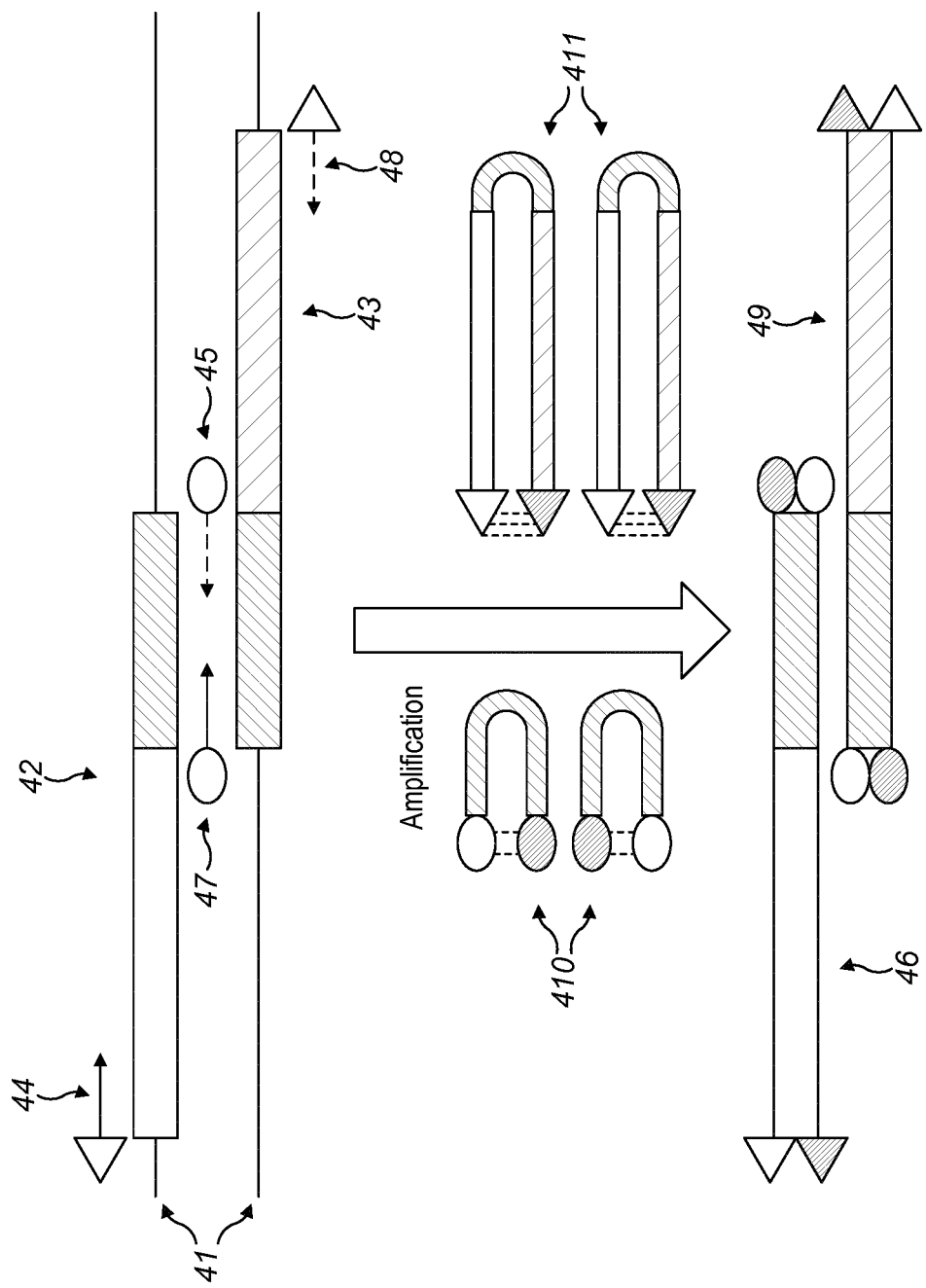
FIG. 4—A schematic representation of the use of two sets of primers of the invention to preclude amplification of both the short and long aberrant amplification products.

In a further example, FIG. 4 illustrates how the use of particularly preferred sets of primers according to the invention prevents the exponential amplification of both the short and long aberrant amplification products in favour of the desired amplification products. It can be readily envisaged how such sets of primers can be increased in number to amplify several overlapping regions in a single reaction vessel.

Thus, FIG. 4 shows a DNA duplex strand (41) containing two target sequences to be amplified: target sequence 1 (TS1; 42) and target sequence 2 (TS2; 43). Each respective target sequence is shown independently for the convenience of the reader but it should be understood that both of these sequences are, in fact, present on, and overlap on, the same DNA duplex strand (41). The region of overlap is shown as a dotted box. A first forward primer (44) and first reverse primer (45) are designed to amplify TS1 to produce amplicon 1 (AM1; 46) i.e. the forward primer (44) comprises a primer region (solid arrow) that hybridizes with the anti-sense strand of the DNA duplex strand (41) and the reverse primer (45) comprises a primer region (dashed arrow) that hybridizes with the sense strand of the DNA duplex strand (41) at the respective boundaries of TS1. A second forward primer (47) and second reverse primer (48) are designed to amplify TS2 to produce amplicon 2 (AM2; 49) i.e. the forward primer (47) comprises a primer region (solid arrow) that hybridizes with the anti-sense strand of the DNA duplex strand (41) and the reverse primer (48) comprises a primer region (dashed arrow) that hybridizes with the sense strand of the DNA duplex strand (41) at the respective boundaries of TS2.

Crucially, first reverse primer (45) and second forward primer (47) are tagged at the 5' end of each primer with identical nucleotide sequences (white circles; hereinafter referred to as lag set 1'). For the avoidance of doubt, the sequences are identical in the 5' to 3' direction. The tags of set 1 do not hybridise with the initial target DNA duplex strand (41). In addition, first forward primer (44) and second reverse primer (48) are tagged at the 5' end of each primer with identical nucleotide sequences which are of a different sequence to those of tag set 1 (white triangles; hereinafter referred to as lag set 2'). For the avoidance of doubt, the sequences are identical in the 5' to 3' direction. The tags set 2 also do not hybridise with the initial target DNA duplex strand (41).

During mPCR amplification of at least three rounds (one round of amplification being one sequence of a denaturing step followed by an annealing step followed by an extension step), the mechanism of which is well known in the art, both AM1 and AM2 are generated as expected; AM1 being produced due to the first (TS1) forward primer (44) acting in concert with the first (TS1) reverse primer (45) and AM2 being produced due to the second (TS2) forward primer (47) acting in concert with the second (TS2) reverse primer (48). Importantly, however, both the short and long aberrant amplification products that would otherwise be formed exponentially using conventional, non-tagged primers do not accumulate to any significant degree. This is because when the short aberrant amplification product is formed each single strand comprises at its 5' end the nucleic acid tag of tag set 1 and at its 3' end the complement of the nucleic acid tag (represented as black circles). This enables an intramolecular hybridization event to occur between the nucleic acid tag and its complement to form a secondary hairpin-like structure (410) that precludes further amplification of the short aberrant amplification product as previously described. Similarly, when the long aberrant amplification product is formed each single strand comprises at its 5' end the nucleic acid tag of tag set 2 and at its 3' end the complement of the nucleic acid tag (represented as black triangles). This enables an intramolecular hybridization event to occur between the nucleic acid tag and its complement to form a secondary hairpin-like structure (411) that precludes further amplification of the long aberrant amplification product as previously described. As a consequence, the efficiency of amplification of AM1 and AM2 is improved. This design is particularly beneficial for mPCR of multiple overlapping regions of a target nucleic acid in a single reaction vessel because the reciprocal arrangement of tags in neighbouring primer pairs frustrates all aberrant amplification production.

Figure 5A:
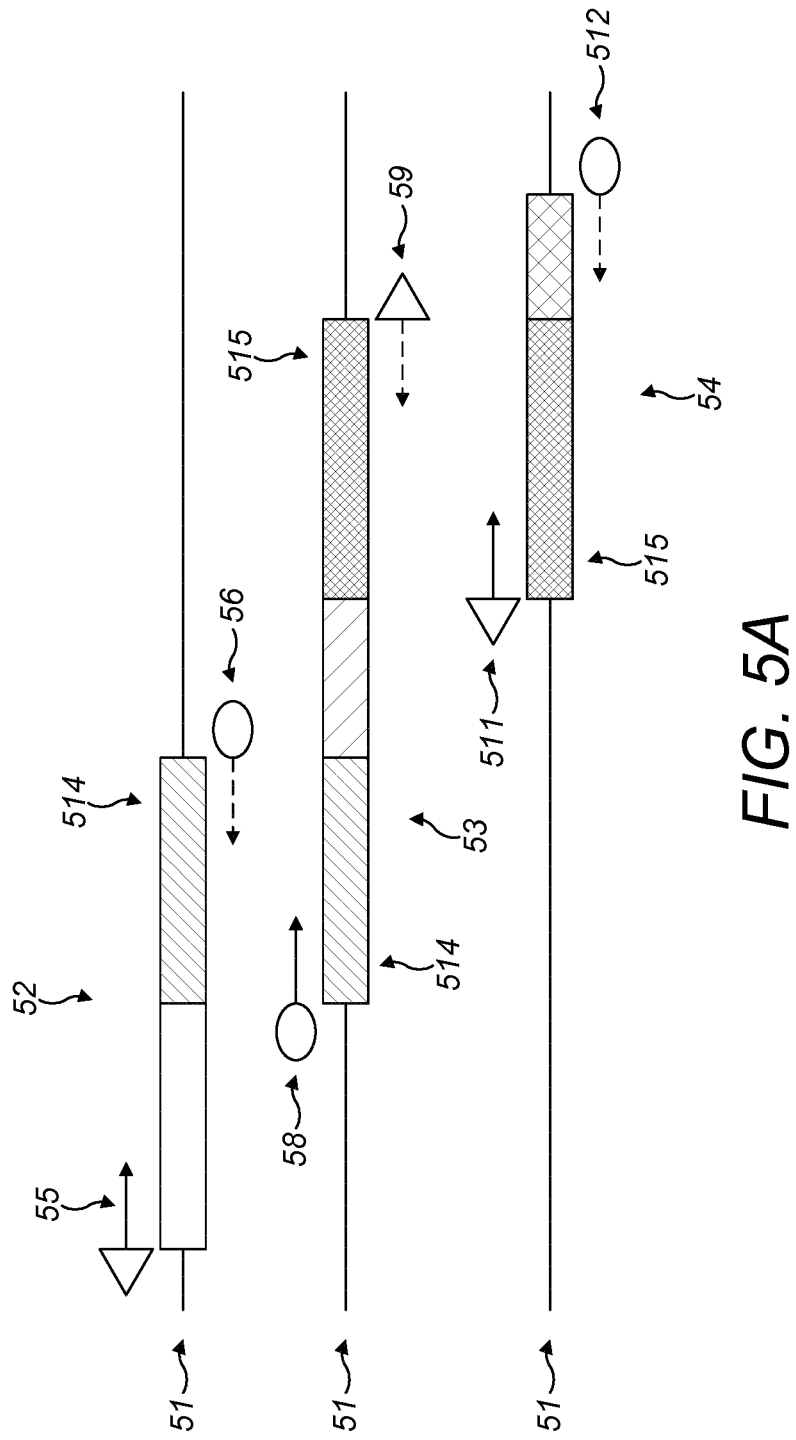
FIG. 5A-C—A schematic representation of the use of three sets of primers of the invention to preclude amplification of substantially all of the short and long aberrant amplification products.
Figure 5B:
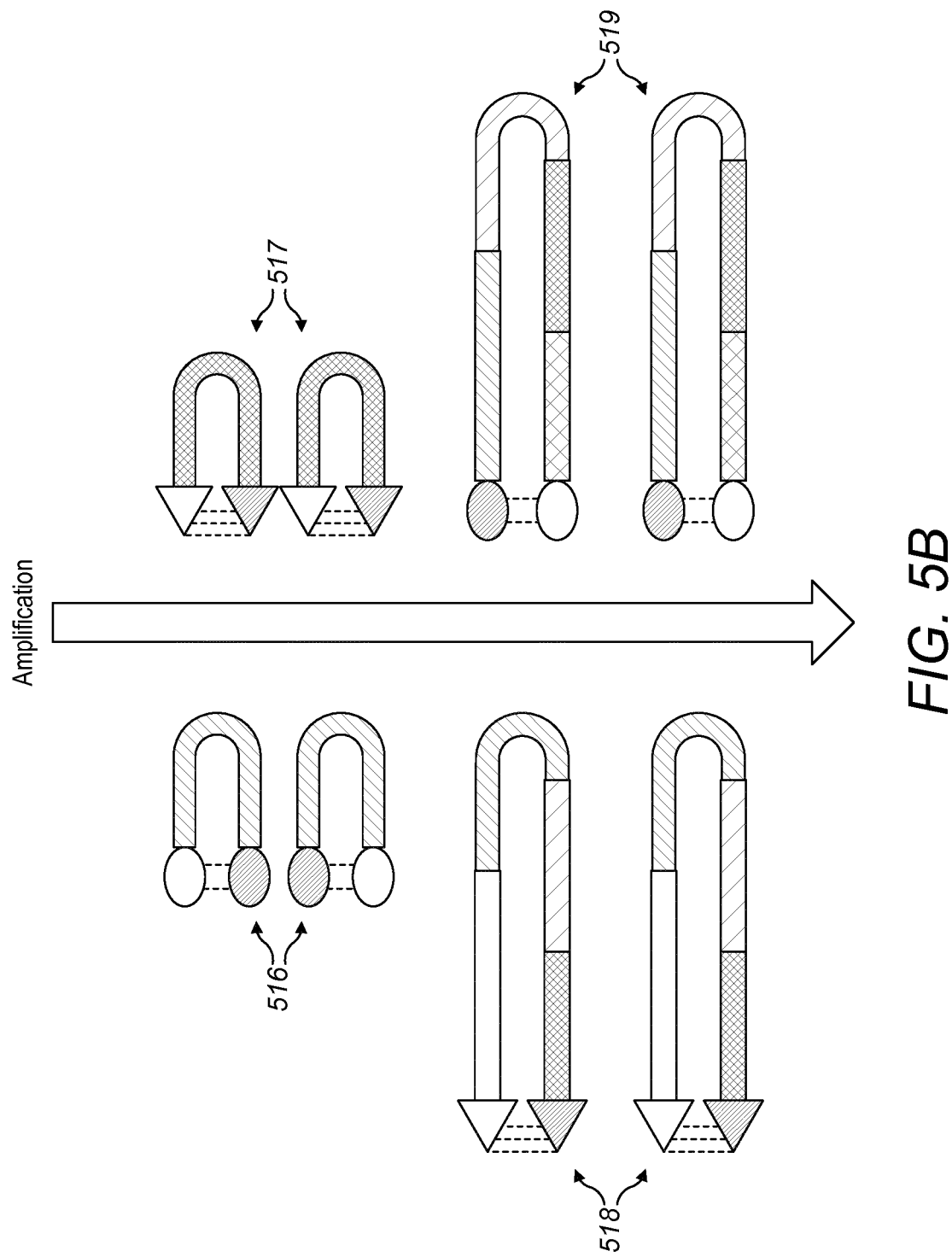
Figure 5C:
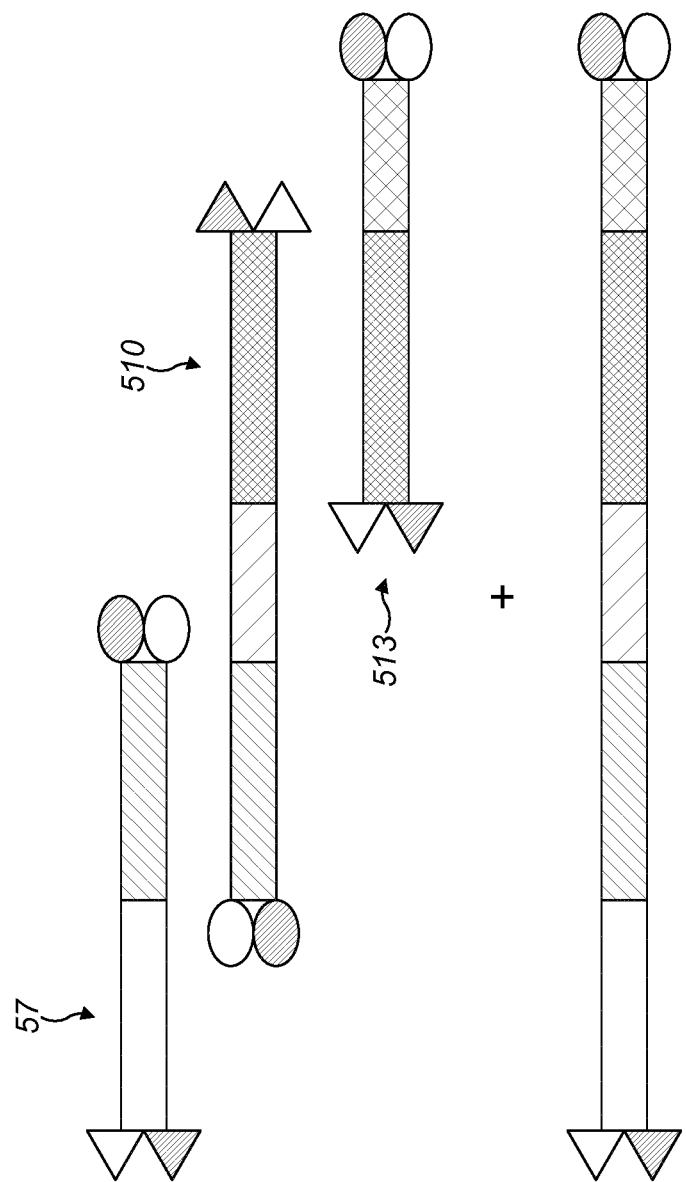

In a further example, FIGS. 5A-C illustrate how the use of particularly preferred sets of primers according to the invention prevents the exponential amplification of substantially all short and long aberrant amplification products in favour of the desired amplification products with respect to three overlapping target regions of the target nucleic acid molecule. It can be readily envisaged how such sets of primers can be further increased in number to amplify four or more (including hundreds or thousands of) overlapping regions in a single reaction vessel.

Thus, FIG. 5A shows a DNA duplex strand (51) containing three target sequences to be amplified: target sequence 1 (TS1; 52), target sequence 2 (TS2; 53) and target sequence 3 (TS3; 54). Each respective target sequence is shown independently for the convenience of the reader but it should be understood that all of these sequences are, in fact, present on the same DNA duplex strand (51). TS1 (52) and TS2 (53) share a region of overlap shown as a dotted box (514). TS2 (53) and TS3 (54) share a region of overlap shown as a chequered box (515).

A first forward primer (55) and first reverse primer (56) are designed to amplify TS1 (52) to produce amplicon 1 (AM1; 57) shown in FIG. 5C i.e. the forward primer (55) comprises a primer region (solid arrow) that hybridizes with the anti-sense strand of the DNA duplex strand (51) and the reverse primer (56) comprises a primer region (dashed arrow) that hybridizes with the sense strand of the DNA duplex strand (51) at the respective boundaries of TS1 (52). A second forward primer (58) and second reverse primer (59) are designed to amplify TS2 (53) to produce amplicon 2 (AM2; 510) shown in FIG. 5C i.e. the forward primer (58) comprises a primer region (solid arrow) that hybridizes with the anti-sense strand of the DNA duplex strand (51) and the reverse primer (59) comprises a primer region (dashed arrow) that hybridizes with the sense strand of the DNA duplex strand (51) at the respective boundaries of TS2 (53). A third forward primer (511) and second reverse primer (512) are designed to amplify TS3 (54) to produce amplicon 2 (AM3; 513) shown in FIG. 5C i.e. the forward primer (511) comprises a primer region (solid arrow) that hybridizes with the anti-sense strand of the DNA duplex strand (51) and the reverse primer (512) comprises a primer region (dashed arrow) that hybridizes with the sense strand of the DNA duplex strand (51) at the respective boundaries of TS3 (54).

Crucially, first reverse primer (56) and second forward primer (58) are tagged at the 5' end of each primer with identical nucleotide sequences (white circles; hereinafter referred to as lag set 1'). For the avoidance of doubt, the sequences are identical in the 5' to 3' direction. The tags of set 1 do not hybridise with the initial target DNA duplex strand (51). In addition, first forward primer (55) and second reverse primer (59) are tagged at the 5' end of each primer with identical nucleotide sequences which are of a different sequence to those of tag set 1 (white triangles; hereinafter referred to as lag set 2'). For the avoidance of doubt, the sequences are identical in the 5' to 3' direction. The tags set 2 also do not hybridise with the initial target DNA duplex strand (51). Furthermore, third forward primer (511) is also tagged at the 5' end with a tag having an identical nucleotide sequence (in the 5' to 3' direction) to that of the second reverse primer (59) and third reverse primer (512) is tagged at the 5' end with a tag having an identical nucleotide sequence (in the 5' to 3' direction) to that of the second forward primer (58). Neither tag can hybridise with the initial target DNA duplex strand (51).

During mPCR amplification of at least three rounds (one round of amplification being one sequence of a denaturing step followed by an annealing step followed by an extension step), the mechanism of which is well known in the art, AM1, AM2 and AM3 are all generated as expected; AM1 (57) being produced due to the first (TS1) forward primer (55) acting in concert with the first (TS1) reverse primer (56), AM2 (510) being produced due to the second (TS2) forward primer (58) acting in concert with the second (TS2) reverse primer (59) and AM3 (513) being produced due to the third (TS3) forward primer (511) acting in concert with the third (TS3) reverse primer (512). Importantly, however, substantially all of the short and long aberrant amplification products that would otherwise be formed exponentially using conventional, non-tagged primers do not accumulate to any significant degree. This is because when the short aberrant amplification product is formed due to second forward primer (58) and first reverse primer (56) acting in concert each single strand comprises at its 5' end the nucleic acid tag of tag set 1 and at its 3' end the complement of the nucleic acid tag (represented as black circles). This enables an intramolecular hybridization event to occur between the nucleic acid tag and its complement to form a secondary hairpin-like structure (516) as shown in FIG. 5B that precludes further amplification of the short aberrant amplification product as previously described. Similarly, when the short aberrant amplification product is formed due to third forward primer (511) and second reverse primer (59) acting in concert each single strand comprises at its 5' end the nucleic acid tag of tag set 2 and at its 3' end the complement of the nucleic acid tag (represented as black triangles). This enables an intramolecular hybridization event to occur between the nucleic acid tag and its complement to form a secondary hairpin-like structure (517) as shown in FIG. 5B that precludes further amplification of the short aberrant amplification product as previously described.

When the long aberrant amplification product is formed due to first forward primer (55) and second reverse primer (59) acting in concert each single strand comprises at its 5' end the nucleic acid tag of tag set 2 and at its 3' end the complement of the nucleic acid tag (represented as black triangles). This enables an intramolecular hybridization event to occur between the nucleic acid tag and its complement to form a secondary hairpin-like structure (518) as shown in FIG. 5B that precludes further amplification of the long aberrant amplification product as previously described. Similarly, when the long aberrant amplification product is formed due to second forward primer (58) and third reverse primer (512) acting in concert each single strand comprises at its 5' end the nucleic acid tag of tag set 1 and at its 3' end the complement of the nucleic acid tag (represented as black circles). This enables an intramolecular hybridization event to occur between the nucleic acid tag and its complement to form a secondary hairpin-like structure (519) as shown in FIG. 5B that precludes further amplification of the long aberrant amplification product as previously described. Whilst it remains theoretically possible for a long aberrant amplification product to form due to first forward primer

(55) and third reverse primer (512) acting in concert, this is least favoured due to it being the largest amplicon. As a consequence, the efficiency of amplification of AM1 (57), AM2 (510) and AM3 (513) is improved using primer sets according to the invention vis-à-vis conventional, non-tagged primer pairs. This design is particularly beneficial for mPCR of multiple overlapping regions of a target nucleic acid in a single reaction vessel because, as shown, the reciprocal arrangement of tags in neighbouring primer pairs frustrates substantially all aberrant amplification production.

In preferred embodiments, the primers of the invention include a universal tag upstream of the primer region. This universal tag is included into the amplification products and thus allows a second amplification to take place that requires the use of universal primers. This is illustrated in FIGS. 6A-C.

Figure 6A:
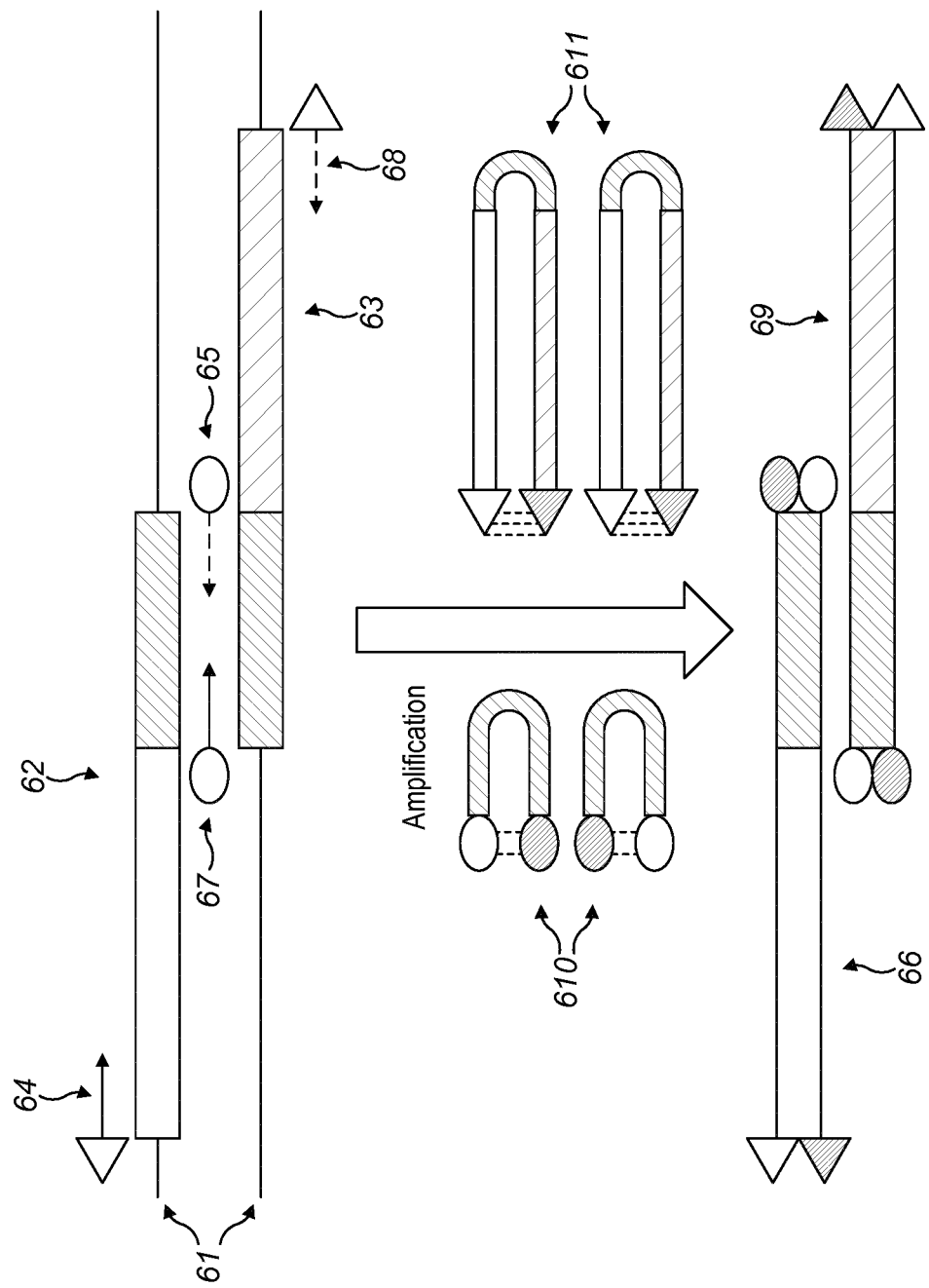
FIG. 6A-C—A schematic representation of the use of two sets of primers of the invention to preclude amplification of both the short and long aberrant amplification products followed by a second amplification with universal primers of the invention.
Figure 6B:
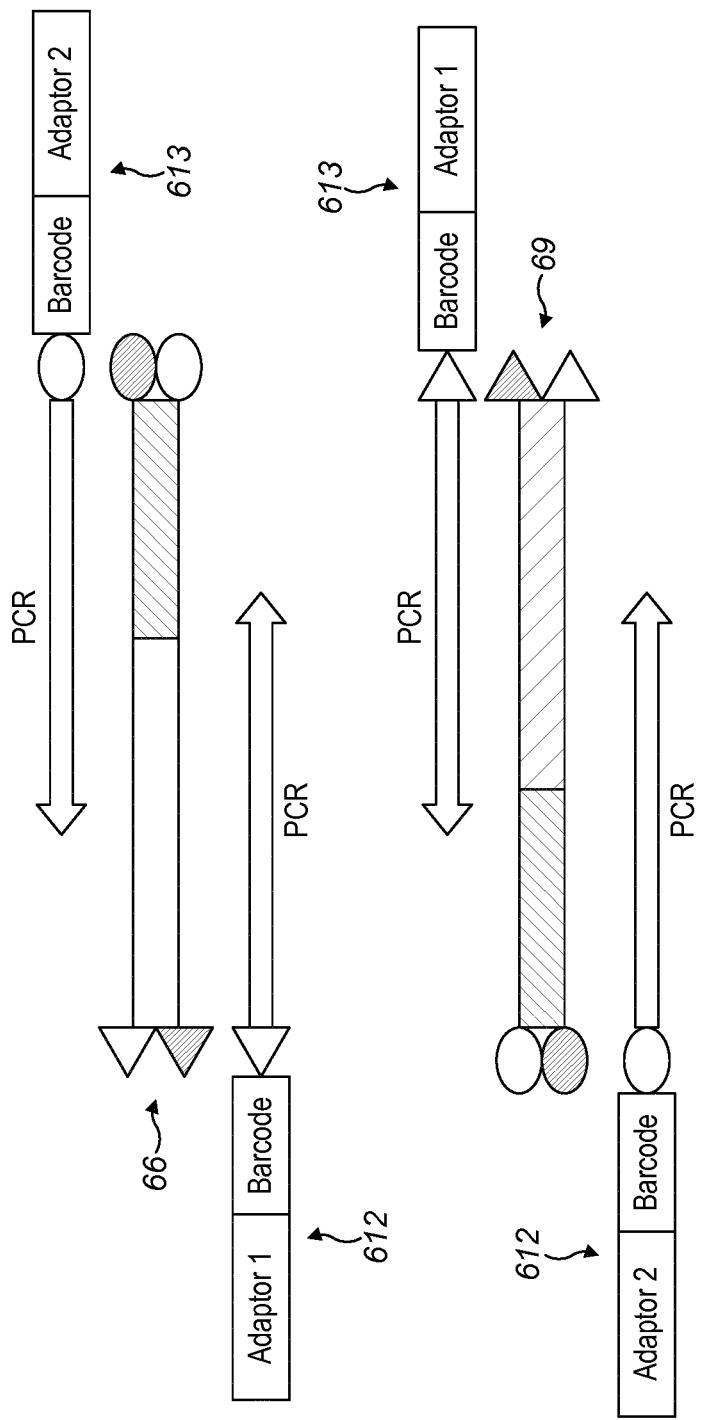
Figure 6C:
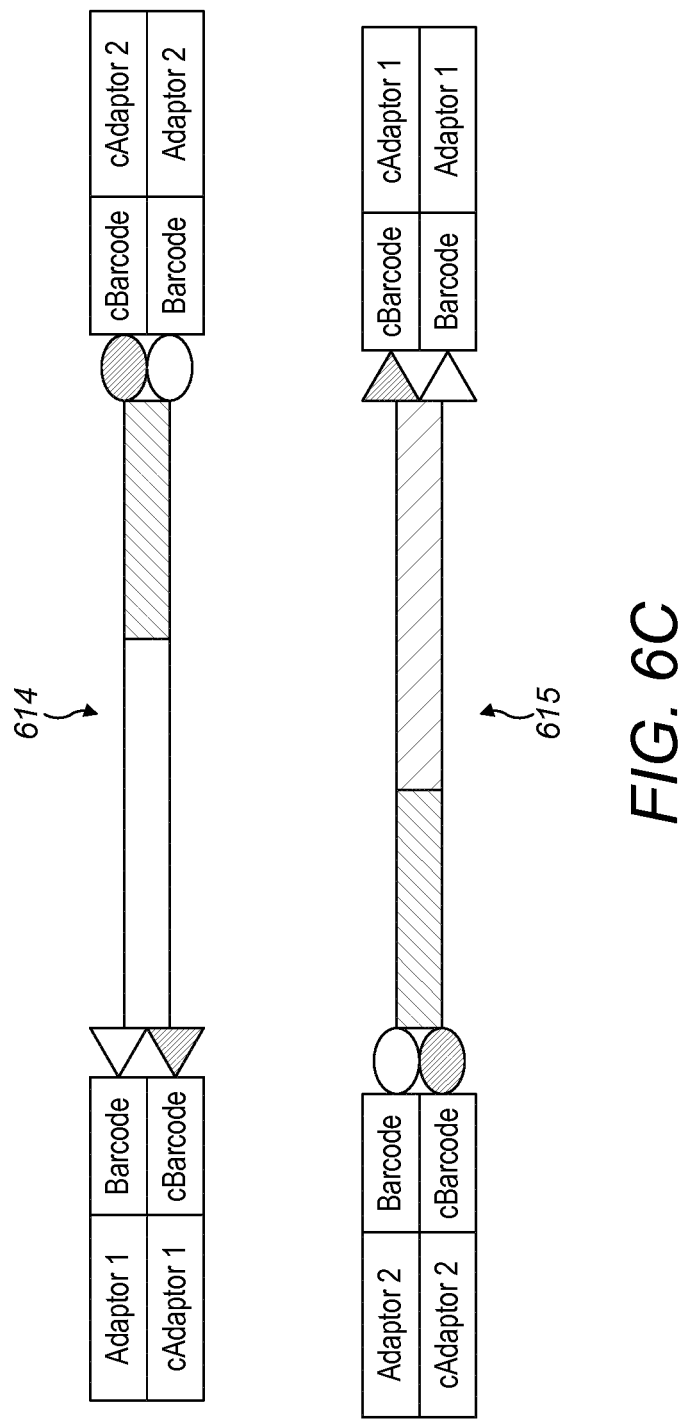

Thus, FIG. 6A shows a DNA duplex strand (61) containing two target sequences to be amplified: target sequence 1 (TS1; 62) and target sequence 2 (TS2; 63). Each respective target sequence is shown independently for the convenience of the reader but it should be understood that both of these sequences are, in fact, present on, and overlap on, the same DNA duplex strand (61). The region of overlap is shown as a dotted box. A first forward primer (64) and first reverse primer (65) are designed to amplify TS1 to produce amplicon 1 (AM1; 66) i.e. the forward primer (64) comprises a primer region (solid arrow) that hybridizes with the anti-sense strand of the DNA duplex strand (61) and the reverse primer (65) comprises a primer region (dashed arrow) that hybridizes with the sense strand of the DNA duplex strand (61) at the respective boundaries of TS1. A second forward primer (67) and second reverse primer (68) are designed to amplify TS2 to produce amplicon 2 (AM2; 69) i.e. the forward primer (67) comprises a primer region (solid arrow) that hybridizes with the anti-sense strand of the DNA duplex strand (61) and the reverse primer (68) comprises a primer region (dashed arrow) that hybridizes with the sense strand of the DNA duplex strand (61) at the respective boundaries of TS2.

As previously described in relation to FIG. 4, first reverse primer (65) and second forward primer (67) are tagged at the 5' end of each primer with identical nucleotide sequences (white circles; hereinafter referred to as 'second universal tags'). For the avoidance of doubt, the sequences are identical in the 5' to 3' direction. The second universal tags do not hybridise with the initial target DNA duplex strand (61). In addition, first forward primer (64) and second reverse primer (68) are tagged at the 5' end of each primer with identical nucleotide sequences which are of a different sequence to those of the second universal tags (white triangles; hereinafter referred to as 'first universal tags1'). For the avoidance of doubt, the sequences are identical in the 5' to 3' direction. The first universal tags also do not hybridise with the initial target DNA duplex strand (61).

As can be seen from the figure, the first and second universal tags are located upstream of the primer region. It should be understood that the universal tags are referred to as "universal" because the same sequence is employed, in reciprocating arrangement, for all primer pairs. Thus, if a third primer pair were present according to the invention and the third forward primer comprised a universal tag it would be the first universal tag (i.e. the same universal tag included in the first forward primer, but different from the universal tag included in the second forward primer). The use of such universal tags simplifies a second amplification reaction by reducing the number of primers needed for the second amplification. The second amplification relies on primer hybridisation to the universal tag sequences incorporated into the amplification products. The same applies to the reverse primer for analogous reasons. Thus, if a third primer pair were present according to the invention and the third reverse primer comprised a universal tag it would be the second universal tag (i.e. the same universal tag included in the first reverse primer, but different from the universal tag included in the second reverse primer) Neither the first universal tag nor second universal tag hybridise with the initial target DNA duplex strand (61).

During mPCR amplification of at least three rounds (one round of amplification being one sequence of a denaturing step followed by an annealing step followed by an extension step), the mechanism of which is well known in the art, both AM1 and AM2 are generated as expected; AM1 being produced due to the first (TS1) forward primer (64) acting in concert with the first (TS1) reverse primer (65) and AM2 being produced due to the second (TS2) forward primer (67) acting in concert with the second (TS2) reverse primer (68). Importantly, however, both the short and long aberrant amplification products that would otherwise be formed exponentially using conventional, non-tagged primers do not accumulate to any significant degree. This is because when the short aberrant amplification product is formed each single strand comprises at its 5' end the second universal tag) and at its 3' end the complement of the second universal tag (represented as black circles). This enables an intramolecular hybridization event to occur between the second universal tag and its complement to form a secondary hairpin-like structure (610) that precludes further amplification of the short aberrant amplification product as previously described. Similarly, when the long aberrant amplification product is formed each single strand comprises at its 5' end the first universal tag and at its 3' end the complement of the nucleic acid tag (represented as black triangles). This enables an intramolecular hybridization event to occur between the nucleic acid tag and its complement to form a secondary hairpin-like structure (611) that precludes further amplification of the long aberrant amplification product as previously described. As a consequence, the efficiency of amplification of AM1 and AM2 is improved.

Furthermore, AM1 (66) and AM2 (69) comprise the first and second universal tags. Importantly and more specifically, the sense strand of AM1 (66) comprises at the 5' end the first universal tag and the anti-sense strand of AM1 (66) comprises at the 5' end the second universal tag. In contrast, the sense strand of AM2 (69) comprises at the 5' end the second universal tag and the anti-sense strand of AM2 (69) comprises at the 5' end the first universal tag. The incorporation of the universal tags then allows a further amplification reaction to occur which incorporates a different adaptor molecules (and optionally a sample barcode molecule) at each end of the second round amplification products.

As shown in FIG. 6B, the complements of the universal tags can now be used as binding sites for a pair of universal primers in a second amplification. More specifically, a first universal primer (612) comprises, in 5' to 3' order:

a. a first adaptor sequence (Adaptor 1) being an adaptor sequence as defined herein
b. a sample barcode sequence as defined herein
c. a universal primer region (white triangle) identical (in the 5' to 3' direction) to the first universal tag incorporated into the amplification products produced as shown;

and a second universal primer (613) comprises, in 5' to 3' order:
  a. a second adaptor sequence (Adaptor 2) being an adaptor sequence as defined herein which shares substantially no or little sequence identity with Adaptor 1
  b. a sample barcode sequence as defined herein
  c. a universal primer region (white circle) identical (in the 5' to 3' direction) to the second universal tag incorporated into the amplification products produced as shown.

Thus, during a second amplification, the first universal primer region (which is identical (in the 5' to 3' direction) to the first universal tag) hybridises to the complement of the first universal tag and primes extension of each amplicon via a (DNA) polymerase enzyme, the mechanism of which is well-known in the art. Similarly, the second universal primer region (which is identical (in the 5' to 3' direction) to the second universal tag) hybridises to the complement of the second universal tag and primes extension of each amplicon via a (DNA) polymerase enzyme.

As a consequence, amplification products (614) and (615) are generated as shown in FIG. 6C. Critically, each product now incorporates a first and second adaptor sequence at either end. Due to the arrangement of the universal tags in the primer pairs, the first and second adaptor sequences may be at opposite ends of the molecule in different amplification products. This is not problematic for subsequent processing. The incorporation of the first and second adaptor sequences at the ends of each amplification product (614) and (615) means they are now ready for high-throughput, massively parallel DNA sequencing. For instance, adaptor 1 and adaptor 2 may be p5 and p7 adaptors respectively required for sequencing using the Illumina MiSeq or HiSeq platform. Alternatively, adaptor 1 and adaptor 2 may be A and P1 adaptors respectively required for sequencing using the Thermo Fisher Ion Proton platform.

Particularly advantageously, the first amplification using first forward primer (64), first reverse primer (65), second forward primer (67) and second reverse primer (65) and the second amplification using universal primers (612) and (613) may be carried out in the same reaction vessel. That is to say, all of the aforesaid primers along with the necessary amplification reagents (dNTPs, polymerase etc.) may be included in combination at the beginning of the reaction. Thus, in a single reaction vessel, desired, overlapping amplicons of a target nucleic acid can be generated complete with the requisite adaptors at the 5' ends of the sense and anti-sense strands respectively for high-throughput, massively parallel DNA sequencing. It is noted that sequencing will take place in a separate reaction vessel (e.g. on a flow cell in a sequencing instrument).

Figure 9A:
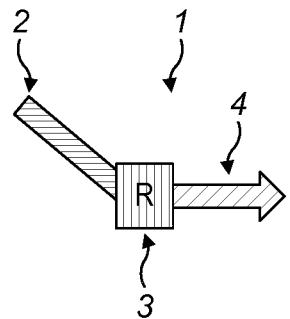
FIG. 9— A schematic representation of a primer according to the invention is provided in FIG. 9A. A representative sequence of such a primer (top strand: SEQ ID NO: 25; bottom strand: SEQ ID NO: 27), and the binding site for the primer on the initial target nucleic acid molecule is also provided in FIG. 9B. A schematic representation of a primer according to the invention and which includes a molecular barcode is provided in FIG. 9C.

Enabling Multistep Amplification Reactions in a Single Reaction Mixture by Controlling the Extent of the First Amplification Reaction FIG. 9A shows schematically a primer (1) for use in a multistep amplification of a target nucleic acid molecule. The primer comprises, in 5' to 3' order, firstly a universal tag (2). The tag (2) is used to incorporate a sequence into the amplification products to which universal primers can hybridise in a second amplification. The tag (2) does not comprise RNA nucleotides and does not hybridise with the initial target nucleic acid molecule. An RNA nucleotide (3) is found downstream (i.e. at the 3' end) of the tag (2). Downstream of the RNA nucleotide (3) is the primer region (4). This primer region (4) hybridizes with a strand of the target nucleic acid molecule to direct amplification. The primer region is typically DNA based and does not include any RNA nucleotides.

Figure 9B:
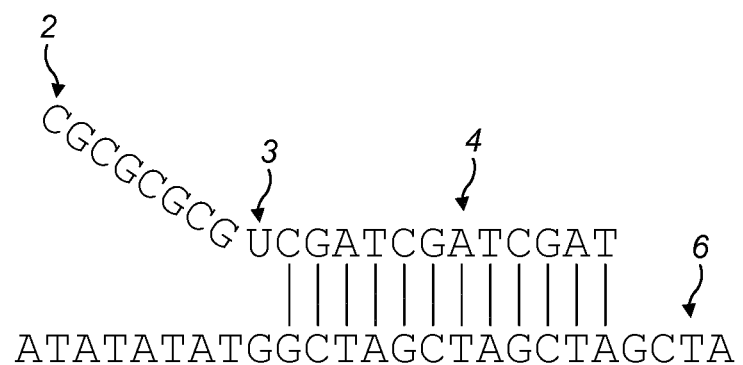

FIG. 9B uses the same labelling as FIG. 9A and shows the initial hybridisation of the primer to a target nucleic acid molecule. This is based on a theoretical target sequence. The tag (2) is comprised of DNA nucleotides and does not hybridise with the initial target nucleic acid molecule. An RNA nucleotide (3), in this case uracil, is found downstream (i.e. at the 3' end) of the tag (2). Downstream of the RNA nucleotide (3) is the primer region (4). This primer region (4) hybridizes with a strand (6) of the target nucleic acid molecule to direct amplification in the 5'-3' direction. The primer region is comprised of DNA nucleotides.

Figure 9C:
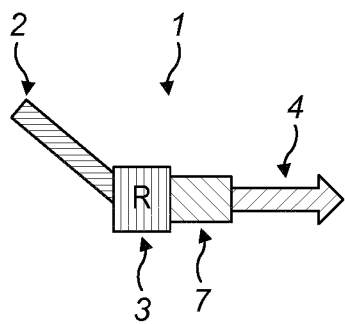

FIG. 9C uses the same labelling as FIG. 9A and shows a primer incorporating a molecular barcode (7). In this figure, the molecular barcode is located downstream of the RNA nucleotide although this is not essential. Typically the molecular barcode is downstream of the universal tag.

Figure 10A:
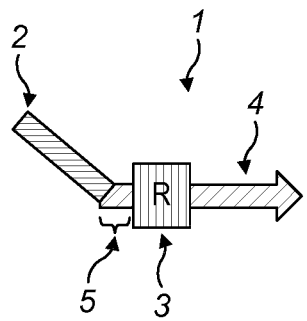
FIG. 10— A schematic representation of a further primer according to the invention is provided in FIG. 10A. A representative sequence of such a primer (top strand: SEQ ID NO: 26; bottom strand: SEQ ID NO: 27), and the binding site for the primer on the initial target nucleic acid molecule is also provided in FIG. 10B. A schematic representation of a further primer according to the invention and which includes a molecular barcode is provided in FIG. 10C.

FIG. 10A uses the same labelling as FIG. 9 and shows schematically a further primer (1) for use in a multistep amplification of a target nucleic acid molecule. The primer comprises, in 5' to 3' order, firstly a universal tag (2). The tag (2) is used to incorporate a sequence into the amplification products to which universal primers can hybridise in a second amplification. The tag (2) does not comprise RNA nucleotides and does not hybridise with the initial target nucleic acid molecule. An RNA nucleotide (3) is found downstream of the tag (2), at the third nucleotide of the primer region (4). This primer region (4) hybridizes with a strand of the target nucleic acid molecule to direct amplification. The primer region is DNA based apart from the single nucleotide. The RNA nucleotide is flanked by only 2 DNA base paired nucleotides at its 5' end (5) and thus does not act as a RNase H substrate.

Figure 10B:
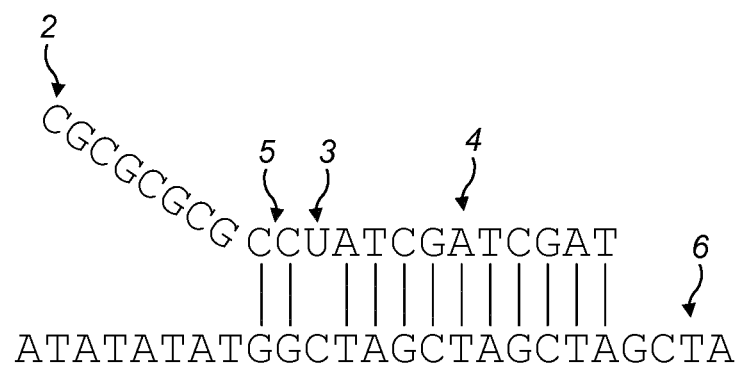
Figure 10C:
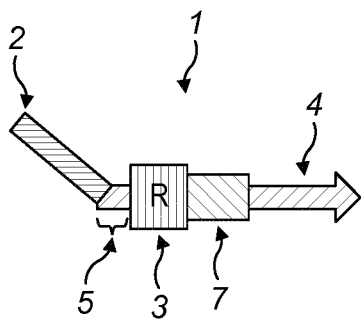

FIG. 10B uses the same labelling as FIG. 10A and shows the initial hybridisation of the primer to a target nucleic acid molecule. This is based on a theoretical target sequence. The tag (2) is comprised of DNA nucleotides and does not hybridise with the initial target nucleic acid molecule. An RNA nucleotide (3) is found downstream of the tag (2), at the third nucleotide of the primer region (4). This primer region (4) hybridizes with a strand (6) of the target nucleic acid molecule to direct amplification in the 5'-3' direction. The primer region contains a single RNA-DNA pair of nucleotides (3). However, this does not provide sufficient double stranded character upstream of the RNA nucleotide. Thus, the annealed primer is not cleaved by RNase H activity. This is because the RNA nucleotide is flanked by only 2 DNA base paired nucleotides at its 5' end (5).

FIG. 10O uses the same labelling as FIG. 10A and shows a primer incorporating a molecular barcode (7). In this figure, the molecular barcode is located downstream of the RNA nucleotide although this is not essential. Typically the molecular barcode is downstream of the universal tag.

Figure 11A:
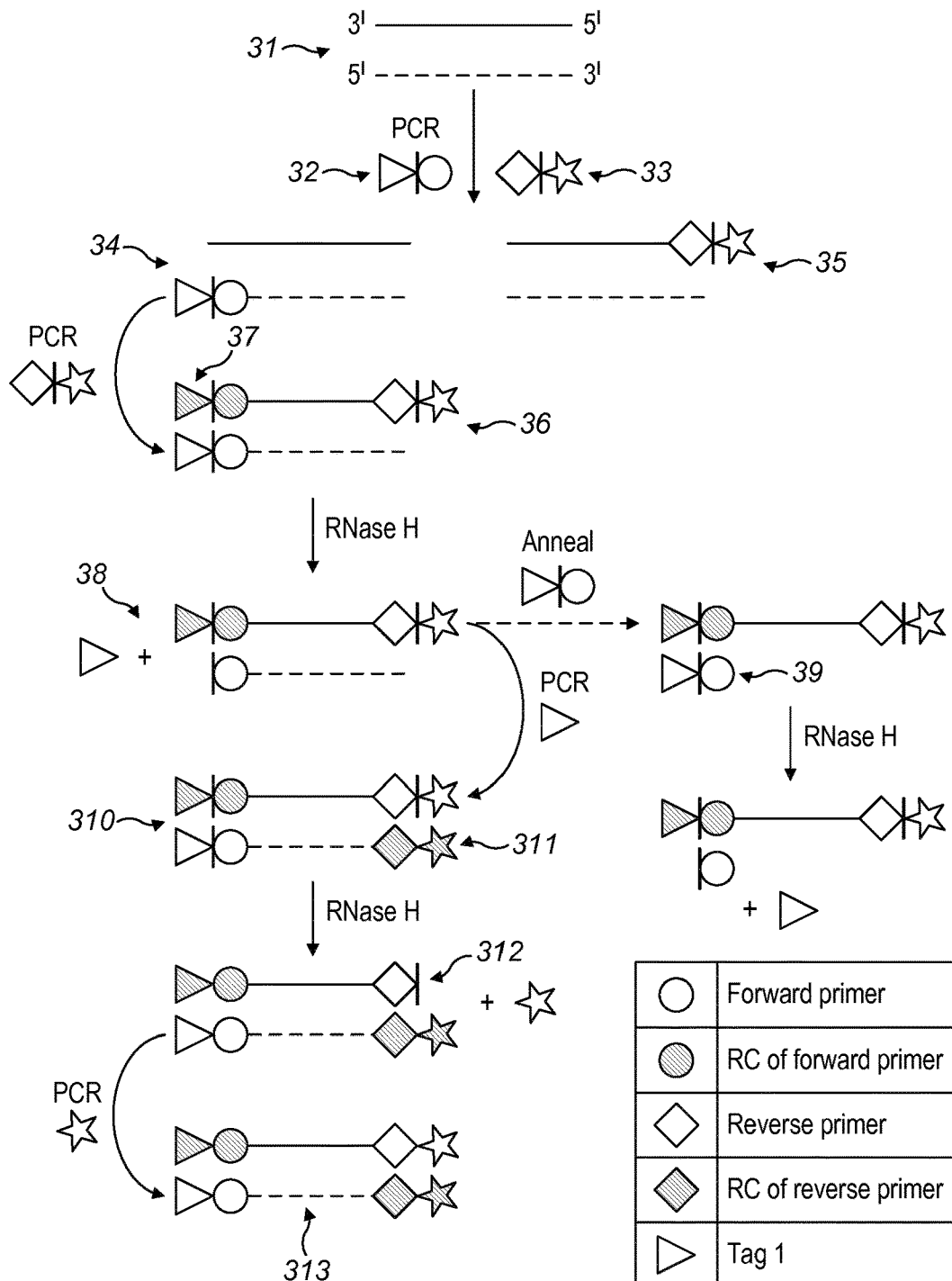
FIG. 11—A schematic representation of the use of the primers of the invention to reduce the efficiency of the first amplification reaction (FIG. 11A). The second "universal" amplification reaction is shown in FIG. 11B.
Figure 11B:
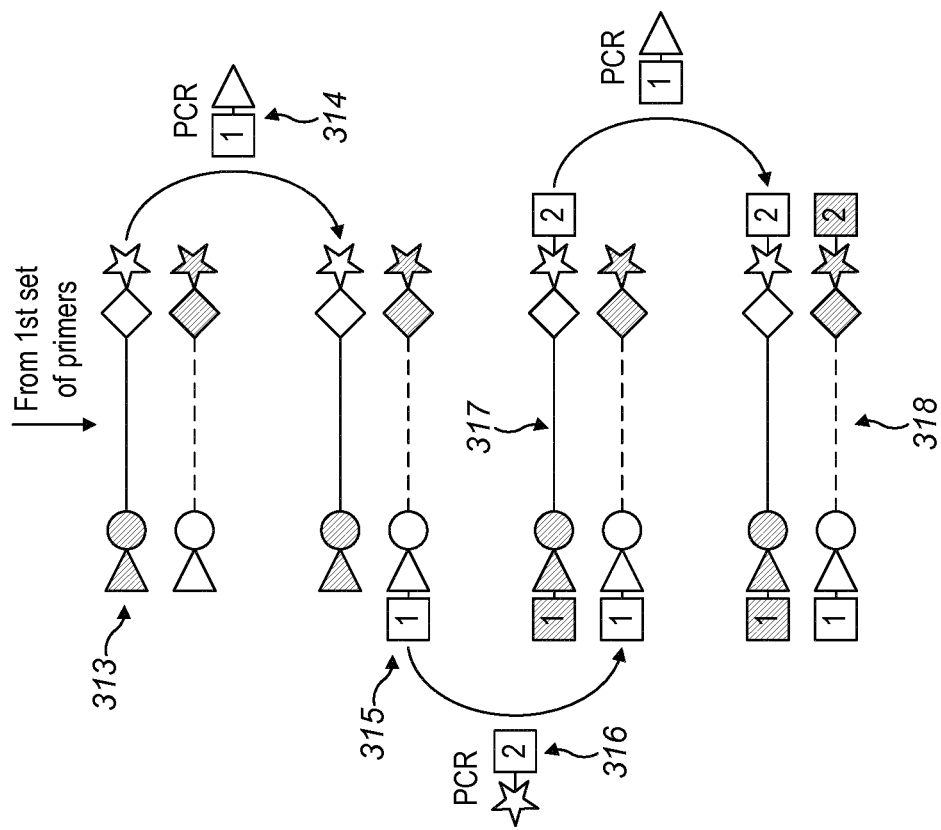

FIG. 11A is a schematic representation of the use of the primers of the invention to limit the first amplification reaction. This is important to prevent competition with the second amplification reaction, which is shown in FIG. 11B. Competition with the second amplification reaction can result in an excess of tagged amplification products that do not incorporate the adapter sequences for downstream processing. A key is included in each figure to facilitate identification of the various molecular components.

In FIG. 11A a target double stranded DNA molecule (31) is shown. Also shown is a forward (32) and reverse (33) primer of the invention. The forward (32) and reverse (33)

primer hybridize with respective strands of the target DNA (31) resulting in amplification by PCR to produce double stranded amplification products (34, 35) with one strand of each product incorporating both a RNA base and a tag.

A second cycle of PCR is shown using the amplification product (34) incorporating the RNA base and tag from the forward primer (32) as an example. In the second cycle of PCR, the reverse (33) primer hybridizes at the 3' end of the amplification product (34) and is extended to produce a double stranded amplification product (36). During the extension reaction, the forward primer is copied. The RNA base is "corrected" by the DNA polymerase as part of this process. Thus, the amplification product (36) incorporates a strand comprising the reverse primer (33) at the 5' end and the reverse compliment of the forward primer, including the tag but without the RNA base, at the 3' end (37).

This amplification product (36) represents a substrate for RNase H, which cleaves the 5' end of the RNA base and releases the first tag (38). Two alternative fates for the top strand of the amplification product (36) are further shown in FIG. 11A. Firstly, if a forward primer (32) hybridises to this strand, a substrate for RNase H activity will be generated upon hybridisation (39). The forward primer (32) is cleaved and thus can only direct amplification of a strand that does not incorporate the tag (not shown). Thus, the product is not useful for the second round of amplification. Secondly, if a cleaved tag from the forward primer (32) acts as a primer it generates a double stranded amplification product (310). During the extension reaction, the reverse primer is copied. The RNA base is "corrected" by the DNA polymerase as part of this process. Thus, the amplification product (310) incorporates a strand comprising the forward primer (32) at the 5' end, without a RNA base, and the reverse compliment of the reverse primer, including the tag but without the RNA base, at the 3' end (311). This strand (311) is a desired product for the second amplification reaction. This double stranded amplification product (310) is a further substrate for RNase H, which cleaves the 5' end of the RNA base and releases the second tag (312).

Taking the strand (311), again there are two alternative fates for this strand. Firstly, if a reverse primer (33) hybridises to this strand, a substrate for RNase H activity will be generated upon hybridisation (not shown). The reverse primer (33) is cleaved and thus can only direct amplification of a strand that does not incorporate the tag (not shown). Thus, the product is not useful for the second round of amplification. Secondly, if a cleaved tag from the reverse primer (33) acts as a primer it generates a double stranded amplification product containing no RNA bases and tagged at both ends of the molecule (313). This is the desired product to direct the second amplification reaction.

In FIG. 11B, the second amplification reaction is shown based on amplification of the double stranded amplification product (313) from the first amplification reaction. Taking the top strand of the double stranded amplification product (313) for representative purposes, the universal forward primer (314), incorporating a first adapter sequence and tag 1 sequence, hybridizes to the reverse complement of the tag 1 sequence and directs extension to incorporate the adapter into the extension product (315). The universal reverse primer (316), incorporating a second adapter sequence and tag 2 sequence, hybridizes to the reverse complement of the tag 2 sequence and directs extension, using extension product (315) as template, to incorporate the adapter into the extension product (317). This strand incorporates an adapter at either end. Extension of this strand (317) using the universal forward primer (314) produces the desired double stranded product incorporating the adapter sequence at either end (318). Note RNase H is unable to act on any of these products due to the absence of any RNA nucleotides found in the relevant double stranded DNA context. Thus, the efficiency of the second amplification reaction is unimpeded by the RNase H present in the reaction mixture.

Figure 12:
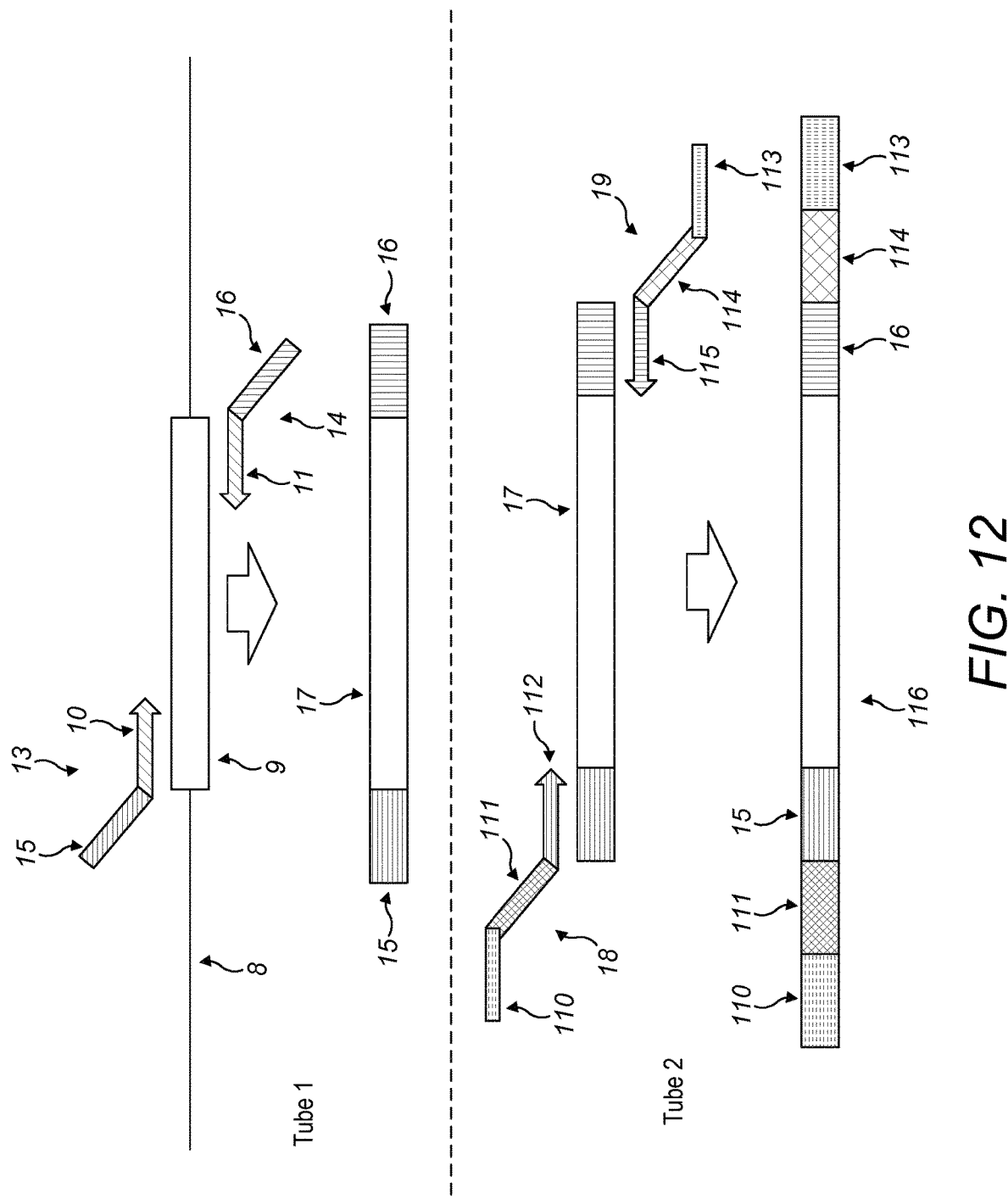
FIG. 12—A schematic representation of the prior art two tube system for carrying out a multistep amplification of a target nucleic acid molecule.

Enabling Multistep Amplification Reactions in a Single Reaction Mixture by Delaying Production of the Universal Primers FIG. 12 shows the prior art system for carrying out a multistep amplification in which the two reaction steps are carried out in separation reaction vessels (Tube 1 and Tube 2).

The first reaction vessel contains a DNA duplex strand (8) containing a target sequence to be amplified (9). A first forward primer (13) and first reverse primer (14) are designed to amplify the target sequence; i.e. the first forward primer (13) comprises a primer region (10) that hybridizes with the anti-sense strand of the target sequence (12) and the first reverse primer (14) comprises a primer region (11) that hybridizes with the sense strand of the target sequence (12).

The first forward primer (13) is tagged at its 5' end with a first universal tag (15) and the first reverse primer (14) is tagged at its 5' end with a second universal tag (16). During PCR amplification, the mechanism of which is well known in the art, the first forward primer (13) and first reverse primer (14) generate an amplification product (17) which incorporates the first universal tag (15) and second universal tag (16).

In a subsequent reaction in a second reaction vessel (Tube 2) a second forward primer (18) and a second reverse primer (19) are used to amplify the amplification product (17) from the first reaction in Tube 1. The second forward primer (18) comprises, in 5' to 3' order, a first adapter sequence (110), optionally a first barcode sequence (111) and a primer region (112) that hybridizes with the complement of the first universal tag (15) incorporated into the antisense strand. The second reverse primer (19) comprises, in 5' to 3' order, a second adapter sequence (113), a second barcode sequence (114) and a primer region (115) that hybridizes with the sense strand of the second universal tag (16). During PCR amplification, the second forward primer (18) and second reverse primer (19) generate a further amplification product (116) which incorporates the first and second universal tags (15, 16), first and second barcodes (111, 114) and first and second adapter sequences (110, 113).

This system is inefficient and labour intensive. Moreover, the requirement to stop and separate the reaction mixture after the first step introduces possible errors and contamination into the system.

FIG. 13 illustrates how the use of the set of reagents of the invention allows a multistep amplification of a target nucleic acid molecule to be carried out in a single reaction mixture, which provides numerous advantages over previous methods.

FIG. 13 is presented to illustrate the three separate amplification processes that occur in parallel in the same reaction mixture or vessel.

Figure 13A:
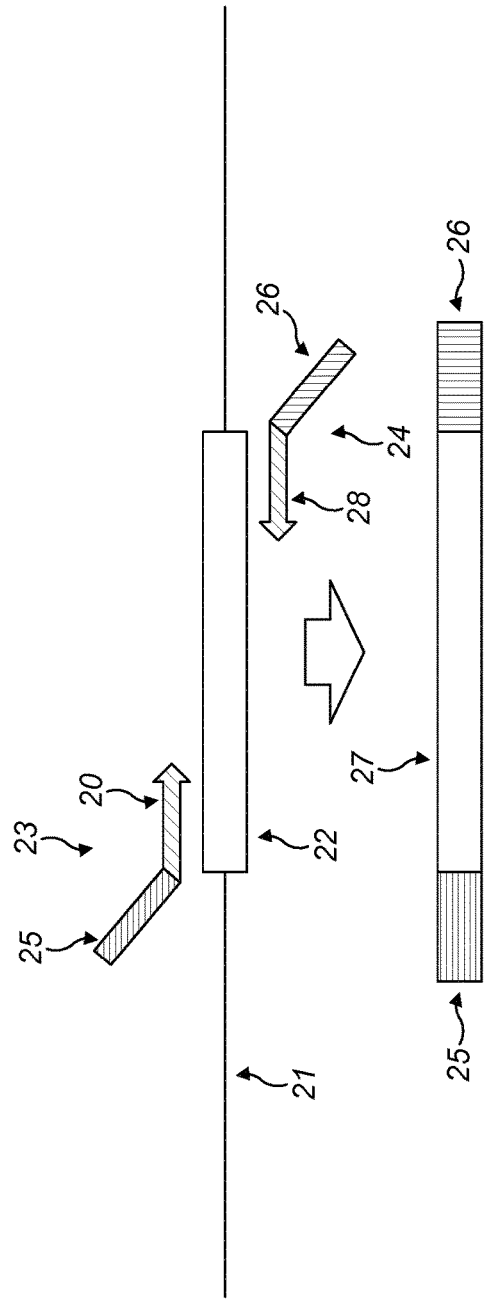
FIG. 13—A schematic representation of the use of the set of reagents of the invention to carry out a multistep amplification of a target nucleic acid molecule in a single reaction mixture.

FIG. 13A shows the first amplification. The single reaction mixture contains a DNA duplex strand (21) containing a target sequence to be amplified (22). A first forward primer (23) and first reverse primer (24) are designed to amplify the target sequence; i.e. the first forward primer (23) comprises a primer region (20) that hybridizes with the anti-sense strand of the target sequence (22) and the first reverse primer (24) comprises a primer region (28) that hybridizes with the sense strand of the target sequence (22).

The first forward primer (23) is tagged at its 5' end with a first universal tag (25) and the first reverse primer (24) is tagged at its 5' end with a second universal tag (26). During PCR amplification, the mechanism of which is well known in the art, the first forward primer (23) and first reverse primer (24) generate an amplification product (27) which incorporates the first universal tag (25) and second universal tag (26).

Figure 13B:
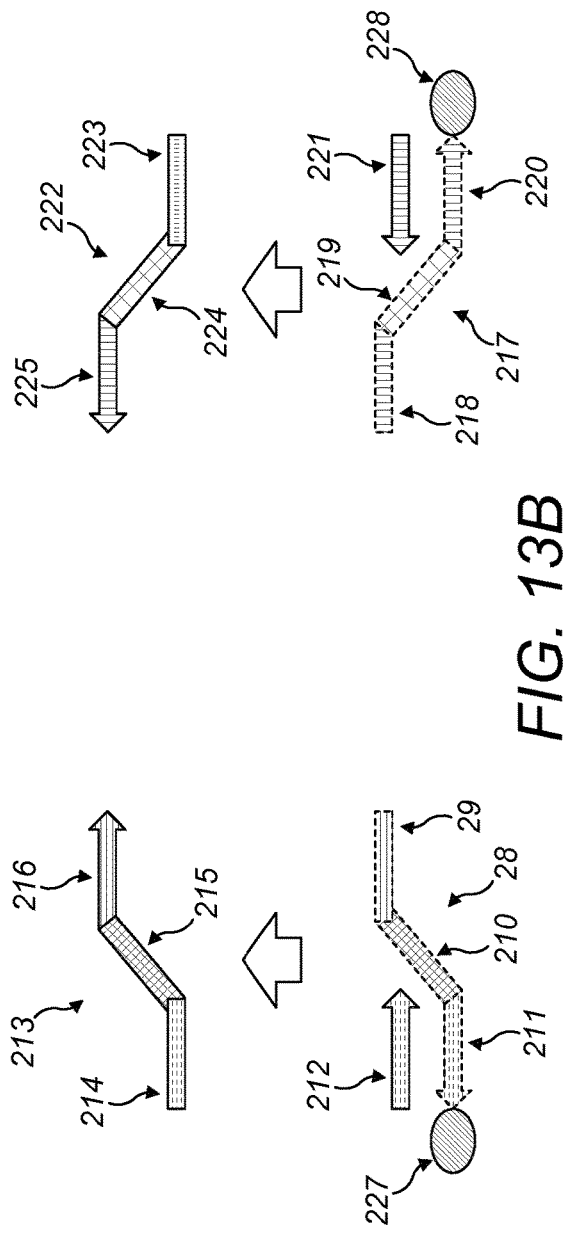

FIG. 13B shows an amplification that occurs in parallel with the first amplification. The reaction mixture also contains a first nucleic acid molecule (28) comprising, in 5' to 3' order, a sequence of nucleotides that is the reverse complement of the first universal tag (29), optionally a sequence of nucleotides that is the reverse complement of a first barcode (210), a sequence of nucleotides that is the reverse complement of a first adapter sequence (211) and a blocking group (227) that prevents extension beyond the adapter sequence (211). A first adapter primer (212) hybridizes with the reverse complement of the first adapter sequence (211) to generate an amplification product (213) comprising, in 5' to 3' order, the first adapter sequence (214), optionally the first barcode (215) and the first universal tag (216).

The reaction mixture further contains a second nucleic acid molecule (217) comprising, in 5' to 3' order, a sequence of nucleotides that is the reverse complement of the second universal tag (218), optionally a sequence of nucleotides that is the reverse complement of a second barcode (219), a sequence of nucleotides that is the reverse complement of a second adapter sequence (220) and a blocking group (228) that prevents extension beyond the adapter sequence (220). A second adapter primer (221) hybridizes with the reverse complement of the second adapter sequence (220) to generate an amplification product (222) comprising, in 5' to 3' order, the second adapter sequence (223), optionally the second barcode (224) and the second universal tag (225).

Figure 13C:
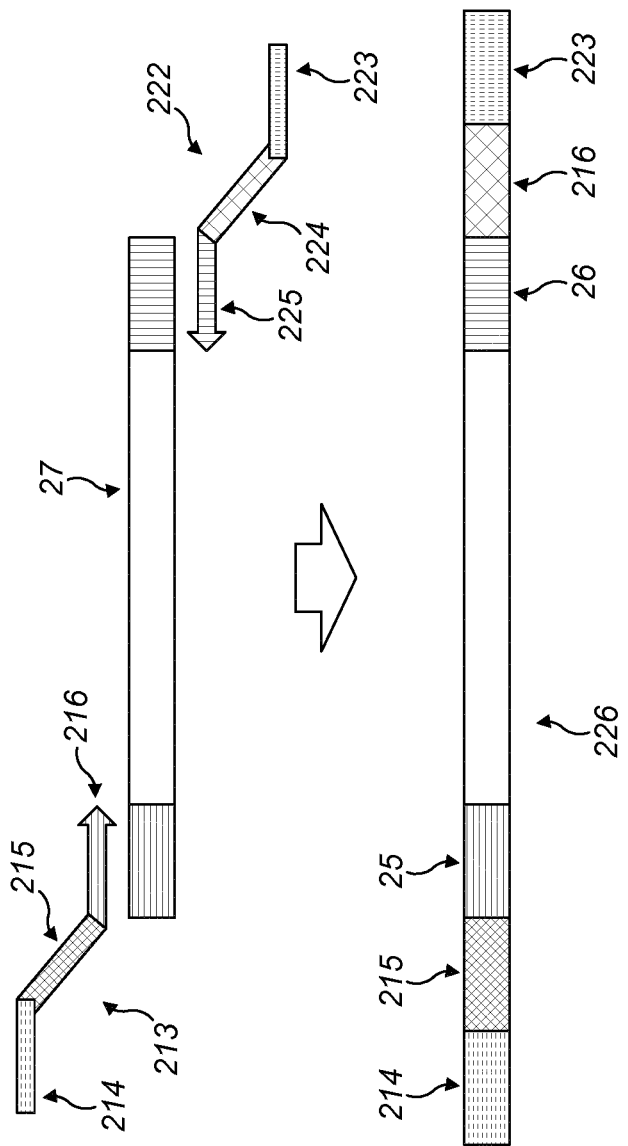

FIG. 13C shows the second amplification. Amplification products 213 and 225 from FIG. 13B form a universal primer pair in which the first universal tag sequence (216) and the second universal tag sequence (223) act as primers to amplify the amplification product (27) from the first amplification. This generates a further amplification product (226) comprising the first and second universal tags (25, 26), optionally first and second barcodes (215, 224) and first and second adapters (214, 223). The further amplification product is useful for downstream processing, typically involving sequencing to detect and/or quantify the target nucleic acid molecule.

The use of the first and second nucleic acid molecules (28, 217) with the first and second adapter primers (212, 221) temporally delay to the production of the amplification products 213 and 222. This allows for the first amplification of the target nucleic acid molecule to produce tagged amplification product (27). By the time amplification products 213 and 222 have been generated, which act as universal primers to perform the second amplification, the substrate amplification product (27) is already present in excess.

CLAUSES

The improvements as described herein can each be advantageously combined with each other to allow for an improved method. Such combinations are described in more detail in the Clauses below.

1. A set of primers for use in multiplex amplification of overlapping regions of a target nucleic acid molecule, comprising:
    a. a first primer pair designed to amplify a first region of the target nucleic acid molecule, comprising:
        i. a first forward primer incorporating a primer region that hybridizes with a strand of the target nucleic acid molecule
        ii. a first reverse primer incorporating a primer region that hybridizes with a strand of the target nucleic acid molecule and a nucleic acid tag 5' of the primer region
    b. a second primer pair designed to amplify a second region of the target nucleic acid molecule that at least partially overlaps with the first region, comprising:
        i. a second forward primer incorporating a primer region that hybridizes with a strand of the target nucleic acid molecule and a nucleic acid tag 5' of the primer region which is identical in the 5' to 3' direction with the nucleic acid tag incorporated at the 5' end of the first reverse primer
        ii. a second reverse primer incorporating a primer region that hybridizes with a strand of the target nucleic acid molecule,
    wherein, in the event that an aberrant (short) amplification product is formed between the first reverse primer and second forward primer, an intramolecular hybridization event occurs between the nucleic acid tag at the 5' end of the aberrant (short) amplification product and the complementary sequence at the 3' end of the aberrant (short) amplification product formed during amplification to form a secondary structure that precludes further amplification of the aberrant amplification product.
2. The set of primers of clause 1 wherein the first forward primer and second reverse primer also incorporate a nucleic acid tag 5' of the primer region, further characterised in that the nucleic acid tag of the first forward primer and the nucleic acid tag of the second reverse primer are identical in the 5' to 3' direction such that, in the event that an aberrant (long) amplification product is formed between the first forward primer and second reverse primer, an intramolecular hybridization event occurs between the nucleic acid tag at the 5' end of the aberrant (long) amplification product and the complementary sequence at the 3' end of the aberrant (long) amplification product formed during amplification to form a secondary structure that precludes further amplification of the aberrant amplification product.
3. The set of primers according to clause 2, further comprising:
    a. a third primer pair designed to amplify a third region of the target nucleic acid molecule that at least partially overlaps with the second region, comprising:
        i. a third forward primer incorporating a primer region that hybridizes with a strand of the target nucleic acid molecule and a nucleic acid tag 5' of the primer region
        ii. a third reverse primer incorporating a primer region that hybridizes with a strand of the target nucleic acid molecule,
    wherein the nucleic acid tag of the third forward primer and the nucleic acid tag of the second reverse primer are also identical in the 5' to 3' direction such that, in the event that an aberrant (short) amplification product is formed between the third forward primer and second reverse primer, an intramolecular hybridization event occurs between the nucleic acid tag at the 5' end of the aberrant (short) amplification product and the complementary sequence at the 3' end of the aberrant (short) amplification product formed during amplification to form a secondary structure that precludes further amplification of the aberrant amplification product.
4. The set of primers of clause 3 wherein the third reverse primer also incorporates a nucleic acid tag 5' of the primer region, further characterised in that the nucleic acid tag of the second forward primer and the nucleic acid tag of the third reverse primer are also identical in the 5' to 3' direction such that, in the event that an aberrant (long) amplification product is formed between the second forward primer and third reverse primer, an intramolecular hybridization event occurs between the nucleic acid tag at the 5' end of the aberrant (long) amplification product and the complementary sequence at the 3' end of the aberrant (long) amplification product formed during amplification to form a secondary structure that precludes further amplification of the aberrant amplification product.
5. A set of primers for use in multiplex amplification of overlapping regions of a target nucleic acid molecule, comprising:
   a. at least two primer pairs designed to amplify overlapping regions of the target nucleic acid molecule, each primer pair comprising:
      i. a forward primer incorporating a primer region that hybridizes with a strand of the target nucleic acid molecule and a nucleic acid tag 5' of the primer region
      ii. a reverse primer incorporating a primer region that hybridizes with a strand of the target nucleic acid molecule and a nucleic acid tag 5' of the primer region,
   wherein the nucleic acid tag of the forward and reverse primer in each primer pair are different, the nucleic acid tag of the forward and reverse primer in immediately neighbouring primer pairs are identical in the 5' to 3' direction such that, in the event that an aberrant amplification product is formed between the forward and reverse primers of immediately neighbouring primer pairs, an intramolecular hybridization event occurs between the nucleic acid tag at the 5' end of the aberrant amplification product and the complementary sequence at the 3' end of the aberrant amplification product formed during amplification to form a secondary structure that precludes further amplification of the aberrant amplification product.
6. The set of primers according to any preceding clause wherein the Tm of the nucleic acid tag and its complementary sequence is higher than the highest Tm of the primer regions.
7. The set of primers according to clause 5 wherein the Tm of the nucleic acid tag and its complementary sequence is at least 2° C. higher, optionally up to 10° C. higher than the highest Tm of the primer regions.
8. The set of primers according to any preceding clause wherein each tag is at least 4 nucleotides, optionally up to 20 nucleotides, in length.
9. The set of primers according to any preceding clause wherein each tag is 4, 6, 8 or 10 nucleotides in length.
10. The set of primers according to any preceding clause wherein each tag comprises a
GC rich sequence.
11. The set of primers according to any preceding clause wherein each primer pair is intended to produce an amplification product of 50-150 nucleotides.
12. The set of primers according to any preceding clause wherein the level of overlap between the intended amplification products generated from immediately neighbouring primer pairs is 10-30 nucleotides.
13. The set of primers according to any preceding clause wherein each tag shows no identity with the target nucleic acid molecule.
14. The set of primers according to any preceding clause wherein each nucleic acid tag comprises a universal tag.
15. The set of primers according to clause 14 wherein each primer pair comprises a first universal tag and a second universal tag.
16. The set of primers according to any preceding clause wherein at least one primer in each primer pair includes a barcode, optionally a molecular barcode.
17. The set of primers according to any preceding clause wherein each primer includes a barcode, optionally a molecular barcode.
18. A kit for multiplex nucleic acid amplification comprising a set of primers as defined in any one of clauses 1 to 17.
19. The kit of clause 18 further comprising at least one of:
   a. universal primers, each universal primer comprising, in 5' to 3' order:
      i. an adaptor sequence
      ii. optionally a sample barcode sequence
      iii. a universal primer region identical (in the 5' to 3' direction) to the universal tag of a corresponding primer used in the multiplex amplification
   b. a DNA polymerase
   c. dNTPs
20. The kit of clause 18 or 19 comprising:
   a. a first universal primer comprising, in 5' to 3' order:
      i. a first adaptor sequence
      ii. optionally a sample barcode sequence
      iii. a universal primer region identical (in the 5' to 3' direction) to the first universal tag
   b. a second universal primer comprising, in 5' to 3' order:
      i. a second adaptor sequence
      ii. optionally a sample barcode sequence
      iii. a universal primer region identical (in the 5' to 3' direction) to the second universal tag
21. A reaction vessel for multiplex nucleic acid amplification comprising a set of primers as defined in any one of clauses 1 to 17.
22. The reaction vessel of clause 21 further comprising at least one of:
   a. universal primers for subsequent sequencing, each universal primer comprising, in 5' to 3' order:
      i. an adaptor sequence
      ii. optionally a sample barcode sequence
      iii. a universal primer region identical (in the 5' to 3' direction) to the universal tag of a corresponding primer used in the multiplex amplification
   b. a DNA polymerase
   c. dNTPs
23. The reaction vessel of clause 21 or 22 comprising:
   a. a first universal primer comprising, in 5' to 3' order:
      i. a first adaptor sequence
      ii. optionally a sample barcode sequence
      iii. a universal primer region identical (in the 5' to 3' direction) to the first universal tag

53 b. a second universal primer comprising, in 5' to 3' order:
  i. a second adaptor sequence
  ii. optionally a sample barcode sequence
  iii. a universal primer region identical (in the 5' to 3' direction) to the second universal tag
24. The kit of any of clauses 18 to 20 or reaction vessel of any of clauses 21 to 23 further comprising a reverse transcriptase.
25. The kit of clause 20 or reaction vessel of clause 23 wherein the first adaptor sequence is different to the second adaptor sequence.
26. The kit or reaction vessel of clause 25 wherein the first adaptor sequence is a p5 adaptor and the second adaptor sequence is a p7 adaptor.
27. The kit or reaction vessel of clause 25 wherein the first adaptor sequence is an A adaptor and the second adaptor sequence is a P1 adaptor.
28. A multiplex nucleic acid amplification reaction comprising amplification of overlapping regions of a target nucleic acid molecule using a set of primers as defined in any one of clauses 1 to 17 to create tagged amplification products.
29. The multiplex nucleic acid amplification reaction of clause 28, further comprising an additional amplification to prepare the tagged amplification products for sequencing, the additional amplification reaction utilising universal primers, each universal primer comprising, in 5' to 3' order:
  a. an adaptor sequence
  b. optionally a sample barcode sequence
  c. a universal primer region identical (in the 5' to 3' direction) to the universal tag of a corresponding primer used in the multiplex amplification.
30. The multiplex nucleic acid amplification reaction of clause 28 or 29 wherein the universal primers form a universal primer pair, comprising:
  a. a first universal primer comprising, in 5' to 3' order:
    i. a first adaptor sequence
    ii. optionally a sample barcode sequence
    iii. a universal primer region identical (in the 5' to 3' direction) to the first universal tag
  b. a second universal primer comprising, in 5' to 3' order:
    i. a second adaptor sequence
    ii. optionally a sample barcode sequence
    iii. a universal primer region identical (in the 5' to 3' direction) to the second universal tag
31. The multiplex nucleic acid amplification reaction of clause 30 wherein the first adaptor sequence is a p5 adaptor and the second adaptor sequence is a p7 adaptor.
32. The multiplex nucleic acid amplification reaction of clause 30 wherein the first adaptor sequence is an A adaptor and the second adaptor sequence is a P1 adaptor.
33. The multiplex nucleic acid amplification reaction of any one of clauses 29-32 wherein the sequencing is next generation sequencing.
34. A primer for use in a multistep amplification of a target nucleic acid molecule, comprising, in 5' to 3' order:
  a. a universal tag that does not comprise RNA nucleotides
  b. an RNA nucleotide
  c. a primer region that does not comprise RNA nucleotides and that hybridizes with a strand of the target nucleic acid molecule.

54

35. The primer of clause 34 that does not include a blocking group downstream of the RNA nucleotide.
36. The primer of clause 34 comprising, in 5' to 3' order:
  a. a universal tag
  b. an RNA nucleotide
  c. a primer region that hybridizes with a strand of the target nucleic acid molecule
  d. a further RNA nucleotide
  e. a further region that hybridizes with a strand of the target nucleic acid molecule
  f. a blocking group.
37. The primer of any of clauses 34 to 36 wherein the tag and/or primer region consist of DNA nucleotides.
38. The primer of any one of clauses 34 to 37 that further comprises a barcode sequence downstream of the RNA nucleotide, optionally a molecular barcode.
39. The primer of any one of clauses 34 to 38 comprising, in 5' to 3' order:
  a. a universal tag that does not comprise RNA nucleotides
  b. up to 4 nucleotides that hybridise with a strand of the target nucleic acid molecule
  c. an RNA nucleotide
  d. a primer region that does not comprise RNA nucleotides and that hybridizes with a strand of the target nucleic acid molecule, wherein regions b and d both hybridise with the same target nucleic acid molecule resulting in a RNA nucleotide paired with a DNA base in the target nucleic acid molecule.
40. A primer pair comprising a forward and reverse primer according to any one of clauses 34 to 39 for amplifying a target nucleic acid molecule.
41. A set of reagents for use in a multistep amplification of a target nucleic acid molecule, comprising:
  a. a primer according to any one of clauses 34 to 39 or a primer pair as defined in clause 40
  b. RNase H.
42. A multistep amplification of a target nucleic acid molecule comprising use of a primer as described in any one of clauses 34 to 39, a primer pair as described in clause 40 or a set of reagents as described in clause 41.
43. A method for amplification of a target nucleic acid molecule comprising amplifying the target nucleic acid molecule in the presence of RNase H using a first primer pair, comprising:
  i. a first forward primer comprising, in 5' to 3' order:
    a. a universal tag that does not comprise RNA nucleotides
    b. an RNA nucleotide
    c. a primer region that does not comprise RNA nucleotides and that hybridizes with a strand of the target nucleic acid molecule
  ii. a first reverse primer comprising, in 5' to 3' order:
    a. a universal tag that does not comprise RNA nucleotides (that does not hybridise with the initial target nucleic acid molecule)
    b. an RNA nucleotide
    c. a primer region that does not comprise RNA nucleotides and that hybridizes with a strand of the target nucleic acid
  such that:
  c. following the first round of amplification, the target nucleic acid molecule is replicated and a first amplification product incorporates the universal tag and RNA nucleotide of the first forward primer and a second amplification product incorporates the universal tag and RNA nucleotide of the first reverse primer;
d. in the second round of amplification, the first reverse primer hybridizes with the first amplification product to generate a third amplification product incorporating the complement of the universal tag and DNA complement of the RNA nucleotide of the first forward primer and the first forward primer hybridizes with the second amplification product to generate a fourth amplification product incorporating the complement of the universal tag and DNA complement of the RNA nucleotide of the first reverse primer, wherein the third and fourth amplification products each represent a substrate for RNase H activity resulting in cleavage of the RNA nucleotide thereby limiting further amplification of the target nucleic acid molecule.

44. The method as described in clause 43 wherein the first forward primer and/or first reverse primer is as defined in any one of clauses 34 to 39.

45. The primer as described in any one of clauses 34 to 39, a primer pair as described in clause 40 or a set of reagents as described in clause 41 or amplification as described in any one of clauses 42 to 44 wherein:
    a. the RNase H is thermostable, such as RNase H2, optionally RNase H2 from *Pyrococcus abyssi*; and/or
    b. the target nucleic acid molecule comprises genomic DNA or cDNA; and/or
    c. the target nucleic acid molecule is double or single stranded.

46. A kit for multistep amplification of a target nucleic acid molecule comprising a primer as described in any one of clauses 34 to 39, a primer pair as described in clause 40 or a set of reagents as described in clause 41.

47. The kit of clause 46 further comprising at least one of a DNA polymerase and dNTPs.

48. The set of primers according to any one of clauses 1 to 17 wherein at least one primer in the set is a primer according to any one of clauses 34 to 39.

49. The set of primers according to any one of clauses 1 to 17 wherein each primer pair in the set comprises a primer according to any one of clauses 34 to 39.

50. The set of primers according to any one of clauses 1 to 17 wherein each primer pair in the set comprises a primer pair according to clause 40.

51. The set of primers according to any one of clauses 1 to 17 wherein each primer in the set is a primer according to any one of clauses to 34 to 39.

52. A multiplex and multistep amplification of a target nucleic acid molecule comprising use of a set of primers as claimed in any one of clauses 48 to 51.

53. The amplification of clause 52 wherein the amplification comprises a multiplex nucleic acid amplification reaction comprising amplification of overlapping regions of a target nucleic acid molecule.

54. The amplification of clause 52 or 53 comprising a second amplification employing:
    a. a first universal primer comprising, in 5' to 3' order:
       i. a first adaptor sequence
       ii. optionally a sample barcode sequence
       iii. a universal primer region identical (in the 5' to 3' direction) to the first universal tag
    b. a second universal primer comprising, in 5' to 3' order:
       i. a second adaptor sequence
       ii. optionally a sample barcode sequence
       iii. a universal primer region identical (in the 5' to 3' direction) to the second universal tag 55. A method of detecting and/or quantifying a target nucleic acid molecule comprising:
    a. performing the method of clause 54 in order to generate amplification products incorporating universal tags and adapter sequences
    b. sequencing the amplification products in order to detect and/or quantify the target nucleic acid molecule, optionally wherein the sequencing is next generation sequencing.

56. A set of reagents for use in a multistep amplification of a target nucleic acid molecule, comprising:
    a. a first primer pair designed to amplify the target nucleic acid molecule, comprising:
       i. a first forward primer incorporating a primer region that hybridizes with a strand of the target nucleic acid molecule and a first universal tag 5' of the primer region
       ii. a first reverse primer incorporating a primer region that hybridizes with a strand of the target nucleic acid molecule and a second universal tag 5' of the primer region
    b. a first nucleic acid molecule comprising in 5' to 3' order:
       i. a sequence of nucleotides that is the reverse complement of the first universal tag
       ii. a sequence of nucleotides that is the reverse complement of a first adapter sequence needed for subsequent processing
       iii. a blocking group preventing extension beyond the adapter sequence.
    c. a second nucleic acid molecule comprising in 5' to 3' order:
       i. a sequence of nucleotides that is the reverse complement of the second universal tag
       ii. a sequence of nucleotides that is the reverse complement of a second adapter sequence needed for subsequent processing
       iii. a blocking group preventing extension beyond the second adapter sequence
    d. a first adapter primer that hybridizes with the reverse complement of the first adapter sequence to generate an amplification product comprising in 5' to 3' order:
       i. the first adapter sequence
       ii. the first universal tag
    e. a second adapter primer that hybridizes with the reverse complement of the second adapter sequence to generate an amplification product comprising in 5' to 3' order:
       i. the second adapter sequence
       ii. the second universal tag
    wherein the amplification products generated using the first and second adapter primers of d and e form a universal primer pair in which the first and second universal tags act as primers to amplify amplification products generated by the first primer pair to produce further amplification products incorporating the first and second universal tags and adapters.

57. A set of reagents for use in a multistep amplification of a target nucleic acid molecule, comprising:
  a. a first nucleic acid molecule comprising in 5' to 3' order:
    i. a sequence of nucleotides that is the reverse complement of a first universal tag incorporated in a forward primer of a first primer pair that hybridizes with a strand of the target nucleic acid molecule
    ii. a sequence of nucleotides that is the reverse complement of a first adapter sequence needed for subsequent processing
    iii. a blocking group preventing extension beyond the first adapter sequence.
  b. a second nucleic acid molecule comprising in 5' to 3' order:
    i. a sequence of nucleotides that is the reverse complement of a second universal tag incorporated in a reverse primer of the first primer pair that hybridizes with a strand of the target nucleic acid molecule
    ii. a sequence of nucleotides that is the reverse complement of a second adapter sequence needed for subsequent processing
    iii. a blocking group preventing extension beyond the second adapter sequence
  c. a first adapter primer that hybridizes with the reverse complement of the first adapter sequence to generate an amplification product comprising in 5' to 3' order:
    i. the first adapter sequence
    ii. the first universal tag
  d. a second adapter primer that hybridizes with the reverse complement of the second adapter sequence to generate an amplification product comprising in 5' to 3' order:
    i. the second adapter sequence
    ii. the second universal tag
  wherein the amplification products generated using the first and second adapter primers of c and d form a universal primer pair in which the first and second universal tags act as primers to amplify amplification products generated by the first primer pair to produce further amplification products incorporating the first and second universal tags and adapters.

58. A method for multistep amplification of a target nucleic acid molecule, comprising:
  a. amplifying the target nucleic acid molecule using a first primer pair, comprising:
    i. a first forward primer incorporating a primer region that hybridizes with a strand of the target nucleic acid molecule and a first universal tag 5' of the primer region
    ii. a first reverse primer incorporating a primer region that hybridizes with a strand of the target nucleic acid molecule and a second universal tag 5' of the primer region
  to produce first amplification products incorporating the first universal tag and the second universal tag
  b. amplifying a first nucleic acid molecule comprising in 5' to 3' order:
    i. a sequence of nucleotides that is the reverse complement of the first universal tag
    ii. a sequence of nucleotides that is the reverse complement of a first adapter sequence needed for subsequent processing
    iii. a blocking group preventing extension beyond the first adapter sequence
  using a first adapter primer that hybridizes with the reverse complement of the first adapter sequence to generate an amplification product comprising in 5' to 3' order:
    i. the first adapter sequence
    ii. the first universal tag
  c. amplifying a second nucleic acid molecule comprising in 5' to 3' order:
    i. a sequence of nucleotides that is the reverse complement of the second universal tag
    ii. a sequence of nucleotides that is the reverse complement of a second adapter sequence needed for subsequent processing
    iii. a blocking group preventing extension beyond the second adapter sequence
  using a second adapter primer that hybridizes with the reverse complement of the second adapter sequence to generate an amplification product comprising in 5' to 3' order:
    i. the second adapter sequence
    ii. the second universal tag
  d. amplifying the amplification products generated by the first primer pair using the amplification products of steps b and c as a universal primer pair in which the first and second universal tags act as primers to produce further amplification products incorporating the first and second universal tags and adapters, wherein the method is performed in a single reaction mixture.

59. A method of detecting and/or quantifying a target nucleic acid molecule comprising:
  a. performing the method of clause 58 in order to generate the further amplification products
  b. sequencing the further amplification products in order to detect and/or quantify the target nucleic acid molecule, optionally wherein the sequencing is next generation sequencing.

60. The set of reagents or method of any of clauses 56 to 59 wherein:
  a. the first nucleic acid molecule comprises in 5' to 3' order:
    i. a sequence of nucleotides that is the reverse complement of the first universal tag
    ii. a sequence of nucleotides that is the reverse complement of a first barcode, preferably a sample barcode
    iii. a sequence of nucleotides that is the reverse complement of a first adapter sequence needed for subsequent processing
    iv. a blocking group preventing extension beyond the adapter sequence and
  b. the first adapter primer hybridizes with the reverse complement of the first adapter sequence to generate an amplification product comprising in 5' to 3' order:
    i. the first adapter sequence
    ii. the first barcode, preferably first sample barcode
    iii. the first universal tag
    and wherein the further amplification products incorporate the first and second universal tags, first barcode, preferably first sample barcode, and first and second adapters.

61. The set of reagents or method of any of clauses 56 to 60 wherein:
  a. the second nucleic acid molecule comprises in 5' to 3' order:
    i. a sequence of nucleotides that is the reverse complement of the second universal tag ii. a sequence of nucleotides that is the reverse complement of a second barcode, preferably a sample barcode
iii. a sequence of nucleotides that is the reverse complement of a second adapter sequence needed for subsequent processing
iv. a blocking group preventing extension beyond the adapter sequence and
b. the second adapter primer hybridizes with the reverse complement of the second adapter sequence to generate an amplification product comprising in 5' to 3' order:
i. the second adapter sequence
ii. the second barcode, preferably second sample barcode
iii. the second universal tag
and wherein the further amplification products incorporate the first and second universal tags, second barcode, preferably second sample barcode, and first and second adapters.

62. The set of reagents or method of any of clauses 56 to 61 wherein the target nucleic acid molecule is DNA.
63. The set of reagents or method of any of clauses 56 to 62 wherein the target nucleic acid molecule is RNA.
64. The set of reagents or method of any of clauses 56 to 63 wherein the target nucleic acid molecule is:
    a. extracted from formalin-fixed and paraffin-embedded (FFPE) tissue; or
    b. is cell-free DNA, optionally:
        i. cell-free fetal DNA obtained from the maternal blood stream; or
        ii. cell free DNA obtained from body fluids, optionally blood, urine or spinal fluid; or
        iii. cell free tumour DNA
    c. is blood-derived.
65. A nucleic acid molecule, forming the reverse compliment of a universal primer, comprising in 5' to 3' order:
    a. a sequence of nucleotides that is the reverse complement of a tag
    b. optionally a sequence of nucleotides that is the reverse complement of a barcode, preferably a sample barcode
    c. a sequence of nucleotides that is the reverse complement of an adapter sequence needed for subsequent processing
    d. a blocking group preventing extension beyond the adapter sequence.
66. A combination of the nucleic acid molecule of clause 65 with a primer that hybridizes with the reverse complement of the adapter sequence to generate a universal primer as an amplification product comprising in 5' to 3' order:
    a. the adapter sequence needed for subsequent processing
    b. optionally the sample barcode
    c. the tag.
67. A combination of a first nucleic acid molecule comprising in 5' to 3' order:
    a. a sequence of nucleotides that is the reverse complement of a first universal tag
    b. optionally a sequence of nucleotides that is the reverse complement of a barcode sequence, preferably a sample barcode
    c. a sequence of nucleotides that is the reverse complement of a first adapter sequence needed for subsequent processing
    d. a blocking group preventing extension beyond the first adapter sequence;
together with a second nucleic acid molecule comprising in 5' to 3' order:
    e. a sequence of nucleotides that is the reverse complement of a second universal tag
    f. optionally a sequence of nucleotides that is the reverse complement of a barcode sequence, preferably a sample barcode
    g. a sequence of nucleotides that is the reverse complement of a second adapter sequence needed for subsequent processing
    h. a blocking group preventing extension beyond the second adapter sequence.
68. A combination of the nucleic acid molecules of clause 67 with:
    a. a first adapter primer that hybridizes with the reverse complement of the first adapter sequence to generate an amplification product comprising in 5' to 3' order:
        a. the first adapter sequence needed for subsequent processing
        b. optionally the first barcode sequence, preferably a sample barcode
        c. the first universal tag
    d. a second adapter primer that hybridizes with the reverse complement of the second adapter sequence to generate an amplification product comprising in 5' to 3' order:
        a. the second adapter sequence needed for subsequent processing
        b. optionally the second barcode sequence, preferably a sample barcode
        c. the second universal tag.
69. The set of reagents, method, nucleic acid molecule or combination of any of clauses 56 to 68 wherein the adapter sequence is an adapter sequence for next-generation sequencing.
70. The set of reagents, method, nucleic acid molecule or combination of any of clauses 59 to 70 wherein each barcode is at least 4, 6 or 8 nucleotides, optionally up to 20 nucleotides, in length.
71. The set of reagents, method, nucleic acid molecule or combination of any of clauses 56 to 70 wherein each tag is at least 20 nucleotides, optionally up to 30 nucleotides, in length.
72. The set of reagents, method, nucleic acid molecule or combination of any of clauses 56 to 71, wherein the blocking group is selected from the following: 3'ddC, 3' Inverted dT, 3' C3 spacer, 3' Amino, and 3' phosphorylation.
73. A multistep nucleic acid amplification reaction comprising amplification of a target nucleic acid molecule using a set of reagents as defined in any one of clauses 56 to 72 to create amplification products incorporating tags and adapter sequences.
74. A kit for multistep amplification of a target nucleic acid molecule comprising the set of reagents, nucleic acid molecule or combination of any one of clauses 56 to 72.
75. The kit of clauses 74 further comprising at least one of a DNA polymerase and dNTPs.
76. The set of reagents of any of clauses 56 to 72 comprising a set of primers, comprising at least the first and a second primer pair, designed to amplify overlapping regions of the target nucleic acid molecule.

77. The set of reagents of clause 77 wherein the set of primers comprise a set of primers as described in any one of clauses 1 to 17.

78. A multiplex and multistep amplification of a target nucleic acid molecule comprising use of a set of reagents as described in clause 76 or 77.

79. A method of detecting and/or quantifying a target nucleic acid molecule comprising:
   a. performing the amplification of clause 78 in order to generate amplification products incorporating universal tags and adapter sequences
   b. sequencing the amplification products in order to detect and/or quantify the target nucleic acid molecule, optionally wherein the sequencing is next generation sequencing.

80. The set of reagents according to any one of clauses 56 to 72 wherein at least one primer in the first primer pair is a primer according to any one of clauses 34 to 41.

81. The set of reagents according to any one of clauses 56 to 72 wherein both primers in the first primer pair are primers according to any one of clauses 34 to 41.

82. The set of reagents according to any one of clauses 56 to 72 wherein each primer designed to amplify the target nucleic acid molecule is a primer according to any one of clauses 34 to 41.

83. A multistep amplification of a target nucleic acid molecule comprising use of a set of reagents as claimed in any one of clauses 80 to 82.

84. A method of detecting and/or quantifying a target nucleic acid molecule comprising:
   a. performing the amplification of clause 83 in order to generate amplification products incorporating universal tags and adapter sequences
   b. sequencing the amplification products in order to detect and/or quantify the target nucleic acid molecule, optionally wherein the sequencing is next generation sequencing.

85. The set of reagents of any of clauses 56 to 72 comprising a set of primers, comprising at least the first and a second primer pair, designed to amplify overlapping regions of the target nucleic acid molecule.

86. The set of reagents of clause 85 wherein the set of primers comprise a set of primers as claimed in any one of clauses 48 to 51.

87. A multiplex and multistep amplification of a target nucleic acid molecule comprising use of a set of reagents as described in clause 85 or 86.

88. The amplification of clause 87 wherein the amplification comprises a multiplex nucleic acid amplification reaction comprising amplification of overlapping regions of a target nucleic acid molecule.

89. A method of detecting and/or quantifying a target nucleic acid molecule comprising:
   a. performing the amplification of clause 87 or 88 in order to generate amplification products incorporating universal tags and adapter sequences
   b. sequencing the amplification products in order to detect and/or quantify the target nucleic acid molecule, optionally wherein the sequencing is next generation sequencing.

The invention will now be better understood by the following illustrative, non-limiting examples.

EXAMPLES

Improving Multiplex Amplifications Involving Overlapping Target Sequences

Example 1—Use of Reciprocally Arranged Identical Tags Between Neighbouring Primer Pairs in a Multiplex Amplification of Overlapping Amplicons Reduces Aberrant Product Formation Methods An experiment was performed to show that one step multiplex for overlapping amplicons is performing as theoretically expected. As proof of concept, the BRCA tumor MASTR Dx assay (Multiplicom NV, Belgium) was utilised. This assay produces 181 amplicons of which 173 amplicons are amplified using overlapping primer pairs. Thus, there is the potential for generation of aberrant PCR fragments that are shorter than the expected PCR products when the amplification is performed as a multiplex reaction (i.e. as a single PCR reaction) with the original primer sets containing the regular arrangement of tag sequences. In order to show performance of the invention as a solution to this problem, the relevant primer sets were redesigned such that the tag sequences fulfilled the requirements for one step multiplex for overlapping amplicons (i.e. a reciprocating arrangement of tags on the primers between primer pairs as explained herein). Thus, in the existing primer sets, each forward primer contained tag 1 and each reverse primer contained tag 2. In the redesigned primers, neighbouring primer pairs had the opposite tag orientation (forward primer 1—tag 1, reverse primer 1—tag 2; forward primer 2—tag 2, reverse primer 2—tag 1 and so on). The tag 1 sequence is provided as SEQ ID NO: 1 and the tag 2 sequence is provided as SEQ ID NO: 2.

Both primer sets were used in a standard 2 step PCR protocol with the experimental conditions outlined in the instructions for use of this assay. Briefly, for each primer set one multiplex PCR reaction was set up using 50 ng of genomic template DNA and a first PCR reaction was performed for 20 cycles. The resulting amplicons were diluted 1000 fold and 2 µl of this diluted product was subsequently used in a standard second, 20 cycles, PCR.

Results

Figure 7:
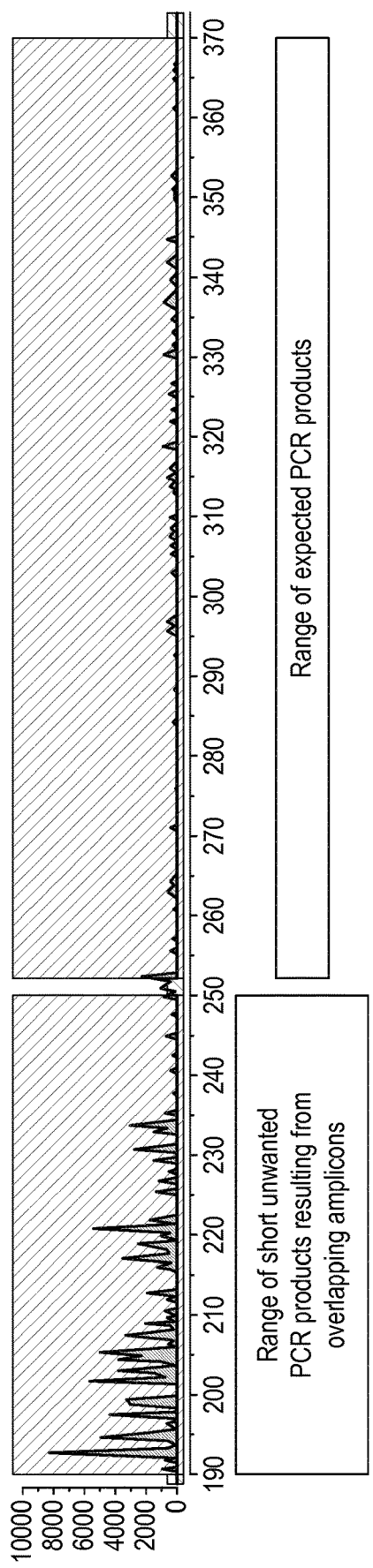
FIG. 7—A trace evidencing that use of standard BRCA tumor MASTR Dx primers results in the formation of aberrant short PCR products.
Figure 8:
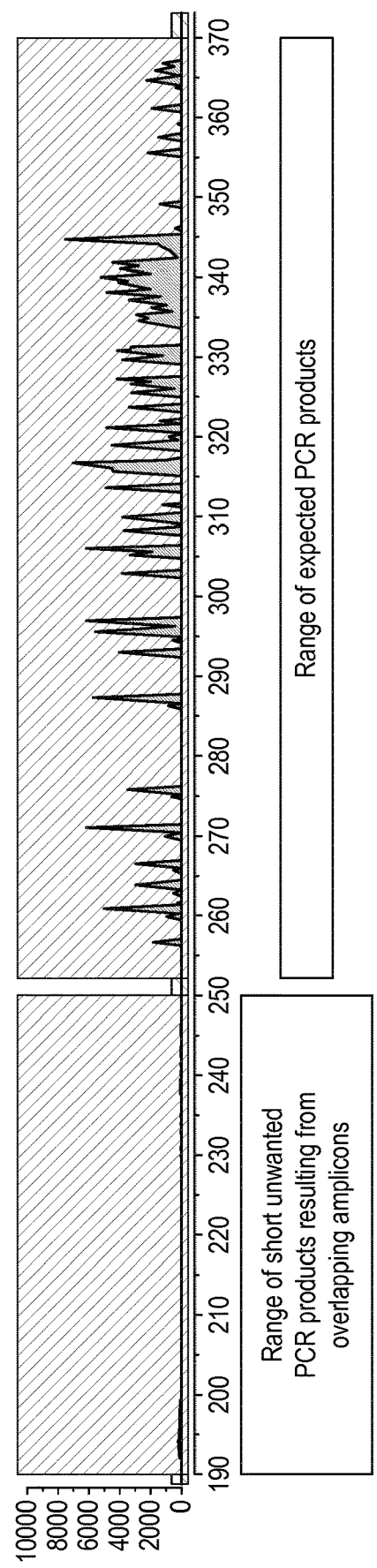
FIG. 8—A trace evidencing that adapting the tag sequences attached to the BRCA tumor primer pairs to comply with the one step multiplex for overlapping amplicons eliminates the formation of aberrant short PCR products and results only in production of the desired amplicons.

The resulting PCR products of both experiments were analysed on a fragment analyser (FIG. 7 and FIG. 8).

FIG. 7 shows that most single PCR reaction conditions with the standard BRCA tumor MASTR Dx primer results in the formation of PCR product in the size range that coincides with the short, unwanted amplicons which are formed between primers of overlapping amplicons and were the formation of shorter amplicons are favoured over the formation of the expected (longer) amplicons.

It is clear from FIG. 8 that adapting the tag sequences attached to the BRCA tumor primer pairs to comply with the one step multiplex for overlapping amplicons that only the expected amplicons are formed and no short unwanted amplicons are present in this experiment.

Enabling Multistep Amplification Reactions in a Single Reaction Mixture by Delaying Production of the Universal Primers Example 2—Reverse Compliment Sequences can be Amplified to Generate Universal Primers Using Primers that Hybridise to the Adaptor Portion of the Reverse Compliment Sequence Methods A first proof of concept experiment was performed to show that reverse complements of universal primers incorporating specific adaptor (and barcode) sequences, together with adaptor sequence primers (referred to in these examples as rcMID and p5/p7 primers respectively) can substitute the regular universal primers (referred to in these examples as MID primers) in order to generate the expected amplicons. Hereto, a 2-step PCR protocol was performed using regular MID sequences and rcMID+p5/p7 primers to amplify all target amplicons of a commercial assay (HNPCC MASTR). The procedure was performed as described in the HNPCC Instruction for use document (world wide web at multipli-com.com/product/hnpcc-mastr). Multiplex PCR based, targeted amplification conditions were performed using the HNPCC MASTR kit as described in the instruction for use with the modification that all HNPCC primers were mixed together in 1 reaction instead of 5 separate plexes. Briefly, one multiplex PCR reaction, containing all HNPCC primer pairs, was set up using 50 ng of genomic template DNA and a first PCR reaction was performed for 20 cycles. The resulting amplicons were diluted 1000 fold and 2 µl of this diluted product was subsequently used in a second, 20 cycles, PCR round with MID or rcMID+p5/p7 primers.

A second proof of concept experiment was performed to show that the rcMID+p5/p7 primers together with the first PCR primer pairs can generate the expected amplicons in a one-step reaction. Hereto, first PCR primer pairs from the first plex of BRCA tumor MASTR pluxs Dx commercial assay (world wide web at multiplicom.com/product/brca-tumor-mastr-plus-dx) were performed as a 2-step PCR using MID primers or as a one-step PCR using rcMID+p5/p7 primers. The 2 step PCR was performed in 2 reactions each of 20 PCR cycles. The one step PCR was performed in a single reaction over 30 PCR cycles. For both experiments 50 ng of input genomic DNA was used.

The P5 primer sequence is provided as SEQ ID NO: 3 and the P7 primer sequence is provided as SEQ ID NO: 4.

rcMID sequences, each of which was blocked with a 3' inverted dT blocking group, are provided as SEQ ID Nos 5-24. SEQ ID Nos 5-14 were extended to produce the MID primers for second stage amplification using the P5 primer. They contain the reverse compliment of the Tag 1 sequence and each includes a different barcode sequence immediately downstream of the tag sequence. SEQ ID Nos 15-24 were extended to produce the MID primers for second stage amplification using the P7 primer. They contain the reverse compliment of the Tag 2 sequence and each includes a different MID sequence immediately downstream of the tag sequence.

Results

Figure 14:
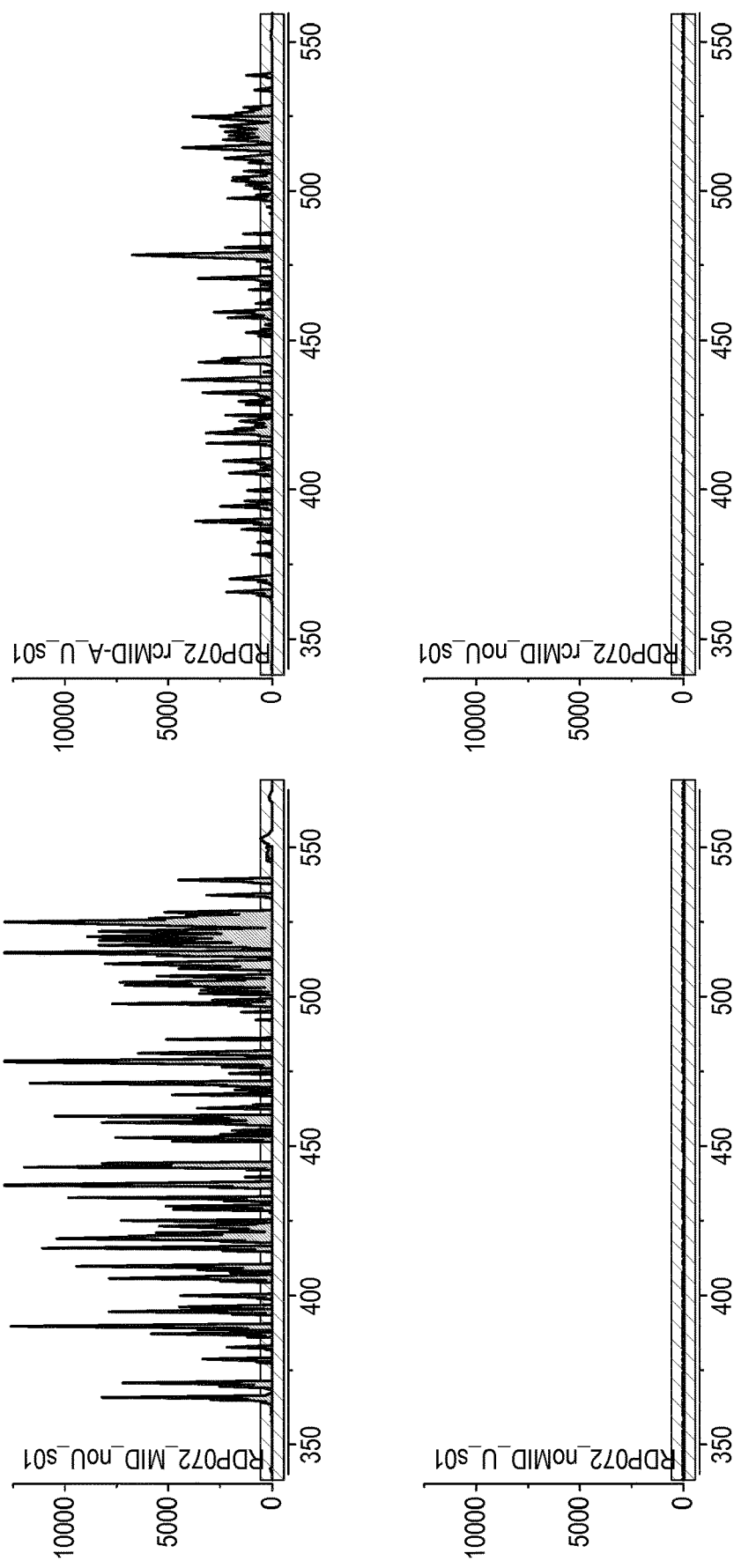
FIG. 14—Fragment analysis of the second PCR products with the MID and rcMID primers.

The result of the first proof of concept experiment is shown in FIG. 14. FIG. 14 presents fragment analysis results showing on the X-axes the length of the amplicons and on the Y-axes the yield of each amplicon which is presented as the height of each peak (the higher the better the yield).

The top left panel of FIG. 14 shows the fragment analysis result of the second PCR with the regular MID primers, resulting in the expected fragment analysis pattern for this assay.

The top right panel shows the fragment analysis result of the second PCR with the rcMID+p5/p7 primers. The resulting pattern was the same as the top left panel only the total yield was lower. This can be explained by the fact that generation of the MID primers from the rcMID primers delays the start of the second PCR to occur, resulting in lower yield.

Furthermore, the requirement to provide the reaction with rcMID and P5/P7 to obtain a successful second PCR are clear from the bottom panels. The left bottom panel shows the absence of amplification products when only P5 and P7 primers were added to the reaction. The bottom right panel shows the absence of amplification when only the rcMID primers were added without the p5/P7 primers.

Figure 15:
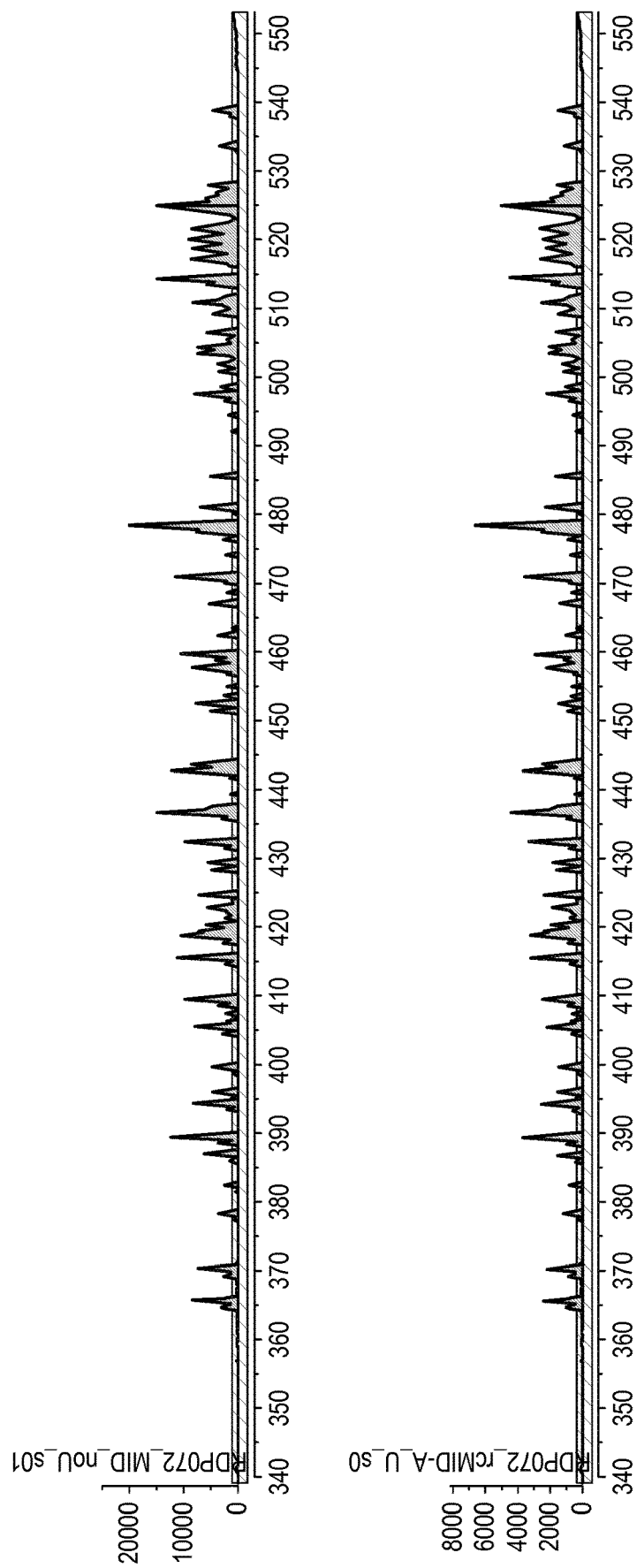
FIG. 15—Fragment analysis based comparison between the second PCR results with MID primers and rcMID+p5/p7 primers. The top panel results from amplification with the MID primers; The bottom panel results from amplification with the rcMID+p5/7 primers.

FIG. 15 shows a more detailed representation of the fragment analysis result of the results obtained with MID and rcMID+P5/P7 primers. This figure clearly shows that the pattern of both amplifications was identical and that only the yield was lower for the rcMID+p5/p7 reaction (bottom panel).

Figure 16:
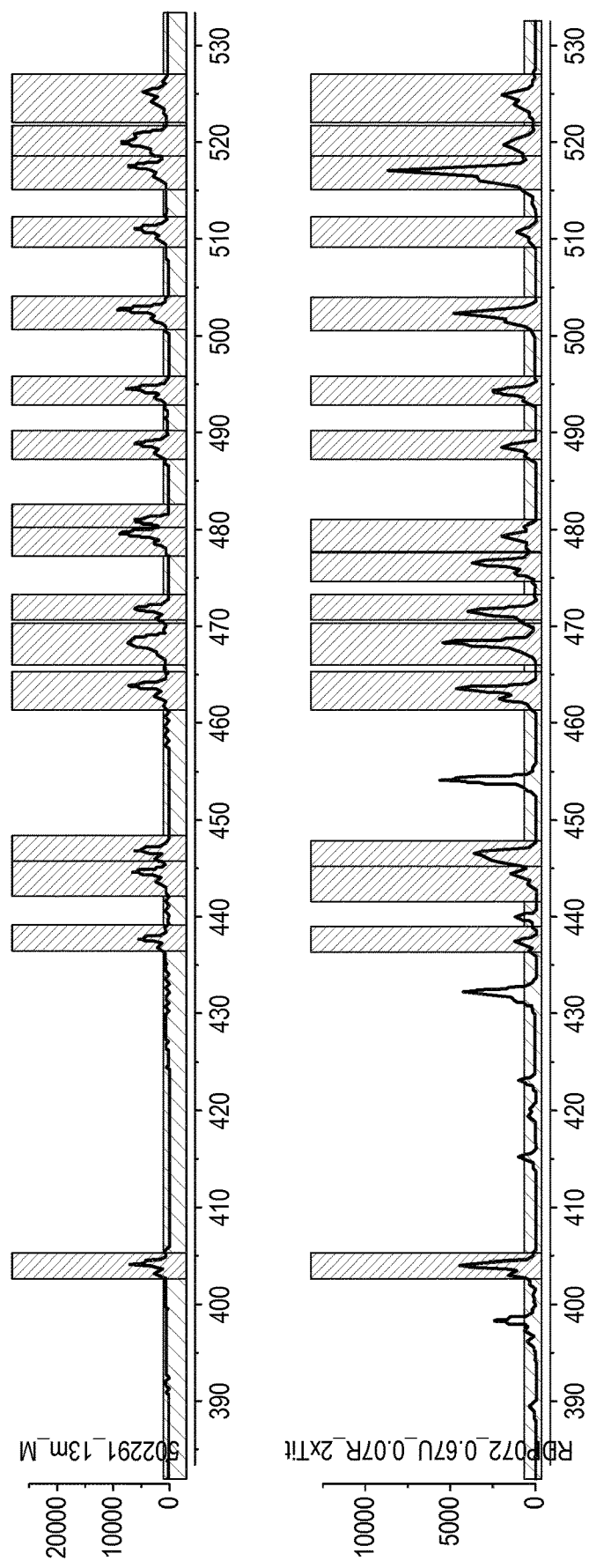
FIG. 16—Fragment analysis based comparison between the 2-step (top panel) and 1-step (bottom panel) PCR results with MID primers and rcMID+p5/p7 primers respectively. The coloured boxes indicate the positions of the expected amplicons.

The result of the second proof of concept experiment is shown in FIG. 16. From this figure it is clear that all expected amplicons were present in the one step PCR set-up (although at lower yield; note the Y-axis is not identical). Furthermore, it was observed in the one step PCR that additional amplicons were present. These extra amplicons were the result of the relative abundance of first PCR product amplicons leading to amplicons missing the MID primers at one or both ends of the final amplicons. Nevertheless, this data clearly shows that the rcMID+P5/P7 system permits both amplifications to be performed in the same single reaction mixture (one-step reaction).

Enabling Multistep Amplification Reactions in a Single Reaction Mixture by Delaying Production of the Universal Primers and by Controlling the Extent of the First Amplification Reaction Example 3—One Step Reaction A proof of concept experiment was performed to show that forward and reverse primers (i.e. primer pairs) each with an RNA base between primer region (that hybridises to the target sequence in the initial target DNA molecule) and tag sequence (first PCR primer pair) combined with the rcMID+p5/p7 primers generate fewer unwanted short PCR products in a one-step reaction (i.e. a reaction in which both first and second amplifications occur in the same reaction vessel in parallel) compared to non RNA-containing first PCR primer pairs in combination with rcMID+p5/p7 primers.

First PCR primer pairs with and without an RNA base between the primer region and the tag from the first plex of BRCA tumor MASTR plus Dx commercial assay (world wide web at multiplicom.com/product/brca-tumor-mastr-plus-dx) were mixed with rcMID+p5/p7 primers in a single tube. A one step PCR, intended to generate second round amplification products including suitable adaptors, was performed in a single reaction over 30 PCR cycles. For both experiments 50 ng of input genomic DNA was used. Primer concentrations of the first primers were 1:8 compared to primer concentrations used in a standard (target-specific) multiplex PCR reaction. Heat stable RNase H2 (IDT) was also added to the reaction at a concentration of 9.1 mU per reaction (or 0.45 mU per µl).

Results

The results of the proof of concept experiments are shown in FIGS. 17 and 18. These figures present fragment analysis results showing on the X-axis the length of the amplicons and on the Y-axis the yield of each amplicon which is presented as the height of each peak (the higher the peak, the better the yield).

It was expected that the one step reaction without the RNA base-containing first primer pairs would yield predominantly amplification products corresponding to amplification with the first primer pair. These amplification products are shorter than the desired amplification products arising following the second amplification, generated using the universal (MID) primers). This result was indeed observed as is clear from FIG. 17.

Figure 17A:
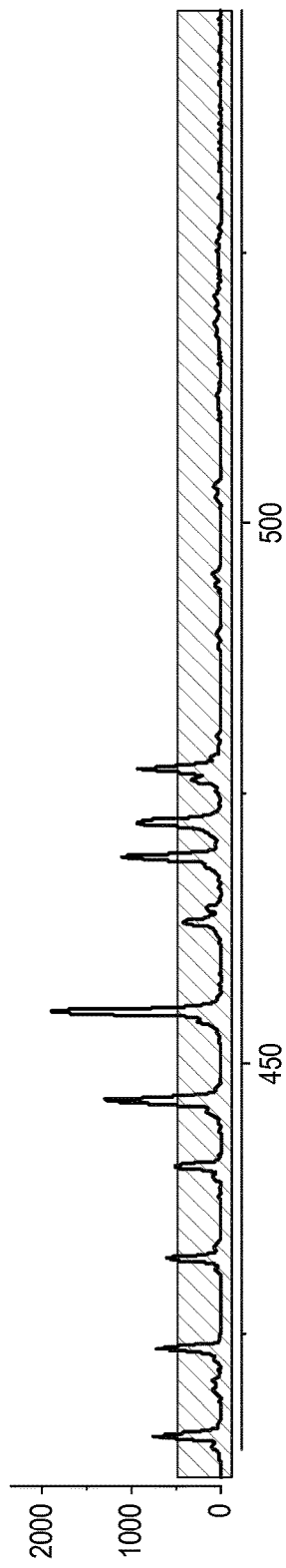
FIG. 17A—shows the fragment analysis result of the one step PCR without RNA base in the first primer pairs.
Figure 17B:
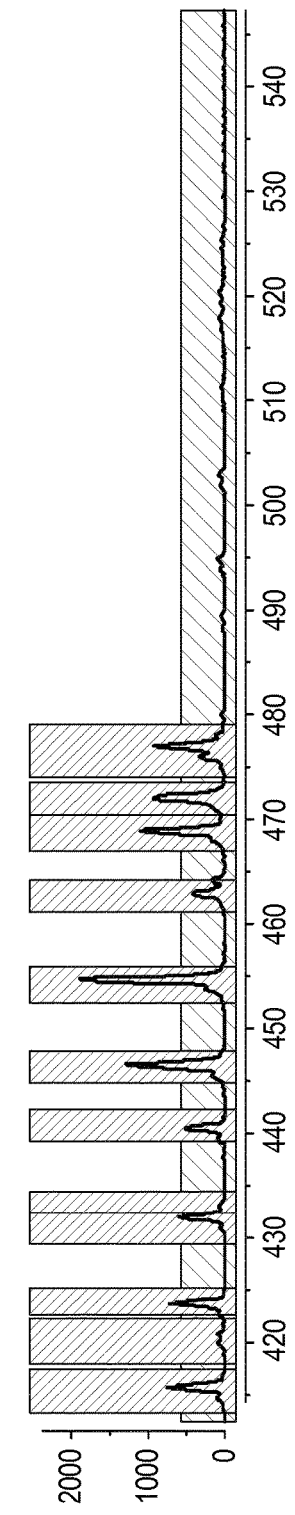
FIG. 17B—shows the same results but with a bin overlay (grey bands) in which each bin represents the expected size of the first PCR products.
Figure 17C:
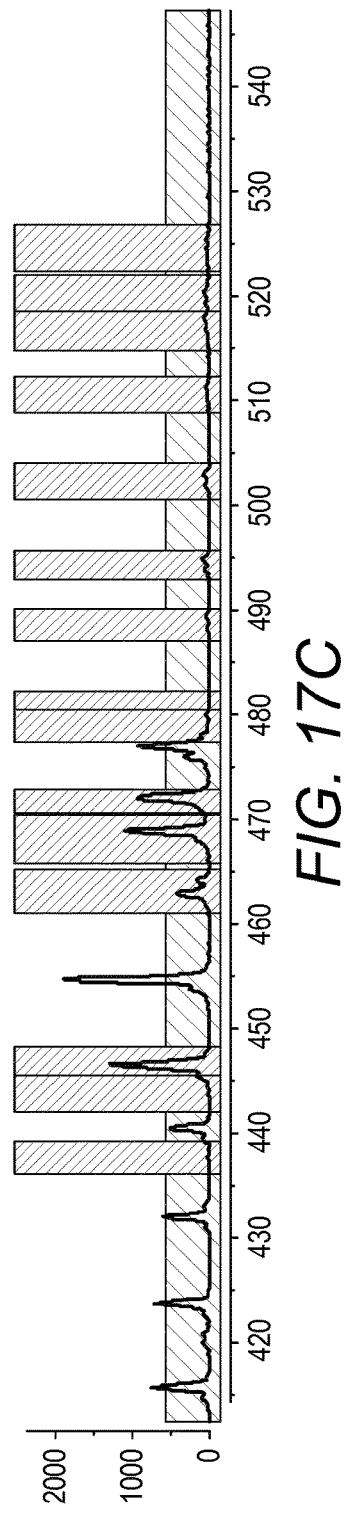
FIG. 17C—shows the same results but with a bin overlay (grey bands) in which each bin represents the expected size of PCR products after universal PCR.

The top panel, FIG. 17A, shows the fragment analysis result of the one step PCR without RNA base in the first primer pairs. The middle panel, FIG. 17B, shows the same results but with a bin overlay (grey bands) in which each bin represents the expected size of the first PCR products. It is clear from FIG. 17B that all formed amplicons were short amplicons expected from the first (target-specific) amplification while second round amplicons from the universal PCR were missing. FIG. 17C confirms this; here the bins (grey bands) represent the expected sizes of PCR products after universal PCR.

In contrast, it was expected that the one-step reaction with RNA base-containing first primer pairs would yield predominantly the desired amplification products arising from the second round, universal, PCR. Those amplification products are longer than the expected fragments generated with the first primer pairs. This result was indeed observed as is clear from FIG. 18.

Figure 18A:
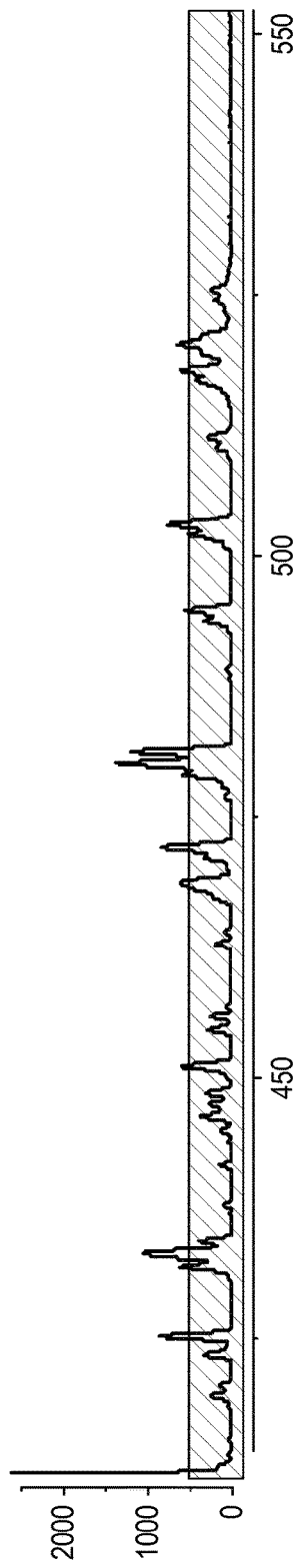
FIG. 18A—shows the fragment analysis result of the one step PCR with RNA base in the first primer pairs.
Figure 18B:
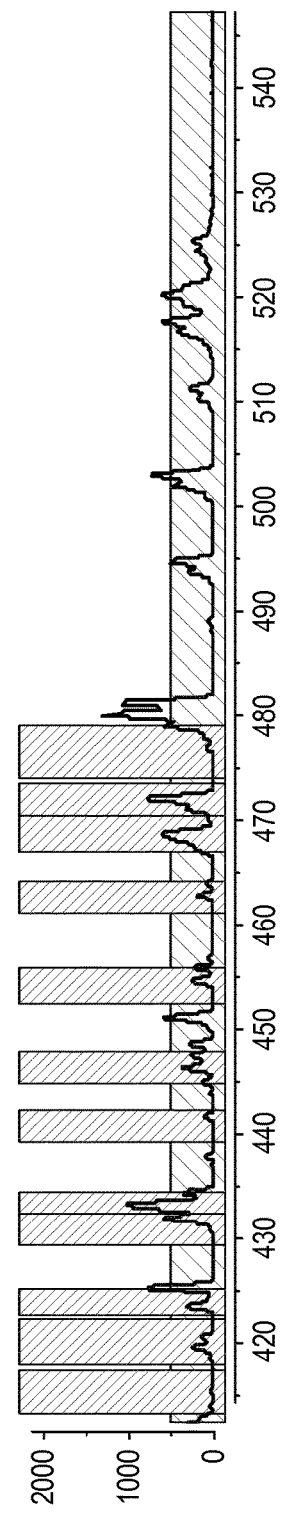
FIG. 18B—shows the same results but with a bin overlay (grey bands) in which each bin represents the expected size of the first PCR products.
Figure 18C:
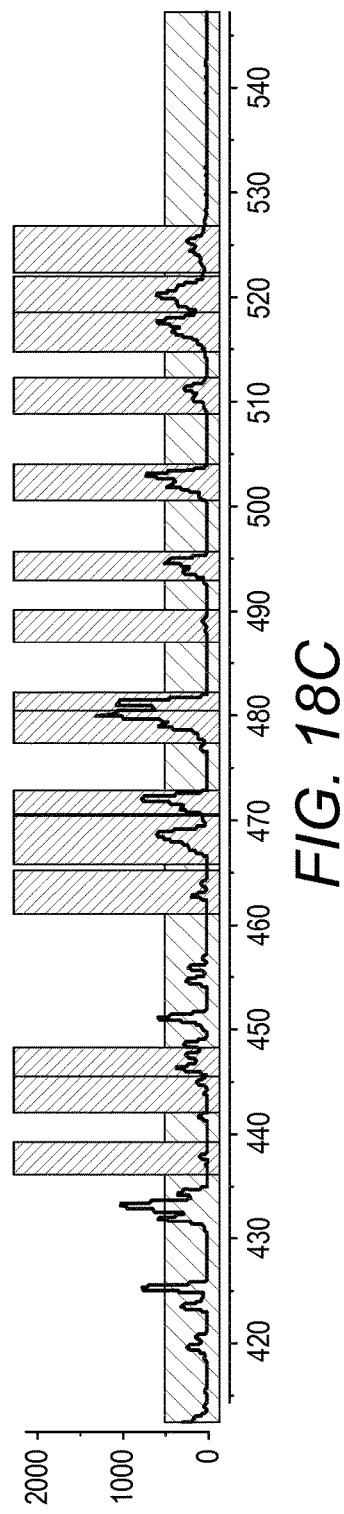
FIG. 18C—shows the same results but with a bin overlay (grey bands) in which each bin represents the expected size of PCR products after universal PCR.

The top panel, FIG. 18A, shows the fragment analysis result of the one step PCR with a RNA base in the first primer pairs. The bottom panel, FIG. 18C, shows the same results but with a bin overlay (grey bands) in which each bin represents the expected size of the universal PCR products. It is clear from FIG. 18C that most of the formed amplicons were long amplicons expected from the second round, universal, amplification while amplicons from the first PCR were missing. FIG. 18B confirms this; here the bins (grey bands) represent the expected sizes of PCR products after the first PCR.

This proof of concept experiment clearly shows that the addition of a RNA base in the first primer pairs allows target-specific and universal amplifications to be performed via a one step reaction, leading to the formation of the desired universal PCR sized products. In contrast, without the RNA base included in the first primer pairs only amplification products expected from the first PCR were observed.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A primer comprising, in 5' to 3' order:
 a) a universal tag;
 b) an RNA nucleotide;
 c) a primer region that does not comprise RNA nucleotides and that hybridizes with a strand of a target nucleic acid molecule;
 d) a further RNA nucleotide;
 e) a further region that hybridizes with a strand of the target nucleic acid molecule; and
 f) a blocking group.

2. A primer pair comprising a forward and reverse primer according to claim 1 for amplifying a target nucleic acid molecule.

3. A set of reagents for use in a multistep amplification of a target nucleic acid molecule, comprising:
 a primer pair according to claim 2; and
 RNase H.

4. A multistep amplification of a target nucleic acid molecule comprising amplifying a target nucleic acid with the primer pair according to claim 2.

5. A set of reagents for use in a multistep amplification of a target nucleic acid molecule, comprising:
 a primer according to claim 1; and
 RNase H.

6. A multistep amplification of a target nucleic acid molecule comprising amplifying a target nucleic acid with a primer according to claim 2.

7. A primer comprising, in 5' to 3' order:
 a) a universal tag that does not comprise RNA nucleotides;
 b) up to 4 nucleotides that hybridize with a strand of a target nucleic acid molecule;
 c) an RNA nucleotide; and
 d) a primer region that does not comprise RNA nucleotides and that hybridizes with a strand of the target nucleic acid molecule, wherein regions b and d both hybridize with the same target nucleic acid molecule resulting in a RNA nucleotide paired with a DNA base in the target nucleic acid molecule.

8. A primer pair comprising a forward and reverse primer according to claim 7 for amplifying a target nucleic acid molecule.

9. A set of reagents for use in a multistep amplification of a target nucleic acid molecule, comprising:
 a primer pair according to claim 8; and
 RNase H.

10. A multistep amplification of a target nucleic acid molecule comprising amplifying a target nucleic acid with the primer pair according to claim 8.

11. A set of reagents for use in a multistep amplification of a target nucleic acid molecule, comprising:
 a primer according to claim 7; and
 RNase H.

12. A multistep amplification of a target nucleic acid molecule comprising amplifying a target nucleic acid with a primer according to claim 7.

\* \* \* \* \*

```
                        SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
aagactcggc agcatctcca                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
gcgatcgtca ctgttctcca                                                   20

<210> SEQ ID NO 3
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 3
aatgatacgg cgaccaccga gatctacac                                         29

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide
```

<400> SEQUENCE: 4
caagcagaag acggcatacg agat                                          24

<210> SEQ ID NO 5
<211> LENGTH: 68
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag1
<220> FEATURE:
<221> NAME/KEY: misc_feature
<222> LOCATION: (21)..(39)
<223> OTHER INFORMATION: MID sequence
<220> FEATURE:
<221> NAME/KEY: misc_feature
<222> LOCATION: (40)..(68)
<223> OTHER INFORMATION: reverse complement of p5

<400> SEQUENCE: 5
ggagatgctg ccgagtcttt cctctgtcga cgtattgacg tgtagatctc ggtggtcgcc    60
gtatcatt                                                            68

<210> SEQ ID NO 6
<211> LENGTH: 68
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag1
<220> FEATURE:
<221> NAME/KEY: misc_feature
<222> LOCATION: (20)..(39)
<223> OTHER INFORMATION: MID sequence
<220> FEATURE:
<221> NAME/KEY: misc_feature
<222> LOCATION: (40)..(68)
<223> OTHER INFORMATION: reverse complement of p5

<400> SEQUENCE: 6
ggagatgctg ccgagtcttt cctctgtcga cactcaagtg tgtagatctc ggtggtcgcc    60
gtatcatt                                                            68

<210> SEQ ID NO 7
<211> LENGTH: 68
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag1
<220> FEATURE:
<221> NAME/KEY: misc_feature
<222> LOCATION: (20)..(39)
<223> OTHER INFORMATION: MID sequence
<220> FEATURE:
<221> NAME/KEY: misc_feature
<222> LOCATION: (40)..(68)
<223> OTHER INFORMATION: reverse complement of p5

<400> SEQUENCE: 7
ggagatgctg ccgagtcttt cctctgtcga cctcatgatg tgtagatctc ggtggtcgcc    60
gtatcatt                                                              68

<210> SEQ ID NO 8
<211> LENGTH: 68
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag1
<220> FEATURE:
<221> NAME/KEY: misc_feature
<222> LOCATION: (20)..(39)
<223> OTHER INFORMATION: MID sequence
<220> FEATURE:
<221> NAME/KEY: misc_feature
<222> LOCATION: (40)..(68)
<223> OTHER INFORMATION: reverse complement of p5

<400> SEQUENCE: 8
ggagatgctg ccgagtcttt cctctgtcga ctcatatcgg tgtagatctc ggtggtcgcc    60
gtatcatt                                                              68

<210> SEQ ID NO 9
<211> LENGTH: 68
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag1
<220> FEATURE:
<221> NAME/KEY: misc_feature
<222> LOCATION: (20)..(39)
<223> OTHER INFORMATION: MID sequence
<220> FEATURE:
<221> NAME/KEY: misc_feature
<222> LOCATION: (40)..(68)
<223> OTHER INFORMATION: reverse complement of p5

<400> SEQUENCE: 9
ggagatgctg ccgagtcttt cctctgtcga cctgccagag tgtagatctc ggtggtcgcc    60
gtatcatt                                                              68

<210> SEQ ID NO 10
<211> LENGTH: 68
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag1
<220> FEATURE:
<221> NAME/KEY: misc_feature
<222> LOCATION: (20)..(39)
<223> OTHER INFORMATION: MID sequence
<220> FEATURE:
<221> NAME/KEY: misc_feature
<222> LOCATION: (40)..(68)
<223> OTHER INFORMATION: reverse complement of p5

<400> SEQUENCE: 10
ggagatgctg ccgagtcttt cctctgtcga cgatggatag tgtagatctc ggtggtcgcc    60

```
gtatcatt                                                              68

<210> SEQ ID NO 11
<211> LENGTH: 68
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag1
<220> FEATURE:
<221> NAME/KEY: misc_feature
<222> LOCATION: (20)..(39)
<223> OTHER INFORMATION: MID sequence
<220> FEATURE:
<221> NAME/KEY: misc_feature
<222> LOCATION: (40)..(68)
<223> OTHER INFORMATION: reverse complement of p5

<400> SEQUENCE: 11
ggagatgctg ccgagtctttt cctctgtcga cctggacggg tgtagatctc ggtggtcgcc    60
gtatcatt                                                              68

<210> SEQ ID NO 12
<211> LENGTH: 68
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag1
<220> FEATURE:
<221> NAME/KEY: misc_feature
<222> LOCATION: (20)..(39)
<223> OTHER INFORMATION: MID sequence
<220> FEATURE:
<221> NAME/KEY: misc_feature
<222> LOCATION: (40)..(68)
<223> OTHER INFORMATION: reverse complement of p5

<400> SEQUENCE: 12
ggagatgctg ccgagtctttt cctctgtcga ctcacggacg tgtagatctc ggtggtcgcc    60
gtatcatt                                                              68

<210> SEQ ID NO 13
<211> LENGTH: 68
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag1
<220> FEATURE:
<221> NAME/KEY: misc_feature
<222> LOCATION: (20)..(39)
<223> OTHER INFORMATION: MID sequence
<220> FEATURE:
<221> NAME/KEY: misc_feature
<222> LOCATION: (40)..(68)
<223> OTHER INFORMATION: reverse complement of p5

<400> SEQUENCE: 13
ggagatgctg ccgagtctttt cctctgtcga ctatactagg tgtagatctc ggtggtcgcc    60
gtatcatt                                                              68
```

<210> SEQ ID NO 14
<211> LENGTH: 68
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag1
<220> FEATURE:
<221> NAME/KEY: misc_feature
<222> LOCATION: (20)..(39)
<223> OTHER INFORMATION: MID sequence
<220> FEATURE:
<221> NAME/KEY: misc_feature
<222> LOCATION: (40)..(68)
<223> OTHER INFORMATION: reverse complement of p5

<400> SEQUENCE: 14
ggagatgctg ccgagtcttt cctctgtcga cgcttgactg tgtagatctc ggtggtcgcc    60
gtatcatt                                                            68

<210> SEQ ID NO 15
<211> LENGTH: 67
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: reverse complement of Tag2
<220> FEATURE:
<221> NAME/KEY: misc_feature
<222> LOCATION: (21)..(43)
<223> OTHER INFORMATION: MID sequence
<220> FEATURE:
<221> NAME/KEY: misc_feature
<222> LOCATION: (44)..(67)
<223> OTHER INFORMATION: reverse complement of p7

<400> SEQUENCE: 15
ggagaacagt gacgatcgct tgggacctag gtaatggagg aacatctcgt atgccgtctt    60
ctgcttg                                                             67

<210> SEQ ID NO 16
<211> LENGTH: 67
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag2
<220> FEATURE:
<221> NAME/KEY: misc_feature
<222> LOCATION: (20)..(43)
<223> OTHER INFORMATION: MID sequence
<220> FEATURE:
<221> NAME/KEY: misc_feature
<222> LOCATION: (44)..(67)
<223> OTHER INFORMATION: reverse complement of p7

<400> SEQUENCE: 16
ggagaacagt gacgatcgct tgggacctag gtgatagtga ggaatctcgt atgccgtctt    60
ctgcttg                                                             67

<210> SEQ ID NO 17
<211> LENGTH: 67
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag2
<220> FEATURE:
<221> NAME/KEY: misc_feature
<222> LOCATION: (20)..(43)
<223> OTHER INFORMATION: MID sequence
<220> FEATURE:
<221> NAME/KEY: misc_feature
<222> LOCATION: (44)..(67)
<223> OTHER INFORMATION: reverse complement of p7

<400> SEQUENCE: 17
ggagaacagt gacgatcgct tgggacctag gatcaaaggg caaatctcgt atgccgtctt    60
ctgcttg                                                             67

<210> SEQ ID NO 18
<211> LENGTH: 67
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag2
<220> FEATURE:
<221> NAME/KEY: misc_feature
<222> LOCATION: (20)..(43)
<223> OTHER INFORMATION: MID sequence
<220> FEATURE:
<221> NAME/KEY: misc_feature
<222> LOCATION: (44)..(67)
<223> OTHER INFORMATION: reverse complement of p7

<400> SEQUENCE: 18
ggagaacagt gacgatcgct tgggacctag gcaccgggaa tcaatctcgt atgccgtctt    60
ctgcttg                                                             67

<210> SEQ ID NO 19
<211> LENGTH: 67
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag2
<220> FEATURE:
<221> NAME/KEY: misc_feature
<222> LOCATION: (20)..(43)
<223> OTHER INFORMATION: MID sequence
<220> FEATURE:
<221> NAME/KEY: misc_feature
<222> LOCATION: (44)..(67)
<223> OTHER INFORMATION: reverse complement of p7

<400> SEQUENCE: 19
ggagaacagt gacgatcgct tgggacctag gccgtagttt aggatctcgt atgccgtctt    60
ctgcttg                                                             67

```
<210> SEQ ID NO 20
<211> LENGTH: 67
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag2
<220> FEATURE:
<221> NAME/KEY: misc_feature
<222> LOCATION: (20)..(43)
<223> OTHER INFORMATION: MID sequence
<220> FEATURE:
<221> NAME/KEY: misc_feature
<222> LOCATION: (44)..(67)
<223> OTHER INFORMATION: reverse complement of p7

<400> SEQUENCE: 20
ggagaacagt gacgatcgct tgggacctag gtgtcgaaag agaatctcgt atgccgtctt      60
ctgcttg                                                               67

<210> SEQ ID NO 21
<211> LENGTH: 67
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag2
<220> FEATURE:
<221> NAME/KEY: misc_feature
<222> LOCATION: (20)..(43)
<223> OTHER INFORMATION: MID sequence
<220> FEATURE:
<221> NAME/KEY: misc_feature
<222> LOCATION: (44)..(67)
<223> OTHER INFORMATION: reverse complement of p7

<400> SEQUENCE: 21
ggagaacagt gacgatcgct tgggacctag gactgccatt aacatctcgt atgccgtctt      60
ctgcttg                                                               67

<210> SEQ ID NO 22
<211> LENGTH: 67
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag2
<220> FEATURE:
<221> NAME/KEY: misc_feature
<222> LOCATION: (20)..(43)
<223> OTHER INFORMATION: MID sequence
<220> FEATURE:
<221> NAME/KEY: misc_feature
<222> LOCATION: (44)..(67)
<223> OTHER INFORMATION: reverse complement of p7

<400> SEQUENCE: 22
ggagaacagt gacgatcgct tgggacctag gttggccact tccatctcgt atgccgtctt      60
ctgcttg                                                               67

<210> SEQ ID NO 23
```

```
<211> LENGTH: 67
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag2
<220> FEATURE:
<221> NAME/KEY: misc_feature
<222> LOCATION: (20)..(43)
<223> OTHER INFORMATION: MID sequence
<220> FEATURE:
<221> NAME/KEY: misc_feature
<222> LOCATION: (44)..(67)
<223> OTHER INFORMATION: reverse complement of p7

<400> SEQUENCE: 23
ggagaacagt gacgatcgct tgggacctag gattcctgtg agtatctcgt atgccgtctt     60
ctgcttg                                                               67

<210> SEQ ID NO 24
<211> LENGTH: 67
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: reverse complement of Tag2
<220> FEATURE:
<221> NAME/KEY: misc_feature
<222> LOCATION: (20)..(43)
<223> OTHER INFORMATION: MID sequence
<220> FEATURE:
<221> NAME/KEY: misc_feature
<222> LOCATION: (44)..(67)
<223> OTHER INFORMATION: reverse complement of p7

<400> SEQUENCE: 24
ggagaacagt gacgatcgct tgggacctag gccatggaca cagatctcgt atgccgtctt     60
ctgcttg                                                               67

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 25
cgcgcgcguc gatcgatcga t                                               21

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 26
cgcgcgcgcc uatcgatcga t                                               21

<210> SEQ ID NO 27
<211> LENGTH: 25
<212> TYPE: DNA
<213> ORGANISM: Artificial Sequence
```

```
<220> FEATURE:
<223> OTHER INFORMATION: Synthetic oligonucleotide

<400> SEQUENCE: 27
atcgatcgat cgatcggtat atata                                    25
```